(12) United States Patent
Kirsch et al.

(10) Patent No.: US 8,008,358 B2
(45) Date of Patent: Aug. 30, 2011

(54) FLUOROSURFACTANTS

(75) Inventors: Peer Kirsch, Kanagawa (JP);
Klaus-Dieter Franz, Kelkheim (DE);
Andreas Ruhl, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 1021 days.

(21) Appl. No.: 11/813,314

(22) PCT Filed: Dec. 22, 2005

(86) PCT No.: PCT/EP2005/013859
§ 371 (c)(1),
(2), (4) Date: Jul. 3, 2007

(87) PCT Pub. No.: WO2006/072401
PCT Pub. Date: Jul. 13, 2006

(65) Prior Publication Data
US 2008/0149878 A1    Jun. 26, 2008

(30) Foreign Application Priority Data
Jan. 5, 2005  (DE) .................. 10 2005 000 858

(51) Int. Cl.
*B01F 17/00* (2006.01)
(52) U.S. Cl. .............. 516/199; 516/198; 568/35; 568/74
(58) Field of Classification Search .................. 516/199; 252/2, 70, 8.81, 364, 182.12; 568/683, 74, 568/35; 106/311; 510/405; 508/567, 577
See application file for complete search history.

(56) References Cited

U.S. PATENT DOCUMENTS

| | | | |
|---|---|---|---|
| 3,102,903 A * | 9/1963 | Coffman et al. ............ | 560/147 |
| 4,849,540 A | 7/1989 | Sitzmann et al. | |
| 6,110,976 A | 8/2000 | Hansen et al. | |
| 7,195,863 B2 | 3/2007 | Takano et al. | |
| 2003/0138380 A1 | 7/2003 | Kalbanov et al. | |
| 2003/0153780 A1 | 8/2003 | Haniff et al. | |
| 2004/0106827 A1 * | 6/2004 | Dolbier et al. ............. | 562/826 |
| 2004/0234556 A1 * | 11/2004 | Kaldor et al. ............. | 424/400 |
| 2005/0038089 A1 * | 2/2005 | Neidhart et al. ........... | 514/370 |

FOREIGN PATENT DOCUMENTS

| | | |
|---|---|---|
| GB | 941392 | 11/1963 |
| GB | 941393 | 11/1963 |
| JP | 09/111286 | 4/1997 |
| JP | 2001/133984 | 5/2001 |
| WO | WO 03/010128 | 2/2003 |
| WO | WO 2004/011422 | 2/2004 |

OTHER PUBLICATIONS

Ben-David et al. ("A novel synthesis of trifluoromethyl ethers via xanthates, utilizing BrF3", Journal of Fluorine Chemistry 97 (1999) 75-78).*
Blazejewski et al. ("Synthesis of 2-trifluoromethoxyethyl trifluoromethoxyacetate and derived 2- trifluoromethoxyacrylates", Journal of Fluorine Chemistry 117 (2002) 161-166).*
Brel ("Synthesis and Diels-Alder Reactions of Dienophiles with Pentafluoro-λ6-sulfanyl (SF5) Moiety", Synthesis 2006, No. 2, pp. 0339-0343, Advanced online publication: Dec. 21, 2005).*
Willenbring et al. ("New pentafluorothio(SF5) alkylsulfonic acids", Can. J. Chem. 67, 2037-2040).*
Beilstein-Datenbank (Beilstein Institut zur Forderung der chemischen Wissenschaften; 2003).
N. H. Ray, J. Chem. So., Abstracts (1963), 1440.
A.F.T. Yokochi et al., Acta Cryst. 2002, E58, o1133-o1135.
R. Winter et al., Fjuorine Chem. 2000, 102, 79-87.
B. H. Ward et al., Chem. Mater., 2000, 12, 343-351.
J.P. Canselier et al., Magn. Reson. Chem. 1995, 33, 506-510.
R. Winter et al., J. Fluorine Chem., 1994., 66, 109-116.
K. Kanie et al., Bull. Chem. Soc. Jpn. 2000, 73, 471-484.
R. Winter et al., J. Fluorine Chem., 2001, 107, 23-30.
P. Kirsch et al., Angew. Chem., 1999, 111, 2174- 2178.
Angew. Chem., Int. Ed. Engl. 1999, 38, 1989-1992.
Ukrainskii Khimicheskii Zhurnal, 1978, 44 (10), 1057-9, L.M. Yagupol'skii et al.
OECD Guideline for the testing of chemicals, 115, Jul. 27, 1995.
OECD Guideline for the testing of chemicals, 302 B, Jul. 17, 1992.

* cited by examiner

*Primary Examiner* — Ling-Siu Choi
*Assistant Examiner* — Chun-Cheng Wang
(74) *Attorney, Agent, or Firm* — Millen, White, Zelano & Branigan, P.C.

(57) ABSTRACT

The present invention relates to the use of end groups Y, where Y stands for $CF_3O-$ or $F_5S-$, as hydrophobic end group in surface-active compounds, corresponding novel compounds, and processes for the preparation of these compounds.

43 Claims, 2 Drawing Sheets

FLUOROSURFACTANTS

The present invention relates to the use of end groups Y, where Y stands for $CF_3O-$ or $F_5S-$, as hydrophobic end group in surface-active compounds, corresponding novel compounds, and processes for the preparation of these compounds.

Fluorosurfactants have an outstanding ability to lower the surface energy, which is utilised, for example, in the hydrophobicisation of surfaces, such as textile impregnation, the hydrophobicisation of glass or the de-icing of air-craft wings.

In general, however, fluorosurfactants contain perfluoroalkyl substituents, which are degraded in the environment by biological and other oxidation processes to give perfluoroalkanecarboxylic acids and -sulfonic acids. These are regarded as persistent and are in some cases suspected of causing health problems (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, *Critical Reviews in Toxicology* 2004, 34, 351-384). In addition, relatively long-chain perfluoroalkanecarboxylic acids and -sulfonic acids accumulate in the food chain.

There is therefore a demand for surface-active substances having a property profile which is comparable to the classical fluorosurfactants, but which do not leave behind any persistent organofluorine degradation products on oxidative or reductive degradation.

The Omnova company markets polymers whose side chains have terminal $CF_3$ or $C_2F_5$ groups. International patent application WO 03/010128 describes perfluoroalkyl-substituted amines, acids, amino acids and thioether acids which have a $C_{3-20}$-perfluoroalkyl group.

JP-A-2001/133984 discloses surface-active compounds having perfluoroalkoxy chains which are suitable for use in antireflection coatings. JP-A-09/111286 discloses the use of perfluoropolyether surfactants in emulsions.

However, all fluorosurfactants disclosed hitherto ultimately result on degradation, in the formation of persistent perfluoroalkanesulfonic acids and -carboxylic acids. Even the substitutes having a terminal $CF_3$ group which were introduced as being more ecologically compatible can be degraded to give persistent trifluoroacetic acid. There therefore continues to be a demand for further, fully degradable substitutes for perfluorinated surfactants.

It has now been found that compounds which carry at least one terminal pentafluorosulfuranyl group or at least one terminal trifluoromethoxy group and have a polar end group are surface-active and are highly suitable as surfactants.

The present invention therefore relates firstly to the use of end groups Y, where Y stands for $CF_3O-$ or $F_5S-$, as hydrophobic end group in surface-active compounds.

The end group Y in the surface-active compounds is preferably bonded to a saturated or unsaturated, branched or unbranched hydrocarbon unit. The hydrocarbon units may be aliphatic or aromatic units, optionally provided with hetero atoms.

Besides the said fluorinated end groups, the compounds to be used in accordance with the invention preferably contain no further fluorinated groups.

In a variant of the invention, the end group Y occurs a number of times in the surface-active compound and the surface-active compound is preferably an oligomer or polymer.

In another, likewise preferred variant of the invention, the end group Y only occurs once, twice or three times in the surface-active compound, where compounds in which the end group only occurs once are particularly preferred. The compounds to be used in accordance with the invention are preferably low-molecular-weight compounds of the formula I

   I where
Y stands for $CF_3O-$ or $F_5S-$,
spacer stands for a saturated or unsaturated, branched or unbranched hydrocarbon unit,
X stands for a cationic, nonionic, amphoteric or anionic polar group or a polymerisable group.

It is particularly preferred here for the compound of the formula I to be selected from the compounds of the formulae Ia, Ib and Ic

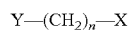   Ia

   Ib

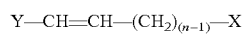   Ic in which Y stands for $CF_3O-$ or $F_5S-$,
n stands for an integer from the range 1 to 30 and
X stands for a cationic, nonionic, amphoteric or anionic polar group or a polymerisable group,
(Hal) stands for F, Cl, Br or I,
and corresponding salts of the compounds of the formula Ia, Ib or Ic.

Very particular preference is given here to the use of compounds of the formula Ia where n particularly preferably stands for an integer from the range 4 to 24 and especially preferably an integer from the range 6 to 18. In a variant of the invention, it is in turn preferred for n to be an even number.

Particular preference is given in accordance with the invention to the use of the above-mentioned compounds as surfactants.

If the compounds of the formula I are anionic compounds or compounds which can be converted into anions of salts, it is preferred for the counterion to be an alkali metal ion, preferably $Li^+$, $Na^+$ or $K^+$ an alkaline earth metal ion or $NH_4^+$. If the compounds of the formula I are cationic compounds or compounds which can be converted into cations of salts, it is preferred for the counterion to be a halide, such as $Cl^-$, $Br^-$ or $I^-$, or $CH_3SO_3^-$, $CF_3SO_3^-$, $CH_3PhSO_3^-$ or $PhSO_3^-$.

Some corresponding or structurally similar compounds are known from the literature:

The Beilstein database (Beilstein Institut zur Förderung der chemischen Wissenschaften; 2003) describes, inter alia, the compounds 2-(pentafluorosulfuranyl)ethanol, carboethoxymethylsulfur pentafluoride, pentafluorosulfuranylacetic acid and pentafluorosulfuranylethanesulfonic acid.

The preparation of pentafluorosulfuranylacetaldehyde and pentafluorosulfuranylacetic acid is described in N. H. Ray, *J. Chem. Soc., Abstracts* 1963, 1440, or GB 941,392 and GB 941,393. U.S. Pat. No. 3,102,903 describes the preparation of various pentafluorosulfuranylacetic acid derivatives.

Orthocarbonates and carbamates of pentafluorosulfuranylethanol having nitro end groups and the use thereof as explosive are described in U.S. Pat. No. 4,849,540.

A. F. T. Yokochi, R. Winter, G. Gard, *Acta Cryst.* 2002, E58, o1133-o1135 discloses the crystal structure of 3-pentafluorosulfuranylpropionic acid.

The preparation of various 3-pentafluorosulfuranylpropane derivatives is described in R. Winter, G. L. Gard, *J. Fluorine Chem.* 2000, 102, 79-87. Reaction of $SF_5Br$ with acrylic acid esters and subsequent modification of the ester group gives 3-pentafluorosulfuranylpropionic acid, 3-pentafluorosulfuranylpropanol and 3-bromo-1-pentafluorosulfuranylpropane.

Pentafluorosulfuranylmethanesulfonates $SF_5CX_2SO_3$ where X=H or F are described in B. H. Ward, J. A. Schlueter, U. Geiser, H. H. Wang, E. Morales, J. P. Parakka, S. Y. Thomas, J. M. Williams, P. G. Nixon, R. W. Winter, G. L. Gard, H.-J. Koo, M.-H. Whangboo, *Chem. Mater.* 2000,12, 343-351.

Pentafluorosulfuranylethanesulfonate is described in J. P. Canselier, J. L. Boyer, V. Castro, G. L. Gard, J. Mohtasam, D. H. Peyton, *Magn. Reson. Chem.* 1995, 33, 506-510.

R. Winter, G. I. Gard, *J. Fluorine Chem.* 1994, 66, 109-116 describes the preparation of various esters of pentafluorosulfuranylethanols and -propanols.

WO 2004/011422 describes the preparation of aliphatic and aromatic compounds having pentafluorosulfuranyl substituents. The preparation is carried out by the addition reaction of $SF_5Cl$ onto double bonds. For example, compounds of the $F_5S-CH_2-CHCl-(CH_2)_8-X^1$ type, where $X^1$ stands for OH, OC(=O)CH$_3$, Br, C(=O)OC$_2$H$_5$ or C(=O)CH$_3$, are prepared.

Advantages of the compounds according to the invention or use according to the invention of the said compounds or the compositions according to the invention may be, in particular:
  a surface activity which is superior to that of conventional hydrocarbon surfactants with respect to efficiency and/or effectiveness,
  biological and/or abiotic degradability of the substances without the formation of persistent, perfluorinated degradation products,
  good processing properties in formulations,
  storage stability.

The present invention furthermore relates to the corresponding novel compounds of the formula I, in particular compounds of the formula IIa, IIb or IIc $$CF_3O-(CH_2)_n-X \qquad \text{IIa}$$

$$CF_3O-CH_2-CH(Hal)-(CH_2)_{(n-1)}-X \qquad \text{IIb}$$

$$CF_3O-CH=CH-(CH_2)_{(n-1)}-X \qquad \text{IIc}$$

in which
n stands for an integer from the range 1 to 30 and
X stands for a cationic, nonionic, amphoteric or anionic polar group or a polymerisable group,
(Hal) stands for F, Cl, Br or I,
and corresponding salts of the compounds of the formula IIIa, IIIb or IIIc, where $CF_3-O-CH_2-COOH$ is excluded, and compounds of the formula IIIa, IIIb or IIIc $$F_5S-(CH_2)_n-X \qquad \text{IIIa}$$

$$F_5S-CH_2-CH(Hal)-(CH_2)_{(n-1)}-X \qquad \text{IIIb}$$

$$F_5S-CH=CH-(CH_2)_{(n-1)}-X \qquad \text{IIIc}$$

in which
n stands for an integer from the range 1 to 30 and
X stands for a cationic, nonionic, amphoteric or anionic polar group or a polymerisable group,
(Hal) stands for F, Cl, Br or I,
corresponding salts of the compounds of the formula IIIa, IIIb or IIIc, where the compounds. $F_5S-(CH_2)_1-CO_2M$, $F_5S-(CH_2)_2-CO_2M$, $F_5S-(CH_2)_1-SO_3M$, $F_5S-(CH_2)_2-SO_3M$, $F_5S-(CH_2)_1-CONH_2$, $F_5S-(CH_2)_2-OH$, $F_5S-(CH_2)_3-OH$ and $F_5S-CH_2-CHCl-(CH_2)_8-X^1$, where M stands for H or an alkali metal ion, preferably Li$^+$, Na$^+$ or K$^+$, or NH$_4^+$, and $X^1$ stands for OH, OC(=O)CH$_3$, Br, C(=O)OC$_2$H$_5$, C(=O)CH$_3$, are excluded.

n in compounds of the formula I or II or III preferably stands for a number from the range 4 to 28, particularly preferably a number from the range 8 to 24.

In a preferred group of compounds of the formula I to be employed in accordance with the invention or compounds of the formula II or III according to the invention, X stands for an anionic polar group selected from —COOM, —SO$_3$M, —OSO$_3$M, —PO$_3$M$_2$, —OPO$_3$M$_2$, —(OCH$_2$CH$_2$)$_m$—O—(CH$_2$)$_o$—COOM, —(OCH$_2$CH$_2$)$_m$—O—(CH$_2$)$_o$—SO$_3$M, —(OCH$_2$CH$_2$)$_m$—O—(CH$_2$)$_o$—SO$_3$M, —(OCH$_2$CH$_2$)$_m$—O—(CH$_2$)$_o$—PO$_3$M$_2$, —(OCH$_2$CH$_2$)$_m$—O—(CH$_2$)$_o$—OPO$_3$M$_2$, where M stands for H or an alkali metal ion, preferably Li$^+$, Na$^+$ or K$^+$, or NH$_4^+$, m stands for an integer from the range 1 to 1000, and o stands for an integer selected from 1, 2, 3 or 4.

The preferred anionic groups here include, in particular, —COOM, —SO$_3$M, —OS$_3$M, as well as —(OCH$_2$CH$_2$)$_m$—O—(CH$_2$)$_o$—COOM, —(OCH$_2$CH$_2$)$_m$—O—(CH$_2$)$_o$—SO$_3$M and —(OCH$_2$CH$_2$)$_m$—O—(CH$_2$)$_o$—OSO$_3$M, where each individual one of these groups taken for itself may be preferred.

In another, likewise preferred group of compounds of the formula I to be employed in accordance with the invention or compounds of the formula II or III according to the invention, X stands for a cationic polar group selected from $-NR^1R^2R^3{}^+Z^-$, $-PR^1R^2R^3{}^+Z^-$,

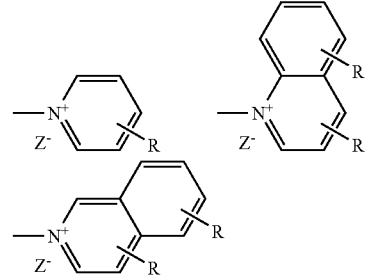

where R stands for H or C$_{1-4}$-alkyl in any desired position, Z$^-$ stands for Cl$^-$, Br$^-$, I$^-$, CH$_3$SO$_3^-$;, CF$_3$SO$_3^-$, CH$_3$PhSO$_3^-$, PhSO$_3^-$, R$^1$, R$^2$ and R$^3$ each, independently of one another, stand for H, C$_{1-30}$-alkyl, Ar or —CH$_2$Ar and Ar stands for an unsubstituted or mono- or polysubstituted aromatic ring or fused ring system having 6 to 18 C atoms, in which, in addition, one or two CH groups may be replaced by N.

The preferred cationic groups here include, in particular, $-NR^1R^2R^3{}^+Z^-$ and

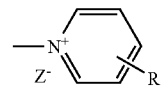

where each individual one of these groups taken for itself may be preferred.

In a further preferred group of compounds of the formula I to be employed in accordance with the invention or compounds of the formula II or III according to the invention, X stands for a nonionic polar group selected from —Cl, —Br, —I, —(OCH$_2$CH$_2$)$_m$—OH, —O-(glycoside)$_o$, —(OCH$_2$CH$_2$)$_m$—OCH$_2$—CHOH—CH$_2$—OH, —(OCH$_2$CH$_2$)$_m$—OCH$_2$Ar(—NCO)$_p$, —(OCH$_2$CH$_2$)$_m$—OAr(—NCO)$_p$, —SiR$^1$R$^2$Z, —SiR$^1$Z$_2$, —SiZ$_3$, —COZ, —(OCH$_2$CH$_2$)$_m$—SO$_2$CH=CH$_2$, —SO$_2$Z,

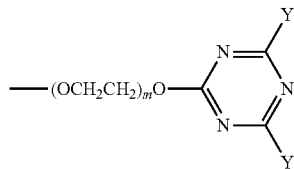

m stands for an integer from the range 0 to 1000,
n stands for 0 or 1 and
o stands for an integer from the range 1 to 10,
p stands for 1 or 2,
R$^1$ and R$^2$ each, independently of one another, stand for C$_{1-30}$-alkyl,
Ar or —CH$_2$Ar and Ar stands for an unsubstituted, mono- or polysubstituted aromatic ring or fused ring system having 6 to 18 C atoms, in which, in addition, one or two CH groups may be replaced by C=O, and
glycoside stands for an etherified carbohydrate, preferably a mono-, di-, tri- or oligoglucoside,
all Z each, independently of one another, stand for —H, —Cl, —F, —NR$^1$R$^2$, —OR$^1$, —N-imidazolyl, and
Y stands for Cl or F.

The preferred nonionic polar groups here include, in particular, —(OCH$_2$CH$_2$)$_m$—OH and —O-(glycoside)$_o$, where each individual one of these groups taken for itself may be preferred.

In addition, compounds of the formula I, II or III in which X stands for a polymerisable group selected from —(OCH$_2$CH$_2$)$_m$OCOCR=CH$_2$, —(OCH$_2$CH$_2$)$_m$—OCR=CH$_2$,

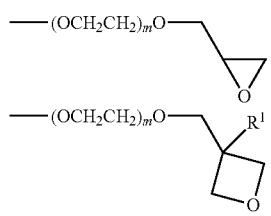

where m stands for an integer from the range 0 to 1000 and R and R$^1$ stand for H or C$_{1-4}$-alkyl, may be preferred or preferably used in accordance with the invention. These compounds are preferably converted into polymers having corresponding side chains, which may themselves again be employed in the sense according to the invention. The present invention also relates to the use of these polymers.

In addition, compounds in which X stands for an amphoteric group selected from the functional groups of the acetyldiamines, the N-alkylamino acids, the betaines, the amine oxides or corresponding derivatives may be preferred or preferably used in accordance with the invention. In preferred compounds of this class of substances, X is a group selected from

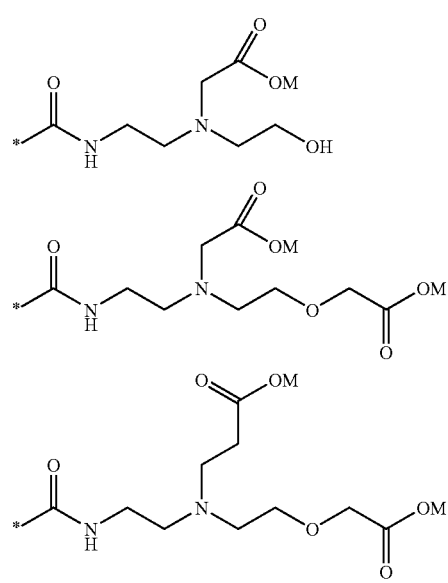

The particularly preferred compounds here include the compounds shown in the following table:

| | | |
|---|---|---|
| CF$_3$—O—(CH$_2$)$_4$—COOH; | CF$_3$—O—(CH$_2$)$_4$—SO$_3$H; | CF$_3$—O—(CH$_2$)$_4$—O—SO$_3$H |
| CF$_3$—O—(CH$_2$)$_5$—COOH; | CF$_3$—O—(CH$_2$)$_5$—SO$_3$H; | CF$_3$—O—(CH$_2$)$_5$—O—SO$_3$H |
| CF$_3$—O—(CH$_2$)$_6$—COOH; | CF$_3$—O—(CH$_2$)$_6$—SO$_3$H; | CF$_3$—O—(CH$_2$)$_6$—O—SO$_3$H |
| CF$_3$—O—(CH$_2$)$_7$—COOH; | CF$_3$—O—(CH$_2$)$_7$—SO$_3$H; | CF$_3$—O—(CH$_2$)$_7$—O—SO$_3$H |
| CF$_3$—O—(CH$_2$)$_8$—COOH; | CF$_3$—O—(CH$_2$)$_8$—SO$_3$H; | CF$_3$—O—(CH$_2$)$_8$—O—SO$_3$H |
| CF$_3$—O—(CH$_2$)$_9$—COOH; | CF$_3$—O—(CH$_2$)$_9$—SO$_3$H; | CF$_3$—O—(CH$_2$)$_9$—O—SO$_3$H |
| CF$_3$—O—(CH$_2$)$_{10}$—COOH; | CF$_3$—O—(CH$_2$)$_{10}$—SO$_3$H; | CF$_3$—O—(CH$_2$)$_{10}$—O—SO$_3$H |
| CF$_3$—O—(CH$_2$)$_{11}$—COOH; | CF$_3$—O—(CH$_2$)$_{11}$—SO$_3$H; | CF$_3$—O—(CH$_2$)$_{11}$—O—SO$_3$H |
| CF$_3$—O—(CH$_2$)$_{12}$—COOH; | CF$_3$—O—(CH$_2$)$_{12}$—SO$_3$H; | CF$_3$—O—(CH$_2$)$_{12}$—O—SO$_3$H |
| CF$_3$—O—(CH$_2$)$_{13}$—COOH; | CF$_3$—O—(CH$_2$)$_{13}$—SO$_3$H; | CF$_3$—O—(CH$_2$)$_{13}$—O—SO$_3$H |
| CF$_3$—O—(CH$_2$)$_{14}$—COOH; | CF$_3$—O—(CH$_2$)$_{14}$—SO$_3$H; | CF$_3$—O—(CH$_2$)$_{14}$—O—SO$_3$H |
| CF$_3$—O—(CH$_2$)$_{15}$—COOH; | CF$_3$—O—(CH$_2$)$_{15}$—SO$_3$H; | CF$_3$—O—(CH$_2$)$_{15}$—O—SO$_3$H |
| CF$_3$—O—(CH$_2$)$_{16}$—COOH; | CF$_3$—O—(CH$_2$)$_{16}$—SO$_3$H; | CF$_3$—O—(CH$_2$)$_{16}$—O—SO$_3$H |
| CF$_3$—O—(CH$_2$)$_{17}$—COOH; | CF$_3$—O—(CH$_2$)$_{17}$—SO$_3$H; | CF$_3$—O—(CH$_2$)$_{17}$—O—SO$_3$H |
| CF$_3$—O—(CH$_2$)$_{18}$—COOH; | CF$_3$—O—(CH$_2$)$_{18}$—SO$_3$H; | CF$_3$—O—(CH$_2$)$_{18}$—O—SO$_3$H |
| CF$_3$—O—(CH$_2$)$_{19}$—COOH; | CF$_3$—O—(CH$_2$)$_{19}$—SO$_3$H; | CF$_3$—O—(CH$_2$)$_{19}$—O—SO$_3$H |

-continued $CF_3-O-(CH_2)_{20}-COOH$; $CF_3-O-(CH_2)_{20}-SO_3H$; $CF_3-O-(CH_2)_{20}-O-SO_3H$
$CF_3-O-(CH_2)_{21}-COOH$; $CF_3-O-(CH_2)_{21}-SO_3H$; $CF_3-O-(CH_2)_{21}-O-SO_3H$
$CF_3-O-(CH_2)_{22}-COOH$; $CF_3-O-(CH_2)_{22}-SO_3H$; $CF_3-O-(CH_2)_{22}-O-SO_3H$
$CF_3-O-(CH_2)_{23}-COOH$; $CF_3-O-(CH_2)_{23}-SO_3H$; $CF_3-O-(CH_2)_{23}-O-SO_3H$
$CF_3-O-(CH_2)_{24}-COOH$; $CF_3-O-(CH_2)_{24}-SO_3H$; $CF_3-O-(CH_2)_{24}-O-SO_3H$
$SF_5-(CH_2)_4-COOH$; $SF_5-(CH_2)_4-SO_3H$; $SF_5-(CH_2)_4-O-SO_3H$
$SF_5-(CH_2)_5-COOH$; $SF_5-(CH_2)_5-SO_3H$; $SF_5-(CH_2)_5-O-SO_3H$
$SF_5-(CH_2)_6-COOH$; $SF_5-(CH_2)_6-SO_3H$; $SF_5-(CH_2)_6-O-SO_3H$
$SF_5-(CH_2)_7-COOH$; $SF_5-(CH_2)_7-SO_3H$; $SF_5-(CH_2)_7-O-SO_3H$
$SF_5-(CH_2)_8-COOH$; $SF_5-(CH_2)_8-SO_3H$; $SF_5-(CH_2)_8-O-SO_3H$
$SF_5-(CH_2)_9-COOH$; $SF_5-(CH_2)_9-SO_3H$; $SF_5-(CH_2)_9-O-SO_3H$
$SF_5-(CH_2)_{10}-COOH$; $SF_5-(CH_2)_{10}-SO_3H$; $SF_5-(CH_2)_{10}-O-SO_3H$
$SF_5-(CH_2)_{11}-COOH$; $SF_5-(CH_2)_{11}-SO_3H$; $SF_5-(CH_2)_{11}-O-SO_3H$
$SF_5-(CH_2)_{12}-COOH$; $SF_5-(CH_2)_{12}-SO_3H$; $SF_5-(CH_2)_{12}-O-SO_3H$
$SF_5-(CH_2)_{13}-COOH$; $SF_5-(CH_2)_{13}-SO_3H$; $SF_5-(CH_2)_{13}-O-SO_3H$
$SF_5-(CH_2)_{14}-COOH$; $SF_5-(CH_2)_{14}-SO_3H$; $SF_5-(CH_2)_{14}-O-SO_3H$
$SF_5-(CH_2)_{15}-COOH$; $SF_5-(CH_2)_{15}-SO_3H$; $SF_5-(CH_2)_{15}-O-SO_3H$
$SF_5-(CH_2)_{16}-COOH$; $SF_5-(CH_2)_{16}-SO_3H$; $SF_5-(CH_2)_{16}-O-SO_3H$
$SF_5-(CH_2)_{17}-COOH$; $SF_5-(CH_2)_{17}-SO_3H$; $SF_5-(CH_2)_{17}-O-SO_3H$
$SF_5-(CH_2)_{18}-COOH$; $SF_5-(CH_2)_{18}-SO_3H$; $SF_5-(CH_2)_{18}-O-SO_3H$
$SF_5-(CH_2)_{19}-COOH$; $SF_5-(CH_2)_{19}-SO_3H$; $SF_5-(CH_2)_{19}-O-SO_3H$
$SF_5-(CH_2)_{20}-COOH$; $SF_5-(CH_2)_{20}-SO_3H$; $SF_5-(CH_2)_{20}-O-SO_3H$
$SF_5-(CH_2)_{21}-COOH$; $SF_5-(CH_2)_{21}-SO_3H$; $SF_5-(CH_2)_{21}-O-SO_3H$
$SF_5-(CH_2)_{22}-COOH$; $SF_5-(CH_2)_{22}-SO_3H$; $SF_5-(CH_2)_{22}-O-SO_3H$
$SF_5-(CH_2)_{23}-COOH$; $SF_5-(CH_2)_{23}-SO_3H$; $SF_5-(CH_2)_{23}-O-SO_3H$
$SF_5-(CH_2)_{24}-COOH$; $SF_5-(CH_2)_{24}-SO_3H$; $SF_5-(CH_2)_{24}-O-SO_3H$
$SF_5-CH=CH-(CH_2)_4-COOH$; $SF_5-CH=CH-(CH_2)_4-SO_3H$; $SF_5-CH=CH-(CH_2)_4-O-SO_3H$
$SF_5-CH=CH-(CH_2)_5-COOH$; $SF_5-CH=CH-(CH_2)_5-SO_3H$; $SF_5-CH=CH-(CH_2)_5-O-SO_3H$
$SF_5-CH=CH-(CH_2)_6-COOH$; $SF_5-CH=CH-(CH_2)_6-SO_3H$; $SF_5-CH=CH-(CH_2)_6-O-SO_3H$
$SF_5-CH=CH-(CH_2)_7-COOH$; $SF_5-CH=CH-(CH_2)_7-SO_3H$; $SF_5-CH=CH-(CH_2)_7-O-SO_3H$
$SF_5-CH=CH-(CH_2)_8-COOH$; $SF_5-CH=CH-(CH_2)_8-SO_3H$; $SF_5-CH=CH-(CH_2)_8-O-SO_3H$
$SF_5-CH=CH-(CH_2)_9-COOH$; $SF_5-CH=CH-(CH_2)_9-SO_3H$; $SF_5-CH=CH-(CH_2)_9-O-SO_3H$
$SF_5-CH=CH-(CH_2)_{10}-COOH$; $SF_5-CH=CH-(CH_2)_{10}-SO_3H$; $SF_5-CH=CH-(CH_2)_{10}-O-SO_3H$
$SF_5-CH=CH-(CH_2)_{11}-COOH$; $SF_5-CH=CH-(CH_2)_{11}-SO_3H$; $SF_5-CH=CH-(CH_2)_{11}-O-SO_3H$
$SF_5-CH=CH-(CH_2)_{12}-COOH$; $SF_5-CH=CH-(CH_2)_{12}-SO_3H$; $SF_5-CH=CH-(CH_2)_{12}-O-SO_3H$
$SF_5-CH=CH-(CH_2)_{13}-COOH$; $SF_5-CH=CH-(CH_2)_{13}-SO_3H$; $SF_5-CH=CH-(CH_2)_{13}-O-SO_3H$
$SF_5-CH=CH-(CH_2)_{14}-COOH$; $SF_5-CH=CH-(CH_2)_{14}-SO_3H$; $SF_5-CH=CH-(CH_2)_{14}-O-SO_3H$
$SF_5-CH=CH-(CH_2)_{15}-COOH$; $SF_5-CH=CH-(CH_2)_{15}-SO_3H$; $SF_5-CH=CH-(CH_2)_{15}-O-SO_3H$
$SF_5-CH=CH-(CH_2)_{16}-COOH$; $SF_5-CH=CH-(CH_2)_{16}-SO_3H$; $SF_5-CH=CH-(CH_2)_{16}-O-SO_3H$
$SF_5-CH=CH-(CH_2)_{17}-COOH$; $SF_5-CH=CH-(CH_2)_{17}-SO_3H$; $SF_5-CH=CH-(CH_2)_{17}-O-SO_3H$
$SF_5-CH=CH-(CH_2)_{18}-COOH$; $SF_5-CH=CH-(CH_2)_{18}-SO_3H$; $SF_5-CH=CH-(CH_2)_{18}-O-SO_3H$
$SF_5-CH=CH-(CH_2)_{19}-COOH$; $SF_5-CH=CH-(CH_2)_{19}-SO_3H$; $SF_5-CH=CH-(CH_2)_{19}-O-SO_3H$
$SF_5-CH=CH-(CH_2)_{20}-COOH$; $SF_5-CH=CH-(CH_2)_{20}-SO_3H$; $SF_5-CH=CH-(CH_2)_{20}-O-SO_3H$
$SF_5-CH=CH-(CH_2)_{21}-COOH$; $SF_5-CH=CH-(CH_2)_{21}-SO_3H$; $SF_5-CH=CH-(CH_2)_{21}-O-SO_3H$
$SF_5-CH=CH-(CH_2)_{22}-COOH$; $SF_5-CH=CH-(CH_2)_{22}-SO_3H$; $SF_5-CH=CH-(CH_2)_{22}-O-SO_3H$
$SF_5-CH=CH-(CH_2)_{23}-COOH$; $SF_5-CH=CH-(CH_2)_{23}-SO_3H$; $SF_5-CH=CH-(CH_2)_{23}-O-SO_3H$
$SF_5-CH=CH-(CH_2)_{24}-COOH$; $SF_5-CH=CH-(CH_2)_{24}-SO_3H$; $SF_5-CH=CH-(CH_2)_{24}-O-SO_3H$
$SF_5-CH_2CHBr-(CH_2)_4-COOH$; $SF_5-CH_2CHBr-(CH_2)_4-SO_3H$; $SF_5-CH_2CHBr-(CH_2)_4-O-SO_3H$
$SF_5-CH_2CHBr-(CH_2)_5-COOH$; $SF_5-CH_2CHBr-(CH_2)_5-SO_3H$; $SF_5-CH_2CHBr-(CH_2)_5-O-SO_3H$
$SF_5-CH_2CHBr-(CH_2)_6-COOH$; $SF_5-CH_2CHBr-(CH_2)_6-SO_3H$; $SF_5-CH_2CHBr-(CH_2)_6-O-SO_3H$
$SF_5-CH_2CHBr-(CH_2)_7-COOH$; $SF_5-CH_2CHBr-(CH_2)_7-SO_3H$; $SF_5-CH_2CHBr-(CH_2)_7-O-SO_3H$
$SF_5-CH_2CHBr-(CH_2)_8-COOH$; $SF_5-CH_2CHBr-(CH_2)_8-SO_3H$; $SF_5-CH_2CHBr-(CH_2)_8-O-SO_3H$
$SF_5-CH_2CHBr-(CH_2)_9-COOH$; $SF_5-CH_2CHBr-(CH_2)_9-SO_3H$; $SF_5-CH_2CHBr-(CH_2)_9-O-SO_3H$
$SF_5-CH_2CHBr-(CH_2)_{10}-COOH$; $SF_5-CH_2CHBr-(CH_2)_{10}-SO_3H$; $SF_5-CH_2CHBr-(CH_2)_{10}-O-SO_3H$
$SF_5-CH_2CHBr-(CH_2)_{11}-COOH$; $SF_5-CH_2CHBr-(CH_2)_{11}-SO_3H$; $SF_5-CH_2CHBr-(CH_2)_{11}-O-SO_3H$
$SF_5-CH_2CHBr-(CH_2)_{12}-COOH$; $SF_5-CH_2CHBr-(CH_2)_{12}-SO_3H$; $SF_5-CH_2CHBr-(CH_2)_{12}-O-SO_3H$
$SF_5-CH_2CHBr-(CH_2)_{13}-COOH$; $SF_5-CH_2CHBr-(CH_2)_{13}-SO_3H$; $SF_5-CH_2CHBr-(CH_2)_{13}-O-SO_3H$
$SF_5-CH_2CHBr-(CH_2)_{14}-COOH$; $SF_5-CH_2CHBr-(CH_2)_{14}-SO_3H$; $SF_5-CH_2CHBr-(CH_2)_{14}-O-SO_3H$
$SF_5-CH_2CHBr-(CH_2)_{15}-COOH$; $SF_5-CH_2CHBr-(CH_2)_{15}-SO_3H$; $SF_5-CH_2CHBr-(CH_2)_{15}-O-SO_3H$
$SF_5-CH_2CHBr-(CH_2)_{16}-COOH$; $SF_5-CH_2CHBr-(CH_2)_{16}-SO_3H$; $SF_5-CH_2CHBr-(CH_2)_{16}-O-SO_3H$
$SF_5-CH_2CHBr-(CH_2)_{17}-COOH$; $SF_5-CH_2CHBr-(CH_2)_{17}-SO_3H$; $SF_5-CH_2CHBr-(CH_2)_{17}-O-SO_3H$
$SF_5-CH_2CHBr-(CH_2)_{18}-COOH$; $SF_5-CH_2CHBr-(CH_2)_{18}-SO_3H$; $SF_5-CH_2CHBr-(CH_2)_{18}-O-SO_3H$
$SF_5-CH_2CHBr-(CH_2)_{19}-COOH$; $SF_5-CH_2CHBr-(CH_2)_{19}-SO_3H$; $SF_5-CH_2CHBr-(CH_2)_{19}-O-SO_3H$
$SF_5-CH_2CHBr-(CH_2)_{20}-COOH$; $SF_5-CH_2CHBr-(CH_2)_{20}-SO_3H$; $SF_5-CH_2CHBr-(CH_2)_{20}-O-SO_3H$
$SF_5-CH_2CHBr-(CH_2)_{21}-COOH$; $SF_5-CH_2CHBr-(CH_2)_{21}-SO_3H$; $SF_5-CH_2CHBr-(CH_2)_{21}-O-SO_3H$
$SF_5-CH_2CHBr-(CH_2)_{22}-COOH$; $SF_5-CH_2CHBr-(CH_2)_{22}-SO_3H$; $SF_5-CH_2CHBr-(CH_2)_{22}-O-SO_3H$
$SF_5-CH_2CHBr-(CH_2)_{23}-COOH$; $SF_5-CH_2CHBr-(CH_2)_{23}-SO_3H$; $SF_5-CH_2CHBr-(CH_2)_{23}-O-SO_3H$
$SF_5-CH_2CHBr-(CH_2)_{24}-COOH$; $SF_5-CH_2CHBr-(CH_2)_{24}-SO_3H$; $SF_5-CH_2CHBr-(CH_2)_{24}-O-SO_3H$
$CF_3-O-(CH_2)_4-OH$; $CF_3-O-(CH_2)_4-(OCH_2CH_2)_m-OH$; $CF_3-O-(CH_2)_4-(OCH_2CH_2)_m-SO_2-CH=CH_2$
$CF_3-O-(CH_2)_5-OH$; $CF_3-O-(CH_2)_5-(OCH_2CH_2)_m-OH$; $CF_3-O-(CH_2)_5-(OCH_2CH_2)_m-SO_2-CH=CH_2$
$CF_3-O-(CH_2)_6-OH$; $CF_3-O-(CH_2)_6-(OCH_2CH_2)_m-OH$; $CF_3-O-(CH_2)_6-(OCH_2CH_2)_m-SO_2-CH=CH_2$
$CF_3-O-(CH_2)_7-OH$; $CF_3-O-(CH_2)_7-(OCH_2CH_2)_m-OH$; $CF_3-O-(CH_2)_7-(OCH_2CH_2)_m-SO_2-CH=CH_2$
$CF_3-O-(CH_2)_8-OH$; $CF_3-O-(CH_2)_8-(OCH_2CH_2)_m-OH$; $CF_3-O-(CH_2)_8-(OCH_2CH_2)_m-SO_2-CH=CH_2$
$CF_3-O-(CH_2)_9-OH$; $CF_3-O-(CH_2)_9-(OCH_2CH_2)_m-OH$; $CF_3-O-(CH_2)_9-(OCH_2CH_2)_m-SO_2-CH=CH_2$
$CF_3-O-(CH_2)_{10}-OH$; $CF_3-O-(CH_2)_{10}-(OCH_2CH_2)_m-OH$; $CF_3-O-(CH_2)_{10}-(OCH_2CH_2)_m-SO_2-CH=CH_2$
$CF_3-O-(CH_2)_{11}-OH$; $CF_3-O-(CH_2)_{11}-(OCH_2CH_2)_m-OH$; $CF_3-O-(CH_2)_{11}-(OCH_2CH_2)_m-SO_2-CH=CH_2$
$CF_3-O-(CH_2)_{12}-OH$; $CF_3-O-(CH_2)_{12}-(OCH_2CH_2)_m-OH$; $CF_3-O-(CH_2)_{12}-(OCH_2CH_2)_m-SO_2-CH=CH_2$
$CF_3-O-(CH_2)_{13}-OH$; $CF_3-O-(CH_2)_{13}-(OCH_2CH_2)_m-OH$; $CF_3-O-(CH_2)_{13}-(OCH_2CH_2)_m-SO_2-CH=CH_2$
$CF_3-O-(CH_2)_{14}-OH$; $CF_3-O-(CH_2)_{14}-(OCH_2CH_2)_m-OH$; $CF_3-O-(CH_2)_{14}-(OCH_2CH_2)_m-SO_2-CH=CH_2$
$CF_3-O-(CH_2)_{15}-OH$; $CF_3-O-(CH_2)_{15}-(OCH_2CH_2)_m-OH$; $CF_3-O-(CH_2)_{15}-(OCH_2CH_2)_m-SO_2-CH=CH_2$ -continued $CF_3-O-(CH_2)_{16}-OH$; $CF_3-O-(CH_2)_{16}-(OCH_2CH_2)_m-OH$; $CF_3-O-(CH_2)_{16}-(OCH_2CH_2)_m-SO_2-CH=CH_2$
$CF_3-O-(CH_2)_{17}-OH$; $CF_3-O-(CH_2)_{17}-(OCH_2CH_2)_m-OH$; $CF_3-O-(CH_2)_{17}-(OCH_2CH_2)_m-SO_2-CH=CH_2$
$CF_3-O-(CH_2)_{18}-OH$; $CF_3-O-(CH_2)_{18}-(OCH_2CH_2)_m-OH$; $CF_3-O-(CH_2)_{18}-(OCH_2CH_2)_m-SO_2-CH=CH_2$
$CF_3-O-(CH_2)_{19}-OH$; $CF_3-O-(CH_2)_{19}-(OCH_2CH_2)_m-OH$; $CF_3-O-(CH_2)_{19}-(OCH_2CH_2)_m-SO_2-CH=CH_2$
$CF_3-O-(CH_2)_{20}-OH$; $CF_3-O-(CH_2)_{20}-(OCH_2CH_2)_m-OH$; $CF_3-O-(CH_2)_{20}-(OCH_2CH_2)_m-SO_2-CH=CH_2$
$CF_3-O-(CH_2)_{21}-OH$; $CF_3-O-(CH_2)_{21}-(OCH_2CH_2)_m-OH$; $CF_3-O-(CH_2)_{21}-(OCH_2CH_2)_m-SO_2-CH=CH_2$
$CF_3-O-(CH_2)_{22}-OH$; $CF_3-O-(CH_2)_{22}-(OCH_2CH_2)_m-OH$; $CF_3-O-(CH_2)_{22}-(OCH_2CH_2)_m-SO_2-CH=CH_2$
$CF_3-O-(CH_2)_{23}-OH$; $CF_3-O-(CH_2)_{23}-(OCH_2CH_2)_m-OH$; $CF_3-O-(CH_2)_{23}-(OCH_2CH_2)_m-SO_2-CH=CH_2$
$CF_3-O-(CH_2)_{24}-OH$; $CF_3-O-(CH_2)_{24}-(OCH_2CH_2)_m-OH$; $CF_3-O-(CH_2)_{24}-(OCH_2CH_2)_m-SO_2-CH=CH_2$
$SF_5-(CH_2)_4-OH$; $SF_5-(CH_2)_4-(OCH_2CH_2)_m-OH$; $SF_5-(CH_2)_4-(OCH_2CH_2)_m-SO_2-CH=CH_2$
$SF_5-(CH_2)_5-OH$; $SF_5-(CH_2)_5-(OCH_2CH_2)_m-OH$; $SF_5-(CH_2)_5-(OCH_2CH_2)_m-SO_2-CH=CH_2$
$SF_5-(CH_2)_6-OH$; $SF_5-(CH_2)_6-(OCH_2CH_2)_m-OH$; $SF_5-(CH_2)_6-(OCH_2CH_2)_m-SO_2-CH=CH_2$
$SF_5-(CH_2)_7-OH$; $SF_5-(CH_2)_7-(OCH_2CH_2)_m-OH$; $SF_5-(CH_2)_7-(OCH_2CH_2)_m-SO_2-CH=CH_2$
$SF_5-(CH_2)_8-OH$; $SF_5-(CH_2)_8-(OCH_2CH_2)_m-OH$; $SF_5-(CH_2)_8-(OCH_2CH_2)_m-SO_2-CH=CH_2$
$SF_5-(CH_2)_9-OH$; $SF_5-(CH_2)_9-(OCH_2CH_2)_m-OH$; $SF_5-(CH_2)_9-(OCH_2CH_2)_m-SO_2-CH=CH_2$
$SF_5-(CH_2)_{10}-OH$; $SF_5-(CH_2)_{10}-(OCH_2CH_2)_m-OH$; $SF_5-(CH_2)_{10}-(OCH_2CH_2)_m-SO_2-CH=CH_2$
$SF_5-(CH_2)_{11}-OH$; $SF_5-(CH_2)_{11}-(OCH_2CH_2)_m-OH$; $SF_5-(CH_2)_{11}-(OCH_2CH_2)_m-SO_2-CH=CH_2$
$SF_5-(CH_2)_{12}-OH$; $SF_5-(CH_2)_{12}-(OCH_2CH_2)_m-OH$; $SF_5-(CH_2)_{12}-(OCH_2CH_2)_m-SO_2-CH=CH_2$
$SF_5-(CH_2)_{13}-OH$; $SF_5-(CH_2)_{13}-(OCH_2CH_2)_m-OH$; $SF_5-(CH_2)_{13}-(OCH_2CH_2)_m-SO_2-CH=CH_2$
$SF_5-(CH_2)_{14}-OH$; $SF_5-(CH_2)_{14}-(OCH_2CH_2)_m-OH$; $SF_5-(CH_2)_{14}-(OCH_2CH_2)_m-SO_2-CH=CH_2$
$SF_5-(CH_2)_{15}-OH$; $SF_5-(CH_2)_{15}-(OCH_2CH_2)_m-OH$; $SF_5-(CH_2)_{15}-(OCH_2CH_2)_m-SO_2-CH=CH_2$
$SF_5-(CH_2)_{16}-OH$; $SF_5-(CH_2)_{16}-(OCH_2CH_2)_m-OH$; $SF_5-(CH_2)_{16}-(OCH_2CH_2)_m-SO_2-CH=CH_2$
$SF_5-(CH_2)_{17}-OH$; $SF_5-(CH_2)_{17}-(OCH_2CH_2)_m-OH$; $SF_5-(CH_2)_{17}-(OCH_2CH_2)_m-SO_2-CH=CH_2$
$SF_5-(CH_2)_{18}-OH$; $SF_5-(CH_2)_{18}-(OCH_2CH_2)_m-OH$; $SF_5-(CH_2)_{18}-(OCH_2CH_2)_m-SO_2-CH=CH_2$
$SF_5-(CH_2)_{19}-OH$; $SF_5-(CH_2)_{19}-(OCH_2CH_2)_m-OH$; $SF_5-(CH_2)_{19}-(OCH_2CH_2)_m-SO_2-CH=CH_2$
$SF_5-(CH_2)_{20}-OH$; $SF_5-(CH_2)_{20}-(OCH_2CH_2)_m-OH$; $SF_5-(CH_2)_{20}-(OCH_2CH_2)_m-SO_2-CH=CH_2$
$SF_5-(CH_2)_{21}-OH$; $SF_5-(CH_2)_{21}-(OCH_2CH_2)_m-OH$; $SF_5-(CH_2)_{21}-(OCH_2CH_2)_m-SO_2-CH=CH_2$
$SF_5-(CH_2)_{22}-OH$; $SF_5-(CH_2)_{22}-(OCH_2CH_2)_m-OH$; $SF_5-(CH_2)_{22}-(OCH_2CH_2)_m-SO_2-CH=CH_2$
$SF_5-(CH_2)_{23}-OH$; $SF_5-(CH_2)_{23}-(OCH_2CH_2)_m-OH$; $SF_5-(CH_2)_{23}-(OCH_2CH_2)_m-SO_2-CH=CH_2$
$SF_5-(CH_2)_{24}-OH$; $SF_5-(CH_2)_{24}-(OCH_2CH_2)_m-OH$; $SF_5-(CH_2)_{24}-(OCH_2CH_2)_m-SO_2-CH=CH_2$
$SF_5-CH=CH-(CH_2)_4-OH$; $SF_5-CH=CH-(CH_2)_4-(OCH_2CH_2)_m-OH$; $SF_5-CH=CH-(CH_2)_4-(OCH_2CH_2)_m-SO_2-CH=CH_2$
$SF_5-CH=CH-(CH_2)_5-OH$; $SF_5-CH=CH-(CH_2)_5-(OCH_2CH_2)_m-OH$; $SF_5-CH=CH-(CH_2)_5-(OCH_2CH_2)_m-SO_2-CH=CH_2$
$SF_5-CH=CH-(CH_2)_6-OH$; $SF_5-CH=CH-(CH_2)_6-(OCH_2CH_2)_m-OH$; $SF_5-CH=CH-(CH_2)_6-(OCH_2CH_2)_m-SO_2-CH=CH_2$
$SF_5-CH=CH-(CH_2)_7-OH$; $SF_5-CH=CH-(CH_2)_7-(OCH_2CH_2)_m-OH$; $SF_5-CH=CH-(CH_2)_7-(OCH_2CH_2)_m-SO_2-CH=CH_2$
$SF_5-CH=CH-(CH_2)_8-OH$; $SF_5-CH=CH-(CH_2)_8-(OCH_2CH_2)_m-OH$; $SF_5-CH=CH-(CH_2)_8-(OCH_2CH_2)_m-SO_2-CH=CH_2$
$SF_5-CH=CH-(CH_2)_9-OH$; $SF_5-CH=CH-(CH_2)_9-(OCH_2CH_2)_m-OH$; $SF_5-CH=CH-(CH_2)_9-(OCH_2CH_2)_m-SO_2-CH=CH_2$
$SF_5-CH=CH-(CH_2)_{10}-OH$; $SF_5-CH=CH-(CH_2)_{10}-(OCH_2CH_2)_m-OH$; $SF_5-CH=CH-(CH_2)_{10}-(OCH_2CH_2)_m-SO_2-CH=CH_2$
$SF_5-CH=CH-(CH_2)_{11}-OH$; $SF_5-CH=CH-(CH_2)_{11}-(OCH_2CH_2)_m-OH$; $SF_5-CH=CH-(CH_2)_{11}-(OCH_2CH_2)_m-SO_2-CH=CH_2$
$SF_5-CH=CH-(CH_2)_{12}-OH$; $SF_5-CH=CH-(CH_2)_{12}-(OCH_2CH_2)_m-OH$; $SF_5-CH=CH-(CH_2)_{12}-(OCH_2CH_2)_m-SO_2-CH=CH_2$
$SF_5-CH=CH-(CH_2)_{13}-OH$; $SF_5-CH=CH-(CH_2)_{13}-(OCH_2CH_2)_m-OH$; $SF_5-CH=CH-(CH_2)_{13}-(OCH_2CH_2)_m-SO_2-CH=CH_2$
$SF_5-CH=CH-(CH_2)_{14}-OH$; $SF_5-CH=CH-(CH_2)_{14}-(OCH_2CH_2)_m-OH$; $SF_5-CH=CH-(CH_2)_{14}-(OCH_2CH_2)_m-SO_2-CH=CH_2$
$SF_5-CH=CH-(CH_2)_{15}-OH$; $SF_5-CH=CH-(CH_2)_{15}-(OCH_2CH_2)_m-OH$; $SF_5-CH=CH-(CH_2)_{15}-(OCH_2CH_2)_m-SO_2-CH=CH_2$
$SF_5-CH=CH-(CH_2)_{16}-OH$; $SF_5-CH=CH-(CH_2)_{16}-(OCH_2CH_2)_m-OH$; $SF_5-CH=CH-(CH_2)_{16}-(OCH_2CH_2)_m-SO_2-CH=CH_2$
$SF_5-CH=CH-(CH_2)_{17}-OH$; $SF_5-CH=CH-(CH_2)_{17}-(OCH_2CH_2)_m-OH$; $SF_5-CH=CH-(CH_2)_{17}-(OCH_2CH_2)_m-SO_2-CH=CH_2$
$SF_5-CH=CH-(CH_2)_{18}-OH$; $SF_5-CH=CH-(CH_2)_{18}-(OCH_2CH_2)_m-OH$; $SF_5-CH=CH-(CH_2)_{18}-(OCH_2CH_2)_m-SO_2-CH=CH_2$
$SF_5-CH=CH-(CH_2)_{19}-OH$; $SF_5-CH=CH-(CH_2)_{19}-(OCH_2CH_2)_m-OH$; $SF_5-CH=CH-(CH_2)_{19}-(OCH_2CH_2)_m-SO_2-CH=CH_2$
$SF_5-CH=CH-(CH_2)_{20}-OH$; $SF_5-CH=CH-(CH_2)_{20}-(OCH_2CH_2)_m-OH$; $SF_5-CH=CH-(CH_2)_{20}-(OCH_2CH_2)_m-SO_2-CH=CH_2$
$SF_5-CH=CH-(CH_2)_{21}-OH$; $SF_5-CH=CH-(CH_2)_{21}-(OCH_2CH_2)_m-OH$; $SF_5-CH=CH-(CH_2)_{21}-(OCH_2CH_2)_m-SO_2-CH=CH_2$
$SF_5-CH=CH-(CH_2)_{22}-OH$; $SF_5-CH=CH-(CH_2)_{22}-(OCH_2CH_2)_m-OH$; $SF_5-CH=CH-(CH_2)_{22}-(OCH_2CH_2)_m-SO_2-CH=CH_2$
$SF_5-CH=CH-(CH_2)_{23}-OH$; $SF_5-CH=CH-(CH_2)_{23}-(OCH_2CH_2)_m-OH$; $SF_5-CH=CH-(CH_2)_{23}-(OCH_2CH_2)_m-SO_2-CH=CH_2$
$SF_5-CH=CH-(CH_2)_{24}-OH$; $SF_5-CH=CH-(CH_2)_{24}-(OCH_2CH_2)_m-OH$; $SF_5-CH=CH-(CH_2)_{24}-(OCH_2CH_2)_m-SO_2-CH=CH_2$
$SF_5-CH_2CHBr-(CH_2)_4-OH$; $SF_5-CH_2CHBr-(CH_2)_4-(OCH_2CH_2)_m-OH$; $SF_5-CH_2CHBr-(CH_2)_4-(OCH_2CH_2)_m-SO_2-CH=CH_2$
$SF_5-CH_2CHBr-(CH_2)_5-OH$; $SF_5-CH_2CHBr-(CH_2)_5-(OCH_2CH_2)_m-OH$; $SF_5-CH_2CHBr-(CH_2)_5-(OCH_2CH_2)_m-SO_2-CH=CH_2$
$SF_5-CH_2CHBr-(CH_2)_6-OH$; $SF_5-CH_2CHBr-(CH_2)_6-(OCH_2CH_2)_m-OH$; $SF_5-CH_2CHBr-(CH_2)_6-(OCH_2CH_2)_m-SO_2-CH=CH_2$
$SF_5-CH_2CHBr-(CH_2)_7-OH$; $SF_5-CH_2CHBr-(CH_2)_7-(OCH_2CH_2)_m-OH$; $SF_5-CH_2CHBr-(CH_2)_7-(OCH_2CH_2)_m-SO_2-CH=CH_2$
$SF_5-CH_2CHBr-(CH_2)_8-OH$; $SF_5-CH_2CHBr-(CH_2)_8-(OCH_2CH_2)_m-OH$; $SF_5-CH_2CHBr-(CH_2)_8-(OCH_2CH_2)_m-SO_2-CH=CH_2$
$SF_5-CH_2CHBr-(CH_2)_9-OH$; $SF_5-CH_2CHBr-(CH_2)_9-(OCH_2CH_2)_m-OH$; $SF_5-CH_2CHBr-(CH_2)_9-(OCH_2CH_2)_m-SO_2-CH=CH_2$
$SF_5-CH_2CHBr-(CH_2)_{10}-OH$; $SF_5-CH_2CHBr-(CH_2)_{10}-(OCH_2CH_2)_m-OH$; $SF_5-CH_2CHBr-(CH_2)_{10}-(OCH_2CH_2)_m-SO_2-CH=CH_2$
$SF_5-CH_2CHBr-(CH_2)_{11}-OH$; $SF_5-CH_2CHBr-(CH_2)_{11}-(OCH_2CH_2)_m-OH$; $SF_5-CH_2CHBr-(CH_2)_{11}-(OCH_2CH_2)_m-SO_2-CH=CH_2$
$SF_5-CH_2CHBr-(CH_2)_{12}-OH$; $SF_5-CH_2CHBr-(CH_2)_{12}-(OCH_2CH_2)_m-OH$; $SF_5-CH_2CHBr-(CH_2)_{12}-(OCH_2CH_2)_m-SO_2-CH=CH_2$
$SF_5-CH_2CHBr-(CH_2)_{13}-OH$; $SF_5-CH_2CHBr-(CH_2)_{13}-(OCH_2CH_2)_m-OH$; $SF_5-CH_2CHBr-(CH_2)_{13}-(OCH_2CH_2)_m-SO_2-CH=CH_2$
$SF_5-CH_2CHBr-(CH_2)_{14}-OH$; $SF_5-CH_2CHBr-(CH_2)_{14}-(OCH_2CH_2)_m-OH$; $SF_5-CH_2CHBr-(CH_2)_{14}-(OCH_2CH_2)_m-SO_2-CH=CH_2$
$SF_5-CH_2CHBr-(CH_2)_{15}-OH$; $SF_5-CH_2CHBr-(CH_2)_{15}-(OCH_2CH_2)_m-OH$; $SF_5-CH_2CHBr-(CH_2)_{15}-(OCH_2CH_2)_m-SO_2-CH=CH_2$
$SF_5-CH_2CHBr-(CH_2)_{16}-OH$; $SF_5-CH_2CHBr-(CH_2)_{16}-(OCH_2CH_2)_m-OH$; $SF_5-CH_2CHBr-(CH_2)_{16}-(OCH_2CH_2)_m-SO_2-CH=CH_2$
$SF_5-CH_2CHBr-(CH_2)_{17}-OH$; $SF_5-CH_2CHBr-(CH_2)_{17}-(OCH_2CH_2)_m-OH$; $SF_5-CH_2CHBr-(CH_2)_{17}-(OCH_2CH_2)_m-SO_2-CH=CH_2$
$SF_5-CH_2CHBr-(CH_2)_{18}-OH$; $SF_5-CH_2CHBr-(CH_2)_{18}-(OCH_2CH_2)_m-OH$; $SF_5-CH_2CHBr-(CH_2)_{18}-(OCH_2CH_2)_m-SO_2-CH=CH_2$
$SF_5-CH_2CHBr-(CH_2)_{19}-OH$; $SF_5-CH_2CHBr-(CH_2)_{19}-(OCH_2CH_2)_m-OH$; $SF_5-CH_2CHBr-(CH_2)_{19}-(OCH_2CH_2)_m-SO_2-CH=CH_2$
$SF_5-CH_2CHBr-(CH_2)_{20}-OH$; $SF_5-CH_2CHBr-(CH_2)_{20}-(OCH_2CH_2)_m-OH$; $SF_5-CH_2CHBr-(CH_2)_{20}-(OCH_2CH_2)_m-SO_2-CH=CH_2$
$SF_5-CH_2CHBr-(CH_2)_{21}-OH$; $SF_5-CH_2CHBr-(CH_2)_{21}-(OCH_2CH_2)_m-OH$; $SF_5-CH_2CHBr-(CH_2)_{21}-(OCH_2CH_2)_m-SO_2-CH=CH_2$
$SF_5-CH_2CHBr-(CH_2)_{22}-OH$; $SF_5-CH_2CHBr-(CH_2)_{22}-(OCH_2CH_2)_m-OH$; $SF_5-CH_2CHBr-(CH_2)_{22}-(OCH_2CH_2)_m-SO_2-CH=CH_2$
$SF_5-CH_2CHBr-(CH_2)_{23}-OH$; $SF_5-CH_2CHBr-(CH_2)_{23}-(OCH_2CH_2)_m-OH$; $SF_5-CH_2CHBr-(CH_2)_{23}-(OCH_2CH_2)_m-SO_2-CH=CH_2$
$SF_5-CH_2CHBr-(CH_2)_{24}-OH$; $SF_5-CH_2CHBr-(CH_2)_{24}-(OCH_2CH_2)_m-OH$; $SF_5-CH_2CHBr-(CH_2)_{24}-(OCH_2CH_2)_m-SO_2-CH=CH_2$
$CF_3-O-(CH_2)_4-(OCH_2CH_2)_m-OCOCH=CH_2$; $CF_3-O-(CH_2)_4-(OCH_2CH_2)_m-OCH=CH_2$; $CF_3-O-(CH_2)_4-(OCH_2CH_2)_m-OAr(NCO)_p$
$CF_3-O-(CH_2)_5-(OCH_2CH_2)_m-OCOCH=CH_2$; $CF_3-O-(CH_2)_5-(OCH_2CH_2)_m-OCH=CH_2$; $CF_3-O-(CH_2)_5-(OCH_2CH_2)_m-OAr(NCO)_p$
$CF_3-O-(CH_2)_6-(OCH_2CH_2)_m-OCOCH=CH_2$; $CF_3-O-(CH_2)_6-(OCH_2CH_2)_m-OCH=CH_2$; $CF_3-O-(CH_2)_6-(OCH_2CH_2)_m-OAr(NCO)_p$
$CF_3-O-(CH_2)_7-(OCH_2CH_2)_m-OCOCH=CH_2$; $CF_3-O-(CH_2)_7-(OCH_2CH_2)_m-OCH=CH_2$;
$CF_3-O-(CH_2)_7-(OCH_2CH_2)_m-OAr(NCO)_p$
$CF_3-O-(CH_2)_8-(OCH_2CH_2)_m-OCOCH=CH_2$; $CF_3-O-(CH_2)_8-(OCH_2CH_2)_m-OCH=CH_2$;
$CF_3-O-(CH_2)_8-(OCH_2CH_2)_m-OAr(NCO)_p$
$CF_3-O-(CH_2)_9-(OCH_2CH_2)_m-OCOCH=CH_2$; $CF_3-O-(CH_2)_9-(OCH_2CH_2)_m-OCH=CH_2$;

-continued $CF_3-O-(CH_2)_9-(OCH_2CH_2)_m-OAr(NCO)_p$
$CF_3-O-(CH_2)_{10}-(OCH_2CH_2)_m-OCOCH=CH_2$; $CF_3-O-(CH_2)_{10}-(OCH_2CH_2)_m-OCH=CH_2$;
$CF_3-O-(CH_2)_{10}-(OCH_2CH_2)_m-OAr(NCO)_p$
$CF_3-O-(CH_2)_{11}-(OCH_2CH_2)_m-OCOCH=CH_2$; $CF_3-O-(CH_2)_{11}-(OCH_2CH_2)_m-OCH=CH_2$;
$CF_3-O-(CH_2)_{11}-(OCH_2CH_2)_m-OAr(NCO)_p$
$CF_3-O-(CH_2)_{12}-(OCH_2CH_2)_m-OCOCH=CH_2$; $CF_3-O-(CH_2)_{12}-(OCH_2CH_2)_m-OCH=CH_2$;
$CF_3-O-(CH_2)_{12}-(OCH_2CH_2)_m-OAr(NCO)_p$
$CF_3-O-(CH_2)_{13}-(OCH_2CH_2)_m-OCOCH=CH_2$; $CF_3-O-(CH_2)_{13}-(OCH_2CH_2)_m-OCH=CH_2$;
$CF_3-O-(CH_2)_{13}-(OCH_2CH_2)_m-OAr(NCO)_p$
$CF_3-O-(CH_2)_{14}-(OCH_2CH_2)_m-OCOCH=CH_2$; $CF_3-O-(CH_2)_{14}-(OCH_2CH_2)_m-OCH=CH_2$;
$CF_3-O-(CH_2)_{14}-(OCH_2CH_2)_m-OAr(NCO)_p$
$CF_3-O-(CH_2)_{15}-(OCH_2CH_2)_m-OCOCH=CH_2$; $CF_3-O-(CH_2)_{15}-(OCH_2CH_2)_m-OCH=CH_2$;
$CF_3-O-(CH_2)_{15}-(OCH_2CH_2)_m-OAr(NCO)_p$
$CF_3-O-(CH_2)_{16}-(OCH_2CH_2)_m-OCOCH=CH_2$; $CF_3-O-(CH_2)_{16}-(OCH_2CH_2)_m-OCH=CH_2$;
$CF_3-O-(CH_2)_{16}-(OCH_2CH_2)_m-OAr(NCO)_p$
$CF_3-O-(CH_2)_{17}-(OCH_2CH_2)_m-OCOCH=CH_2$; $CF_3-O-(CH_2)_{17}-(OCH_2CH_2)_m-OCH=CH_2$;
$CF_3-O-(CH_2)_{17}-(OCH_2CH_2)_m-OAr(NCO)_p$
$CF_3-O-(CH_2)_{18}-(OCH_2CH_2)_m-OCOCH=CH_2$; $CF_3-O-(CH_2)_{18}-(OCH_2CH_2)_m-OCH=CH_2$;
$CF_3-O-(CH_2)_{18}-(OCH_2CH_2)_m-OAr(NCO)_p$
$CF_3-O-(CH_2)_{19}-(OCH_2CH_2)_m-OCOCH=CH_2$; $CF_3-O-(CH_2)_{19}-(OCH_2CH_2)_m-OCH=CH_2$;
$CF_3-O-(CH_2)_{19}-(OCH_2CH_2)_m-OAr(NCO)_p$
$CF_3-O-(CH_2)_{20}-(OCH_2CH_2)_m-OCOCH=CH_2$; $CF_3-O-(CH_2)_{20}-(OCH_2CH_2)_m-OCH=CH_2$;
$CF_3-O-(CH_2)_{20}-(OCH_2CH_2)_m-OAr(NCO)_p$
$CF_3-O-(CH_2)_{21}-(OCH_2CH_2)_m-OCOCH=CH_2$; $CF_3-O-(CH_2)_{21}-(OCH_2CH_2)_m-OCH=CH_2$;
$CF_3-O-(CH_2)_{21}-(OCH_2CH_2)_m-OAr(NCO)_p$
$CF_3-O-(CH_2)_{22}-(OCH_2CH_2)_m-OCOCH=CH_2$; $CF_3-O-(CH_2)_{22}-(OCH_2CH_2)_m-OCH=CH_2$;
$CF_3-O-(CH_2)_{22}-(OCH_2CH_2)_m-OAr(NCO)_p$
$CF_3-O-(CH_2)_{23}-(OCH_2CH_2)_m-OCOCH=CH_2$; $CF_3-O-(CH_2)_{23}-(OCH_2CH_2)_m-OCH=CH_2$;
$CF_3-O-(CH_2)_{23}-(OCH_2CH_2)_m-OAr(NCO)_p$
$CF_3-O-(CH_2)_{24}-(OCH_2CH_2)_m-OCOCH=CH_2$; $CF_3-O-(CH_2)_{24}-(OCH_2CH_2)_m-OCH=CH_2$;
$CF_3-O-(CH_2)_{24}-(OCH_2CH_2)_m-OAr(NCO)_p$
$SF_5-(CH_2)_4-(OCH_2CH_2)_m-OCOCH=CH_2$; $SF_5-(CH_2)_4-(OCH_2CH_2)_m-OCH=CH_2$;
$SF_5-(CH_2)_4-(OCH_2CH_2)_m-OAr(NCO)_p$
$SF_5-(CH_2)_5-(OCH_2CH_2)_m-OCOCH=CH_2$; $SF_5-(CH_2)_5-(OCH_2CH_2)_m-OCH=CH_2$;
$SF_5-(CH_2)_5-(OCH_2CH_2)_m-OAr(NCO)_p$
$SF_5-(CH_2)_6-(OCH_2CH_2)_m-OCOCH=CH_2$; $SF_5-(CH_2)_6-(OCH_2CH_2)_m-OCH=CH_2$;
$SF_5-(CH_2)_6-(OCH_2CH_2)_m-OAr(NCO)_p$
$SF_5-(CH_2)_7-(OCH_2CH_2)_m-OCOCH=CH_2$; $SF_5-(CH_2)_7-(OCH_2CH_2)_m-OCH=CH_2$;
$SF_5-(CH_2)_7-(OCH_2CH_2)_m-OAr(NCO)_p$
$SF_5-(CH_2)_8-(OCH_2CH_2)_m-OCOCH=CH_2$; $SF_5-(CH_2)_8-(OCH_2CH_2)_m-OCH=CH_2$;
$SF_5-(CH_2)_8-(OCH_2CH_2)_m-OAr(NCO)_p$
$SF_5-(CH_2)_9-(OCH_2CH_2)_m-OCOCH=CH_2$; $SF_5-(CH_2)_9-(OCH_2CH_2)_m-OCH=CH_2$;
$SF_5-(CH_2)_9-(OCH_2CH_2)_m-OAr(NCO)_p$
$SF_5-(CH_2)_{10}-(OCH_2CH_2)_m-OCOCH=CH_2$; $SF_5-(CH_2)_{10}-(OCH_2CH_2)_m-OCH=CH_2$;
$SF_5-(CH_2)_{10}-(OCH_2CH_2)_m-OAr(NCO)_p$
$SF_5-(CH_2)_{11}-(OCH_2CH_2)_m-OCOCH=CH_2$; $SF_5-(CH_2)_{11}-(OCH_2CH_2)_m-OCH=CH_2$;
$SF_5-(CH_2)_{11}-(OCH_2CH_2)_m-OAr(NCO)_p$
$SF_5-(CH_2)_{12}-(OCH_2CH_2)_m-OCOCH=CH_2$; $SF_5-(CH_2)_{12}-(OCH_2CH_2)_m-OCH=CH_2$;
$SF_5-(CH_2)_{12}-(OCH_2CH_2)_m-OAr(NCO)_p$
$SF_5-(CH_2)_{13}-(OCH_2CH_2)_m-OCOCH=CH_2$; $SF_5-(CH_2)_{13}-(OCH_2CH_2)_m-OCH=CH_2$;
$SF_5-(CH_2)_{13}-(OCH_2CH_2)_m-OAr(NCO)_p$
$SF_5-(CH_2)_{14}-(OCH_2CH_2)_m-OCOCH=CH_2$; $SF_5-(CH_2)_{14}-(OCH_2CH_2)_m-OCH=CH_2$;
$SF_5-(CH_2)_{14}-(OCH_2CH_2)_m-OAr(NCO)_p$
$SF_5-(CH_2)_{15}-(OCH_2CH_2)_m-OCOCH=CH_2$; $SF_5-(CH_2)_{15}-(OCH_2CH_2)_m-OCH=CH_2$;
$SF_5-(CH_2)_{15}-(OCH_2CH_2)_m-OAr(NCO)_p$
$SF_5-(CH_2)_{16}-(OCH_2CH_2)_m-OCOCH=CH_2$; $SF_5-(CH_2)_{16}-(OCH_2CH_2)_m-OCH=CH_2$;
$SF_5-(CH_2)_{16}-(OCH_2CH_2)_m-OAr(NCO)_p$
$SF_5-(CH_2)_{17}-(OCH_2CH_2)_m-OCOCH=CH_2$; $SF_5-(CH_2)_{17}-(OCH_2CH_2)_m-OCH=CH_2$;
$SF_5-(CH_2)_{17}-(OCH_2CH_2)_m-OAr(NCO)_p$
$SF_5-(CH_2)_{18}-(OCH_2CH_2)_m-OCOCH=CH_2$; $SF_5-(CH_2)_{18}-(OCH_2CH_2)_m-OCH=CH_2$;
$SF_5-(CH_2)_{18}-(OCH_2CH_2)_m-OAr(NCO)_p$
$SF_5-(CH_2)_{19}-(OCH_2CH_2)_m-OCOCH=CH_2$; $SF_5-(CH_2)_{19}-(OCH_2CH_2)_m-OCH=CH_2$;
$SF_5-(CH_2)_{19}-(OCH_2CH_2)_m-OAr(NCO)_p$
$SF_5-(CH_2)_{20}-(OCH_2CH_2)_m-OCOCH=CH_2$; $SF_5-(CH_2)_{20}-(OCH_2CH_2)_m-OCH=CH_2$;
$SF_5-(CH_2)_{20}-(OCH_2CH_2)_m-OAr(NCO)_p$
$SF_5-(CH_2)_{21}-(OCH_2CH_2)_m-OCOCH=CH_2$; $SF_5-(CH_2)_{21}-(OCH_2CH_2)_m-OCH=CH_2$;
$SF_5-(CH_2)_{21}-(OCH_2CH_2)_m-OAr(NCO)_p$
$SF_5-(CH_2)_{22}-(OCH_2CH_2)_m-OCOCH=CH_2$; $SF_5-(CH_2)_{22}-(OCH_2CH_2)_m-OCH=CH_2$;
$SF_5-(CH_2)_{22}-(OCH_2CH_2)_m-OAr(NCO)_p$
$SF_5-(CH_2)_{23}-(OCH_2CH_2)_m-OCOCH=CH_2$; $SF_5-(CH_2)_{23}-(OCH_2CH_2)_m-OCH=CH_2$;
$SF_5-(CH_2)_{23}-(OCH_2CH_2)_m-OAr(NCO)_p$
$SF_5-(CH_2)_{24}-(OCH_2CH_2)_m-OCOCH=CH_2$; $SF_5-(CH_2)_{24}-(OCH_2CH_2)_m-OCH=CH_2$;
$SF_5-(CH_2)_{24}-(OCH_2CH_2)_m-OAr(NCO)_p$
$SF_5-CH=CH-(CH_2)_4-(OCH_2CH_2)_m-OCOCH=CH_2$; $SF_5-CH=CH-(CH_2)_4-(OCH_2CH_2)_m-OCH=CH_2$;
$SF_5-CH=CH-(CH_2)_4-(OCH_2CH_2)_m-OAr(NCO)_p$
$SF_5-CH=CH-(CH_2)_5-(OCH_2CH_2)_m-OCOCH=CH_2$; $SF_5-CH=CH-(CH_2)_5-(OCH_2CH_2)_m-OCH=CH_2$;
$SF_5-CH=CH-(CH_2)_5-(OCH_2CH_2)_m-OAr(NCO)_p$
$SF_5-CH=CH-(CH_2)_6-(OCH_2CH_2)_m-OCOCH=CH_2$; $SF_5-CH=CH-(CH_2)_6-(OCH_2CH_2)_m-OCH=CH_2$;
$SF_5-CH=CH-(CH_2)_6-(OCH_2CH_2)_m-OAr(NCO)_p$
$SF_5-CH=CH-(CH_2)_7-(OCH_2CH_2)_m-OCOCH=CH_2$; $SF_5-CH=CH-(CH_2)_7-(OCH_2CH_2)_m-OCH=CH_2$;

-continued $SF_5$—CH=CH—$(CH_2)_7$—$(OCH_2CH_2)_m$—OAr(NCO)$_p$
$SF_5$—CH=CH—$(CH_2)_8$—$(OCH_2CH_2)_m$—OCOCH=$CH_2$; $SF_5$—CH=CH—$(CH_2)_8$—$(OCH_2CH_2)_m$—OCH=$CH_2$;
$SF_5$—CH=CH—$(CH_2)_8$—$(OCH_2CH_2)_m$—OAr(NCO)$_p$
$SF_5$—CH=CH—$(CH_2)_9$—$(OCH_2CH_2)_m$—OCOCH=$CH_2$; $SF_5$—CH=CH—$(CH_2)_9$—$(OCH_2CH_2)_m$—OCH=$CH_2$;
$SF_5$—CH=CH—$(CH_2)_9$—$(OCH_2CH_2)_m$—OAr(NCO)$_p$
$SF_5$—CH=CH—$(CH_2)_{10}$—$(OCH_2CH_2)_m$—OCOCH=$CH_2$; $SF_5$—CH=CH—$(CH_2)_{10}$—$(OCH_2CH_2)_m$—OCH=$CH_2$;
$SF_5$—CH=CH—$(CH_2)_{10}$—$(OCH_2CH_2)_m$—OAr(NCO)$_p$
$SF_5$—CH=CH—$(CH_2)_{11}$—$(OCH_2CH_2)_m$—OCOCH=$CH_2$; $SF_5$—CH=CH—$(CH_2)_{11}$—$(OCH_2CH_2)_m$—OCH=$CH_2$;
$SF_5$—CH=CH—$(CH_2)_{11}$—$(OCH_2CH_2)_m$—OAr(NCO)$_p$
$SF_5$—CH=CH—$(CH_2)_{12}$—$(OCH_2CH_2)_m$—OCOCH=$CH_2$; $SF_5$—CH=CH—$(CH_2)_{12}$—$(OCH_2CH_2)_m$—OCH=$CH_2$;
$SF_5$—CH=CH—$(CH_2)_{12}$—$(OCH_2CH_2)_m$—OAr(NCO)$_p$
$SF_5$—CH=CH—$(CH_2)_{13}$—$(OCH_2CH_2)_m$—OCOCH=$CH_2$; $SF_5$—CH=CH—$(CH_2)_{13}$—$(OCH_2CH_2)_m$—OCH=$CH_2$;
$SF_5$—CH=CH—$(CH_2)_{13}$—$(OCH_2CH_2)_m$—OAr(NCO)$_p$
$SF_5$—CH=CH—$(CH_2)_{14}$—$(OCH_2CH_2)_m$—OCOCH=$CH_2$; $SF_5$—CH=CH—$(CH_2)_{14}$—$(OCH_2CH_2)_m$—OCH=$CH_2$;
$SF_5$—CH=CH—$(CH_2)_{14}$—$(OCH_2CH_2)_m$—OAr(NCO)$_p$
$SF_5$—CH=CH—$(CH_2)_{15}$—$(OCH_2CH_2)_m$—OCOCH=$CH_2$; $SF_5$—CH=CH—$(CH_2)_{15}$—$(OCH_2CH_2)_m$—OCH=$CH_2$;
$SF_5$—CH=CH—$(CH_2)_{15}$—$(OCH_2CH_2)_m$—OAr(NCO)$_p$
$SF_5$—CH=CH—$(CH_2)_{16}$—$(OCH_2CH_2)_m$—OCOCH=$CH_2$; $SF_5$—CH=CH—$(CH_2)_{16}$—$(OCH_2CH_2)_m$—OCH=$CH_2$;
$SF_5$—CH=CH—$(CH_2)_{16}$—$(OCH_2CH_2)_m$—OAr(NCO)$_p$
$SF_5$—CH=CH—$(CH_2)_{17}$—$(OCH_2CH_2)_m$—OCOCH=$CH_2$; $SF_5$—CH=CH—$(CH_2)_{17}$—$(OCH_2CH_2)_m$—OCH=$CH_2$;
$SF_5$—CH=CH—$(CH_2)_{17}$—$(OCH_2CH_2)_m$—OAr(NCO)$_p$
$SF_5$—CH=CH—$(CH_2)_{18}$—$(OCH_2CH_2)_m$—OCOCH=$CH_2$; $SF_5$—CH=CH—$(CH_2)_{18}$—$(OCH_2CH_2)_m$—OCH=$CH_2$;
$SF_5$—CH=CH—$(CH_2)_{18}$—$(OCH_2CH_2)_m$—OAr(NCO)$_p$
$SF_5$—CH=CH—$(CH_2)_{19}$—$(OCH_2CH_2)_m$—OCOCH=$CH_2$; $SF_5$—CH=CH—$(CH_2)_{19}$—$(OCH_2CH_2)_m$—OCH=$CH_2$;
$SF_5$—CH=CH—$(CH_2)_{19}$—$(OCH_2CH_2)_m$—OAr(NCO)$_p$
$SF_5$—CH=CH—$(CH_2)_{20}$—$(OCH_2CH_2)_m$—OCOCH=$CH_2$; $SF_5$—CH=CH—$(CH_2)_{20}$—$(OCH_2CH_2)_m$—OCH=$CH_2$;
$SF_5$—CH=CH—$(CH_2)_{20}$—$(OCH_2CH_2)_m$—OAr(NCO)$_p$
$SF_5$—CH=CH—$(CH_2)_{21}$—$(OCH_2CH_2)_m$—OCOCH=$CH_2$; $SF_5$—CH=CH—$(CH_2)_{21}$—$(OCH_2CH_2)_m$—OCH=$CH_2$;
$SF_5$—CH=CH—$(CH_2)_{21}$—$(OCH_2CH_2)_m$—OAr(NCO)$_p$
$SF_5$—CH=CH—$(CH_2)_{22}$—$(OCH_2CH_2)_m$—OCOCH=$CH_2$; $SF_5$—CH=CH—$(CH_2)_{22}$—$(OCH_2CH_2)_m$—OCH=$CH_2$;
$SF_5$—CH=CH—$(CH_2)_{22}$—$(OCH_2CH_2)_m$—OAr(NCO)$_p$
$SF_5$—CH=CH—$(CH_2)_{23}$—$(OCH_2CH_2)_m$—OCOCH=$CH_2$; $SF_5$—CH=CH—$(CH_2)_{23}$—$(OCH_2CH_2)_m$—OCH=$CH_2$;
$SF_5$—CH=CH—$(CH_2)_{23}$—$(OCH_2CH_2)_m$—OAr(NCO)$_p$
$SF_5$—CH=CH—$(CH_2)_{24}$—$(OCH_2CH_2)_m$—OCOCH=$CH_2$; $SF_5$—CH=CH—$(CH_2)_{24}$—$(OCH_2CH_2)_m$—OCH=$CH_2$;
$SF_5$—CH=CH—$(CH_2)_{24}$—$(OCH_2CH_2)_m$—OAr(NCO)$_p$
$SF_5$—$CH_2CHBr$—$(CH_2)_4$—$(OCH_2CH_2)_m$—OCOCH=$CH_2$; $SF_5$—$CH_2CHBr$—$(CH_2)_4$—$(OCH_2CH_2)_m$—OCH=$CH_2$;
$SF_5$—$CH_2CHBr$—$(CH_2)_4$—$(OCH_2CH_2)_m$—OAr(NCO)$_p$
$SF_5$—$CH_2CHBr$—$(CH_2)_5$—$(OCH_2CH_2)_m$—OCOCH=$CH_2$; $SF_5$—$CH_2CHBr$—$(CH_2)_5$—$(OCH_2CH_2)_m$—OCH=$CH_2$;
$SF_5$—$CH_2CHBr$—$(CH_2)_5$—$(OCH_2CH_2)_m$—OAr(NCO)$_p$
$SF_5$—$CH_2CHBr$—$(CH_2)_6$—$(OCH_2CH_2)_m$—OCOCH=$CH_2$; $SF_5$—$CH_2CHBr$—$(CH_2)_6$—$(OCH_2CH_2)_m$—OCH=$CH_2$;
$SF_5$—$CH_2CHBr$—$(CH_2)_6$—$(OCH_2CH_2)_m$—OAr(NCO)$_p$
$SF_5$—$CH_2CHBr$—$(CH_2)_7$—$(OCH_2CH_2)_m$—OCOCH=$CH_2$; $SF_5$—$CH_2CHBr$—$(CH_2)_7$—$(OCH_2CH_2)_m$—OCH=$CH_2$;
$SF_5$—$CH_2CHBr$—$(CH_2)_7$—$(OCH_2CH_2)_m$—OAr(NCO)$_p$
$SF_5$—$CH_2CHBr$—$(CH_2)_8$—$(OCH_2CH_2)_m$—OCOCH=$CH_2$; $SF_5$—$CH_2CHBr$—$(CH_2)_8$—$(OCH_2CH_2)_m$—OCH=$CH_2$;
$SF_5$—$CH_2CHBr$—$(CH_2)_8$—$(OCH_2CH_2)_m$—OAr(NCO)$_p$
$SF_5$—$CH_2CHBr$—$(CH_2)_9$—$(OCH_2CH_2)_m$—OCOCH=$CH_2$; $SF_5$—$CH_2CHBr$—$(CH_2)_9$—$(OCH_2CH_2)_m$—OCH=$CH_2$;
$SF_5$—$CH_2CHBr$—$(CH_2)_9$—$(OCH_2CH_2)_m$—OAr(NCO)$_p$
$SF_5$—$CH_2CHBr$—$(CH_2)_{10}$—$(OCH_2CH_2)_m$—OCOCH=$CH_2$; $SF_5$—$CH_2CHBr$—$(CH_2)_{10}$—$(OCH_2CH_2)_m$—OCH=$CH_2$;
$SF_5$—$CH_2CHBr$—$(CH_2)_{10}$—$(OCH_2CH_2)_m$—OAr(NCO)$_p$
$SF_5$—$CH_2CHBr$—$(CH_2)_{11}$—$(OCH_2CH_2)_m$—OCOCH=$CH_2$; $SF_5$—$CH_2CHBr$—$(CH_2)_{11}$—$(OCH_2CH_2)_m$—OCH=$CH_2$;
$SF_5$—$CH_2CHBr$—$(CH_2)_{11}$—$(OCH_2CH_2)_m$—OAr(NCO)$_p$
$SF_5$—$CH_2CHBr$—$(CH_2)_{12}$—$(OCH_2CH_2)_m$—OCOCH=$CH_2$; $SF_5$—$CH_2CHBr$—$(CH_2)_{12}$—$(OCH_2CH_2)_m$—OCH=$CH_2$;
$SF_5$—$CH_2CHBr$—$(CH_2)_{12}$—$(OCH_2CH_2)_m$—OAr(NCO)$_p$
$SF_5$—$CH_2CHBr$—$(CH_2)_{13}$—$(OCH_2CH_2)_m$—OCOCH=$CH_2$; $SF_5$—$CH_2CHBr$—$(CH_2)_{13}$—$(OCH_2CH_2)_m$—OCH=$CH_2$;
$SF_5$—$CH_2CHBr$—$(CH_2)_{13}$—$(OCH_2CH_2)_m$—OAr(NCO)$_p$
$SF_5$—$CH_2CHBr$—$(CH_2)_{14}$—$(OCH_2CH_2)_m$—OCOCH=$CH_2$; $SF_5$—$CH_2CHBr$—$(CH_2)_{14}$—$(OCH_2CH_2)_m$—OCH=$CH_2$;
$SF_5$—$CH_2CHBr$—$(CH_2)_{14}$—$(OCH_2CH_2)_m$—OAr(NCO)$_p$
$SF_5$—$CH_2CHBr$—$(CH_2)_{15}$—$(OCH_2CH_2)_m$—OCOCH=$CH_2$; $SF_5$—$CH_2CHBr$—$(CH_2)_{15}$—$(OCH_2CH_2)_m$—OCH=$CH_2$;
$SF_5$—$CH_2CHBr$—$(CH_2)_{15}$—$(OCH_2CH_2)_m$—OAr(NCO)$_p$
$SF_5$—$CH_2CHBr$—$(CH_2)_{16}$—$(OCH_2CH_2)_m$—OCOCH=$CH_2$; $SF_5$—$CH_2CHBr$—$(CH_2)_{16}$—$(OCH_2CH_2)_m$—OCH=$CH_2$;
$SF_5$—$CH_2CHBr$—$(CH_2)_{16}$—$(OCH_2CH_2)_m$—OAr(NCO)$_p$
$SF_5$—$CH_2CHBr$—$(CH_2)_{17}$—$(OCH_2CH_2)_m$—OCOCH=$CH_2$; $SF_5$—$CH_2CHBr$—$(CH_2)_{17}$—$(OCH_2CH_2)_m$—OCH=$CH_2$;
$SF_5$—$CH_2CHBr$—$(CH_2)_{17}$—$(OCH_2CH_2)_m$—OAr(NCO)$_p$
$SF_5$—$CH_2CHBr$—$(CH_2)_{18}$—$(OCH_2CH_2)_m$—OCOCH=$CH_2$; $SF_5$—$CH_2CHBr$—$(CH_2)_{18}$—$(OCH_2CH_2)_m$—OCH=$CH_2$;
$SF_5$—$CH_2CHBr$—$(CH_2)_{18}$—$(OCH_2CH_2)_m$—OAr(NCO)$_p$
$SF_5$—$CH_2CHBr$—$(CH_2)_{19}$—$(OCH_2CH_2)_m$—OCOCH=$CH_2$; $SF_5$—$CH_2CHBr$—$(CH_2)_{19}$—$(OCH_2CH_2)_m$—OCH=$CH_2$;
$SF_5$—$CH_2CHBr$—$(CH_2)_{19}$—$(OCH_2CH_2)_m$—OAr(NCO)$_p$
$SF_5$—$CH_2CHBr$—$(CH_2)_{20}$—$(OCH_2CH_2)_m$—OCOCH=$CH_2$; $SF_5$—$CH_2CHBr$—$(CH_2)_{20}$—$(OCH_2CH_2)_m$—OCH=$CH_2$;
$SF_5$—$CH_2CHBr$—$(CH_2)_{20}$—$(OCH_2CH_2)_m$—OAr(NCO)$_p$
$SF_5$—$CH_2CHBr$—$(CH_2)_{21}$—$(OCH_2CH_2)_m$—OCOCH=$CH_2$; $SF_5$—$CH_2CHBr$—$(CH_2)_{21}$—$(OCH_2CH_2)_m$—OCH=$CH_2$;
$SF_5$—$CH_2CHBr$—$(CH_2)_{21}$—$(OCH_2CH_2)_m$—OAr(NCO)$_p$
$SF_5$—$CH_2CHBr$—$(CH_2)_{22}$—$(OCH_2CH_2)_m$—OCOCH=$CH_2$; $SF_5$—$CH_2CHBr$—$(CH_2)_{22}$—$(OCH_2CH_2)_m$—OCH=$CH_2$;
$SF_5$—$CH_2CHBr$—$(CH_2)_{22}$—$(OCH_2CH_2)_m$—OAr(NCO)$_p$
$SF_5$—$CH_2CHBr$—$(CH_2)_{23}$—$(OCH_2CH_2)_m$—OCOCH=$CH_2$; $SF_5$—$CH_2CHBr$—$(CH_2)_{23}$—$(OCH_2CH_2)_m$—OCH=$CH_2$;
$SF_5$—$CH_2CHBr$—$(CH_2)_{23}$—$(OCH_2CH_2)_m$—OAr(NCO)$_p$
$SF_5$—$CH_2CHBr$—$(CH_2)_{24}$—$(OCH_2CH_2)_m$—OCOCH=$CH_2$; $SF_5$—$CH_2CHBr$—$(CH_2)_{24}$—$(OCH_2CH_2)_m$—OCH=$CH_2$;
$SF_5$—$CH_2CHBr$—$(CH_2)_{24}$—$(OCH_2CH_2)_m$—OAr(NCO)$_p$ -continued $CF_3-O-(CH_2)_4-N^+R^1R^2R^3Z^-$; $CF_3-O-(CH_2)_4-P^+R^1R^2R^3Z^-$; $CF_3-O-(CH_2)_4-O$-glucoside
$CF_3-O-(CH_2)_5-N^+R^1R^2R^3Z^-$; $CF_3-O-(CH_2)_5-P^+R^1R^2R^3Z^-$; $CF_3-O-(CH_2)_5-O$-glucoside
$CF_3-O-(CH_2)_6-N^+R^1R^2R^3Z^-$; $CF_3-O-(CH_2)_6-P^+R^1R^2R^3Z^-$; $CF_3-O-(CH_2)_6-O$-glucoside
$CF_3-O-(CH_2)_7-N^+R^1R^2R^3Z^-$; $CF_3-O-(CH_2)_7-P^+R^1R^2R^3Z^-$; $CF_3-O-(CH_2)_7-O$-glucoside
$CF_3-O-(CH_2)_8-N^+R^1R^2R^3Z^-$; $CF_3-O-(CH_2)_8-P^+R^1R^2R^3Z^-$; $CF_3-O-(CH_2)_8-O$-glucoside
$CF_3-O-(CH_2)_9-N^+R^1R^2R^3Z^-$; $CF_3-O-(CH_2)_9-P^+R^1R^2R^3Z^-$; $CF_3-O-(CH_2)_9-O$-glucoside
$CF_3-O-(CH_2)_{10}-N^+R^1R^2R^3Z^-$; $CF_3-O-(CH_2)_{10}-P^+R^1R^2R^3Z^-$; $CF_3-O-(CH_2)_{10}-O$-glucoside
$CF_3-O-(CH_2)_{11}-N^+R^1R^2R^3Z^-$; $CF_3-O-(CH_2)_{11}-P^+R^1R^2R^3Z^-$; $CF_3-O-(CH_2)_{11}-O$-glucoside
$CF_3-O-(CH_2)_{12}-N^+R^1R^2R^3Z^-$; $CF_3-O-(CH_2)_{12}-P^+R^1R^2R^3Z^-$; $CF_3-O-(CH_2)_{12}-O$-glucoside
$CF_3-O-(CH_2)_{13}-N^+R^1R^2R^3Z^-$; $CF_3-O-(CH_2)_{13}-P^+R^1R^2R^3Z^-$; $CF_3-O-(CH_2)_{13}-O$-glucoside
$CF_3-O-(CH_2)_{14}-N^+R^1R^2R^3Z^-$; $CF_3-O-(CH_2)_{14}-P^+R^1R^2R^3Z^-$; $CF_3-O-(CH_2)_{14}-O$-glucoside
$CF_3-O-(CH_2)_{15}-N^+R^1R^2R^3Z^-$; $CF_3-O-(CH_2)_{15}-P^+R^1R^2R^3Z^-$; $CF_3-O-(CH_2)_{15}-O$-glucoside
$CF_3-O-(CH_2)_{16}-N^+R^1R^2R^3Z^-$; $CF_3-O-(CH_2)_{16}-P^+R^1R^2R^3Z^-$; $CF_3-O-(CH_2)_{16}-O$-glucoside
$CF_3-O-(CH_2)_{17}-N^+R^1R^2R^3Z^-$; $CF_3-O-(CH_2)_{17}-P^+R^1R^2R^3Z^-$; $CF_3-O-(CH_2)_{17}-O$-glucoside
$CF_3-O-(CH_2)_{18}-N^+R^1R^2R^3Z^-$; $CF_3-O-(CH_2)_{18}-P^+R^1R^2R^3Z^-$; $CF_3-O-(CH_2)_{18}-O$-glucoside
$CF_3-O-(CH_2)_{19}-N^+R^1R^2R^3Z^-$; $CF_3-O-(CH_2)_{19}-P^+R^1R^2R^3Z^-$; $CF_3-O-(CH_2)_{19}-O$-glucoside
$CF_3-O-(CH_2)_{20}-N^+R^1R^2R^3Z^-$; $CF_3-O-(CH_2)_{20}-P^+R^1R^2R^3Z^-$; $CF_3-O-(CH_2)_{20}-O$-glucoside
$CF_3-O-(CH_2)_{21}-N^+R^1R^2R^3Z^-$; $CF_3-O-(CH_2)_{21}-P^+R^1R^2R^3Z^-$; $CF_3-O-(CH_2)_{21}-O$-glucoside
$CF_3-O-(CH_2)_{22}-N^+R^1R^2R^3Z^-$; $CF_3-O-(CH_2)_{22}-P^+R^1R^2R^3Z^-$; $CF_3-O-(CH_2)_{22}-O$-glucoside
$CF_3-O-(CH_2)_{23}-N^+R^1R^2R^3Z^-$; $CF_3-O-(CH_2)_{23}-P^+R^1R^2R^3Z^-$; $CF_3-O-(CH_2)_{23}-O$-glucoside
$CF_3-O-(CH_2)_{24}-N^+R^1R^2R^3Z^-$; $CF_3-O-(CH_2)_{24}-P^+R^1R^2R^3Z^-$; $CF_3-O-(CH_2)_{24}-O$-glucoside
$SF_5-(CH_2)_4-N^+R^1R^2R^3Z^-$; $SF_5-(CH_2)_4-P^+R^1R^2R^3Z^-$; $SF_5-(CH_2)_4-O$-glucoside
$SF_5-(CH_2)_5-N^+R^1R^2R^3Z^-$; $SF_5-(CH_2)_5-P^+R^1R^2R^3Z^-$; $SF_5-(CH_2)_5-O$-glucoside
$SF_5-(CH_2)_6-N^+R^1R^2R^3Z^-$; $SF_5-(CH_2)_6-P^+R^1R^2R^3Z^-$; $SF_5-(CH_2)_6-O$-glucoside
$SF_5-(CH_2)_7-N^+R^1R^2R^3Z^-$; $SF_5-(CH_2)_7-P^+R^1R^2R^3Z^-$; $SF_5-(CH_2)_7-O$-glucoside
$SF_5-(CH_2)_8-N^+R^1R^2R^3Z^-$; $SF_5-(CH_2)_8-P^+R^1R^2R^3Z^-$; $SF_5-(CH_2)_8-O$-glucoside
$SF_5-(CH_2)_9-N^+R^1R^2R^3Z^-$; $SF_5-(CH_2)_9-P^+R^1R^2R^3Z^-$; $SF_5-(CH_2)_9-O$-glucoside
$SF_5-(CH_2)_{10}-N^+R^1R^2R^3Z^-$; $SF_5-(CH_2)_{10}-P^+R^1R^2R^3Z^-$; $SF_5-(CH_2)_{10}-O$-glucoside
$SF_5-(CH_2)_{11}-N^+R^1R^2R^3Z^-$; $SF_5-(CH_2)_{11}-P^+R^1R^2R^3Z^-$; $SF_5-(CH_2)_{11}-O$-glucoside
$SF_5-(CH_2)_{12}-N^+R^1R^2R^3Z^-$; $SF_5-(CH_2)_{12}-P^+R^1R^2R^3Z^-$; $SF_5-(CH_2)_{12}-O$-glucoside
$SF_5-(CH_2)_{13}-N^+R^1R^2R^3Z^-$; $SF_5-(CH_2)_{13}-P^+R^1R^2R^3Z^-$; $SF_5-(CH_2)_{13}-O$-glucoside
$SF_5-(CH_2)_{14}-N^+R^1R^2R^3Z^-$; $SF_5-(CH_2)_{14}-P^+R^1R^2R^3Z^-$; $SF_5-(CH_2)_{14}-O$-glucoside
$SF_5-(CH_2)_{15}-N^+R^1R^2R^3Z^-$; $SF_5-(CH_2)_{15}-P^+R^1R^2R^3Z^-$; $SF_5-(CH_2)_{15}-O$-glucoside
$SF_5-(CH_2)_{16}-N^+R^1R^2R^3Z^-$; $SF_5-(CH_2)_{16}-P^+R^1R^2R^3Z^-$; $SF_5-(CH_2)_{16}-O$-glucoside
$SF_5-(CH_2)_{17}-N^+R^1R^2R^3Z^-$; $SF_5-(CH_2)_{17}-P^+R^1R^2R^3Z^-$; $SF_5-(CH_2)_{17}-O$-glucoside
$SF_5-(CH_2)_{18}-N^+R^1R^2R^3Z^-$; $SF_5-(CH_2)_{18}-P^+R^1R^2R^3Z^-$; $SF_5-(CH_2)_{18}-O$-glucoside
$SF_5-(CH_2)_{19}-N^+R^1R^2R^3Z^-$; $SF_5-(CH_2)_{19}-P^+R^1R^2R^3Z^-$; $SF_5-(CH_2)_{19}-O$-glucoside
$SF_5-(CH_2)_{20}-N^+R^1R^2R^3Z^-$; $SF_5-(CH_2)_{20}-P^+R^1R^2R^3Z^-$; $SF_5-(CH_2)_{20}-O$-glucoside
$SF_5-(CH_2)_{21}-N^+R^1R^2R^3Z^-$; $SF_5-(CH_2)_{21}-P^+R^1R^2R^3Z^-$; $SF_5-(CH_2)_{21}-O$-glucoside
$SF_5-(CH_2)_{22}-N^+R^1R^2R^3Z^-$; $SF_5-(CH_2)_{22}-P^+R^1R^2R^3Z^-$; $SF_5-(CH_2)_{22}-O$-glucoside
$SF_5-(CH_2)_{23}-N^+R^1R^2R^3Z^-$; $SF_5-(CH_2)_{23}-P^+R^1R^2R^3Z^-$; $SF_5-(CH_2)_{23}-O$-glucoside
$SF_5-(CH_2)_{24}-N^+R^1R^2R^3Z^-$; $SF_5-(CH_2)_{24}-P^+R^1R^2R^3Z^-$; $SF_5-(CH_2)_{24}-O$-glucoside
$SF_5-CH=CH-(CH_2)_4-N^+R^1R^2R^3Z^-$; $SF_5-CH=CH-(CH_2)_4-P^+R^1R^2R^3Z^-$; $SF_5-CH=CH-(CH_2)_4-O$-glucoside
$SF_5-CH=CH-(CH_2)_5-N^+R^1R^2R^3Z^-$; $SF_5-CH=CH-(CH_2)_5-P^+R^1R^2R^3Z^-$; $SF_5-CH=CH-(CH_2)_5-O$-glucoside
$SF_5-CH=CH-(CH_2)_6-N^+R^1R^2R^3Z^-$; $SF_5-CH=CH-(CH_2)_6-P^+R^1R^2R^3Z^-$; $SF_5-CH=CH-(CH_2)_6-O$-glucoside
$SF_5-CH=CH-(CH_2)_7-N^+R^1R^2R^3Z^-$; $SF_5-CH=CH-(CH_2)_7-P^+R^1R^2R^3Z^-$; $SF_5-CH=CH-(CH_2)_7-O$-glucoside
$SF_5-CH=CH-(CH_2)_8-N^+R^1R^2R^3Z^-$; $SF_5-CH=CH-(CH_2)_8-P^+R^1R^2R^3Z^-$; $SF_5-CH=CH-(CH_2)_8-O$-glucoside
$SF_5-CH=CH-(CH_2)_9-N^+R^1R^2R^3Z^-$; $SF_5-CH=CH-(CH_2)_9-P^+R^1R^2R^3Z^-$; $SF_5-CH=CH-(CH_2)_9-O$-glucoside -continued $SF_5-CH=CH-(CH_2)_{10}-N^+R^1R^2R^3Z^-$; $SF_5-CH=CH-(CH_2)_{10}-P^+R^1R^2R^3Z^-$; $SF_5-CH=CH-(CH_2)_{10}-O$-glucoside
$SF_5-CH=CH-(CH_2)_{11}-N^+R^1R^2R^3Z^-$; $SF_5-CH=CH-(CH_2)_{11}-P^+R^1R^2R^3Z^-$; $SF_5-CH=CH-(CH_2)_{11}-O$-glucoside
$SF_5-CH=CH-(CH_2)_{12}-N^+R^1R^2R^3Z^-$; $SF_5-CH=CH-(CH_2)_{12}-P^+R^1R^2R^3Z^-$; $SF_5-CH=CH-(CH_2)_{12}-O$-glucoside
$SF_5-CH=CH-(CH_2)_{13}-N^+R^1R^2R^3Z^-$; $SF_5-CH=CH-(CH_2)_{13}-P^+R^1R^2R^3Z^-$; $SF_5-CH=CH-(CH_2)_{13}-O$-glucoside
$SF_5-CH=CH-(CH_2)_{14}-N^+R^1R^2R^3Z^-$; $SF_5-CH=CH-(CH_2)_{14}-P^+R^1R^2R^3Z^-$; $SF_5-CH=CH-(CH_2)_{14}-O$-glucoside
$SF_5-CH=CH-(CH_2)_{15}-N^+R^1R^2R^3Z^-$; $SF_5-CH=CH-(CH_2)_{15}-P^+R^1R^2R^3Z^-$; $SF_5-CH=CH-(CH_2)_{15}-O$-glucoside
$SF_5-CH=CH-(CH_2)_{16}-N^+R^1R^2R^3Z^-$; $SF_5-CH=CH-(CH_2)_{16}-P^+R^1R^2R^3Z^-$; $SF_5-CH=CH-(CH_2)_{16}-O$-glucoside
$SF_5-CH=CH-(CH_2)_{17}-N^+R^1R^2R^3Z^-$; $SF_5-CH=CH-(CH_2)_{17}-P^+R^1R^2R^3Z^-$; $SF_5-CH=CH-(CH_2)_{17}-O$-glucoside
$SF_5-CH=CH-(CH_2)_{18}-N^+R^1R^2R^3Z^-$; $SF_5-CH=CH-(CH_2)_{18}-P^+R^1R^2R^3Z^-$; $SF_5-CH=CH-(CH_2)_{18}-O$-glucoside
$SF_5-CH=CH-(CH_2)_{19}-N^+R^1R^2R^3Z^-$; $SF_5-CH=CH-(CH_2)_{19}-P^+R^1R^2R^3Z^-$; $SF_5-CH=CH-(CH_2)_{19}-O$-glucoside
$SF_5-CH=CH-(CH_2)_{20}-N^+R^1R^2R^3Z^-$; $SF_5-CH=CH-(CH_2)_{20}-P^+R^1R^2R^3Z^-$; $SF_5-CH=CH-(CH_2)_{20}-O$-glucoside
$SF_5-CH=CH-(CH_2)_{21}-N^+R^1R^2R^3Z^-$; $SF_5-CH=CH-(CH_2)_{21}-P^+R^1R^2R^3Z^-$; $SF_5-CH=CH-(CH_2)_{21}-O$-glucoside
$SF_5-CH=CH-(CH_2)_{22}-N^+R^1R^2R^3Z^-$; $SF_5-CH=CH-(CH_2)_{22}-P^+R^1R^2R^3Z^-$; $SF_5-CH=CH-(CH_2)_{22}-O$-glucoside
$SF_5-CH=CH-(CH_2)_{23}-N^+R^1R^2R^3Z^-$; $SF_5-CH=CH-(CH_2)_{23}-P^+R^1R^2R^3Z^-$; $SF_5-CH=CH-(CH_2)_{23}-O$-glucoside
$SF_5-CH=CH-(CH_2)_{24}-N^+R^1R^2R^3Z^-$; $SF_5-CH=CH-(CH_2)_{24}-P^+R^1R^2R^3Z^-$; $SF_5-CH=CH-(CH_2)_{24}-O$-glucoside
$SF_5-CH_2CHBr-(CH_2)_4-N^+R^1R^2R^3Z^-$; $SF_5-CH_2CHBr-(CH_2)_4-P^+R^1R^2R^3Z^-$; $SF_5-CH_2CHBr-(CH_2)_4-O$-glucoside
$SF_5-CH_2CHBr-(CH_2)_5-N^+R^1R^2R^3Z^-$; $SF_5-CH_2CHBr-(CH_2)_5-P^+R^1R^2R^3Z^-$; $SF_5-CH_2CHBr-(CH_2)_5-O$-glucoside
$SF_5-CH_2CHBr-(CH_2)_6-N^+R^1R^2R^3Z^-$; $SF_5-CH_2CHBr-(CH_2)_6-P^+R^1R^2R^3Z^-$; $SF_5-CH_2CHBr-(CH_2)_6-O$-glucoside
$SF_5-CH_2CHBr-(CH_2)_7-N^+R^1R^2R^3Z^-$; $SF_5-CH_2CHBr-(CH_2)_7-P^+R^1R^2R^3Z^-$; $SF_5-CH_2CHBr-(CH_2)_7-O$-glucoside
$SF_5-CH_2CHBr-(CH_2)_8-N^+R^1R^2R^3Z^-$; $SF_5-CH_2CHBr-(CH_2)_8-P^+R^1R^2R^3Z^-$; $SF_5-CH_2CHBr-(CH_2)_8-O$-glucoside
$SF_5-CH_2CHBr-(CH_2)_9-N^+R^1R^2R^3Z^-$; $SF_5-CH_2CHBr-(CH_2)_9-P^+R^1R^2R^3Z^-$; $SF_5-CH_2CHBr-(CH_2)_9-O$-glucoside
$SF_5-CH_2CHBr-(CH_2)_{10}-N^+R^1R^2R^3Z^-$; $SF_5-CH_2CHBr-(CH_2)_{10}-P^+R^1R^2R^3Z^-$; $SF_5-CH_2CHBr-(CH_2)_{10}-O$-glucoside
$SF_5-CH_2CHBr-(CH_2)_{11}-N^+R^1R^2R^3Z^-$; $SF_5-CH_2CHBr-(CH_2)_{11}-P^+R^1R^2R^3Z^-$; $SF_5-CH_2CHBr-(CH_2)_{11}-O$-glucoside
$SF_5-CH_2CHBr-(CH_2)_{12}-N^+R^1R^2R^3Z^-$; $SF_5-CH_2CHBr-(CH_2)_{12}-P^+R^1R^2R^3Z^-$; $SF_5-CH_2CHBr-(CH_2)_{12}-O$-glucoside
$SF_5-CH_2CHBr-(CH_2)_{13}-N^+R^1R^2R^3Z^-$; $SF_5-CH_2CHBr-(CH_2)_{13}-P^+R^1R^2R^3Z^-$; $SF_5-CH_2CHBr-(CH_2)_{13}-O$-glucoside
$SF_5-CH_2CHBr-(CH_2)_{14}-N^+R^1R^2R^3Z^-$; $SF_5-CH_2CHBr-(CH_2)_{14}-P^+R^1R^2R^3Z^-$; $SF_5-CH_2CHBr-(CH_2)_{14}-O$-glucoside
$SF_5-CH_2CHBr-(CH_2)_{15}-N^+R^1R^2R^3Z^-$; $SF_5-CH_2CHBr-(CH_2)_{15}-P^+R^1R^2R^3Z^-$; $SF_5-CH_2CHBr-(CH_2)_{15}-O$-glucoside
$SF_5-CH_2CHBr-(CH_2)_{16}-N^+R^1R^2R^3Z^-$; $SF_5-CH_2CHBr-(CH_2)_{16}-P^+R^1R^2R^3Z^-$; $SF_5-CH_2CHBr-(CH_2)_{16}-O$-glucoside
$SF_5-CH_2CHBr-(CH_2)_{17}-N^+R^1R^2R^3Z^-$; $SF_5-CH_2CHBr-(CH_2)_{17}-P^+R^1R^2R^3Z^-$; $SF_5-CH_2CHBr-(CH_2)_{17}-O$-glucoside
$SF_5-CH_2CHBr-(CH_2)_{18}-N^+R^1R^2R^3Z^-$; $SF_5-CH_2CHBr-(CH_2)_{18}-P^+R^1R^2R^3Z^-$; $SF_5-CH_2CHBr-(CH_2)_{18}-O$-glucoside
$SF_5-CH_2CHBr-(CH_2)_{19}-N^+R^1R^2R^3Z^-$; $SF_5-CH_2CHBr-(CH_2)_{19}-P^+R^1R^2R^3Z^-$; $SF_5-CH_2CHBr-(CH_2)_{19}-O$-glucoside
$SF_5-CH_2CHBr-(CH_2)_{20}-N^+R^1R^2R^3Z^-$; $SF_5-CH_2CHBr-(CH_2)_{20}-P^+R^1R^2R^3Z^-$; $SF_5-CH_2CHBr-(CH_2)_{20}-O$-glucoside
$SF_5-CH_2CHBr-(CH_2)_{21}-N^+R^1R^2R^3Z^-$; $SF_5-CH_2CHBr-(CH_2)_{21}-P^+R^1R^2R^3Z^-$; $SF_5-CH_2CHBr-(CH_2)_{21}-O$-glucoside
$SF_5-CH_2CHBr-(CH_2)_{22}-N^+R^1R^2R^3Z^-$; $SF_5-CH_2CHBr-(CH_2)_{22}-P^+R^1R^2R^3Z^-$; $SF_5-CH_2CHBr-(CH_2)_{22}-O$-glucoside
$SF_5-CH_2CHBr-(CH_2)_{23}-N^+R^1R^2R^3Z^-$; $SF_5-CH_2CHBr-(CH_2)_{23}-P^+R^1R^2R^3Z^-$; $SF_5-CH_2CHBr-(CH_2)_{23}-O$-glucoside
$SF_5-CH_2CHBr-(CH_2)_{24}-N^+R^1R^2R^3Z^-$; $SF_5-CH_2CHBr-(CH_2)_{24}-P^+R^1R^2R^3Z^-$; $SF_5-CH_2CHBr-(CH_2)_{24}-O$-glucoside The compounds which can be used in accordance with the invention as surfactant are particularly suitable here for use as hydrophobicising agents, for example for the surface modification of textiles, paper, glass, porous building materials or adsorbents, or as interface mediators or emulsifiers, in particular for the preparation of fluoropolymers, or as viscosity reducers or emulsifiers, in particular in paints, coatings or compositions for surface coating, or as foam stabilisers, in particular in compositions known as "fire-extinguishing foams", or in metalworking for covering electroplating baths to prevent the escape of caustic vapours, or as wetting agents in the production of photographic films and papers, or as flow-control agents in self-gloss emulsions, or as fire-extinguishing agents, and for dirt-repellent finishing.

In addition, the compounds which can be used in accordance with the invention as surfactant are suitable for washing and cleaning applications, in particular of textiles. The cleaning and polishing of hard surfaces is also a potential area of application of the compounds which can be used in accordance with the invention as surfactant. Furthermore, the compounds which can be used in accordance with the invention as surfactant can advantageously be employed in cosmetic products, such as, for example, foam baths and hair shampoos, or as emulsifiers in creams and lotions. A further area of application of the compounds which can be used in accordance with the invention as surfactant is flotation, i.e. the recovery and separation of ores and minerals from dead rock. In addition, preferred compounds which can be used in accordance with the invention as surfactant can also be employed as emulsifiers in foods. Further fields of application are in metal treatment, as leather auxiliaries, construction chemistry and in crop protection.

The surfactants according to the invention are furthermore also suitable as antimicrobial active ingredient, in particular as reagents for antimicrobial surface modification. Of particular advantage for this use is the use of compounds of the formula I or II or III where X stands for a cationic polar group or a polymerisable group.

The compounds to be employed in accordance with the invention are, for use, usually incorporated into appropriately designed compositions. Corresponding compositions, which are likewise a subject-matter of the present invention, comprise at least one surface-active compound having at least one end group Y, where Y stands for $CF_3O-$ or $F_5S-$, and a carrier which is suitable for the particular application and optionally further specific active ingredients and optionally assistants.

Preferred compositions here are paint and coating compositions, fire-extinguishing compositions, lubricants, washing and cleaning compositions, deicers or hydrophobicising compositions for textile finishing or glass treatment. In a preferred variant of the invention, the compositions are hydrophobicising compositions for finishing textiles and carpets.

For the hydrophobic finishing of textiles, hydrophobicising compositions based on polysiloxanes, fluorohydrocarbons or mixtures of aluminium salts or zirconium salts with paraffins are generally employed (cf. in this respect "Handbuch der Textilhilfsmittel" [Handbook of Textile Assistants], A. Chwala, V. Anger, Verlag Ohemie, New York 1977, Chapter 3.24 "Phobiermittel" [Phobicising Agents], pages 735 ff.). The hydrophobic finishing of textiles, in particular in weather-protection clothing, serves to make the latter either water-repellent or waterproof. The hydrophobicising composition is applied to the fibres of the textiles, where it arranges itself in such a way that the hydrophobic moieties are perpendicular to the fibre surface. In this way, the attempts by water to spread over the entire surface are greatly reduced. Owing to the cohesion forces, the water adopts the spherical shape and runs off the textile surface in the form of beads.

Further areas of application of compositions according to the invention are paint and coating compositions, fire-extinguishing compositions (powders and foams), lubricants, washing and cleaning compositions and de-icers.

The compounds to be used in accordance with the invention can be pre-pared by methods known per se to the person skilled in the art from the literature. The aliphatic $OCF_3$ group can be obtained, for example, from alcohols via fluorodesulfuration of xanthogenates (K. Kanie, Y. Tanaka, K. Suzuki, M. Kuroboshi, T. Hiyama, *Bull. Chem. Soc. Jpn.* 2000, 73, 471-484; P. Kirsch, *Modern Fluoroorganic Chemistry; Synthesis, Reactivity, Applications*, Wiley-VCH, Weinheim, 2004, pp. 67 ff., pp. 1441ff.). The corresponding disclosure of the said method in the cited references thus expressly also belongs to the disclosure content of the present application. The introduction of the hydrophilic, anionic, cationic, reactive or polymerisable end group is possible via the corresponding ω-$OCF_3$-alcohol by methods known to the person skilled in the art. Examples are given in the following scheme:

$$Y(CH_2)_nOH \xrightarrow{COF_2} Y(CH_2)_nOOCF \xrightarrow{SF_4} Y(CH_2)_nOCF_3$$
$$\quad A \qquad\qquad\qquad B \qquad\qquad\qquad C$$

Y = Hal, OPg (Pg = protecting group)

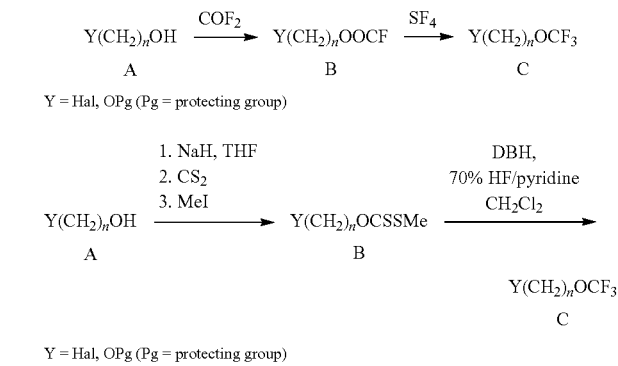

Y = Hal, OPg (Pg = protecting group)

Derivatisation for Y = OPg (e.g. OBn):

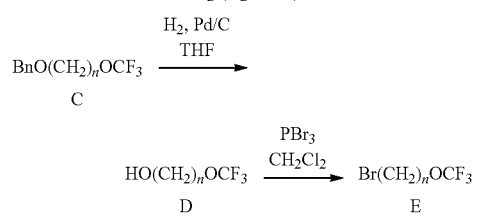

-continued $\xrightarrow{\text{CrO}_3, \text{H}_2\text{SO}_4 \text{ or oxidation}}$ HOOC(CH$_2$)$_{n-1}$OCF$_3$
F $\xrightarrow{\text{CH}_2=\text{CHCOOH, DCC}}$ CH$_2$=CHCOO(CH$_2$)$_n$OCF$_3$
G $\xrightarrow{\text{1. NaH} \atop \text{2. Trichlorotriazine}}$

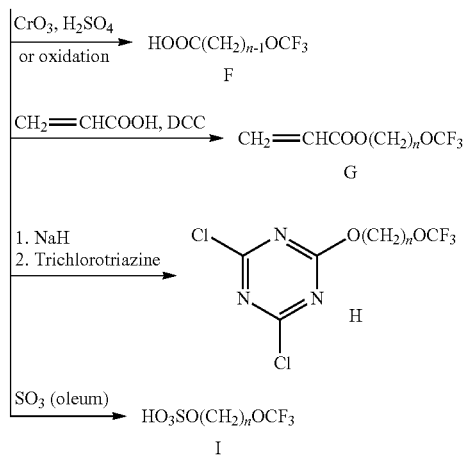

H $\xrightarrow{\text{SO}_3 \text{ (oleum)}}$ HO$_3$SO(CH$_2$)$_n$OCF$_3$
I

Derivatisation for Y = Hal (e.g. Br):

Br(CH$_2$)$_n$OCF$_3$
E

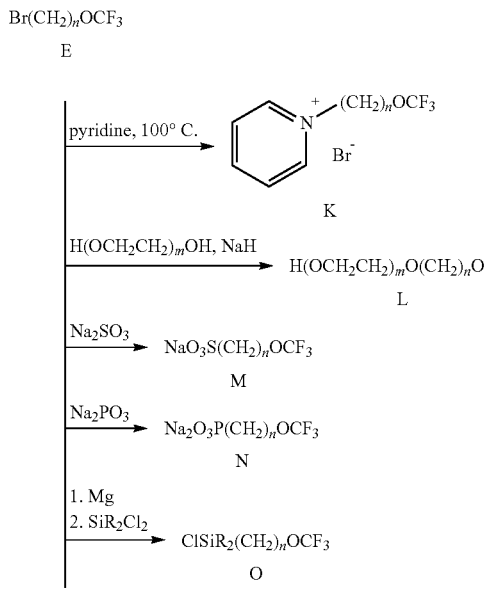

$\xrightarrow{\text{pyridine, 100° C.}}$

K $\xrightarrow{\text{H(OCH}_2\text{CH}_2)_m\text{OH, NaH}}$ H(OCH$_2$CH$_2$)$_m$O(CH$_2$)$_n$OCF$_3$
L $\xrightarrow{\text{Na}_2\text{SO}_3}$ NaO$_3$S(CH$_2$)$_n$OCF$_3$
M $\xrightarrow{\text{Na}_2\text{PO}_3}$ Na$_2$O$_3$P(CH$_2$)$_n$OCF$_3$
N $\xrightarrow{\text{1. Mg} \atop \text{2. SiR}_2\text{Cl}_2}$ ClSiR$_2$(CH$_2$)$_n$OCF$_3$
O $\xrightarrow{\text{R}^1\text{R}^2\text{R}^3\text{N}}$ R$^1$R$^2$R$^3$N$^+$(CH$_2$)$_n$OCF$_3$ Br$^-$
O

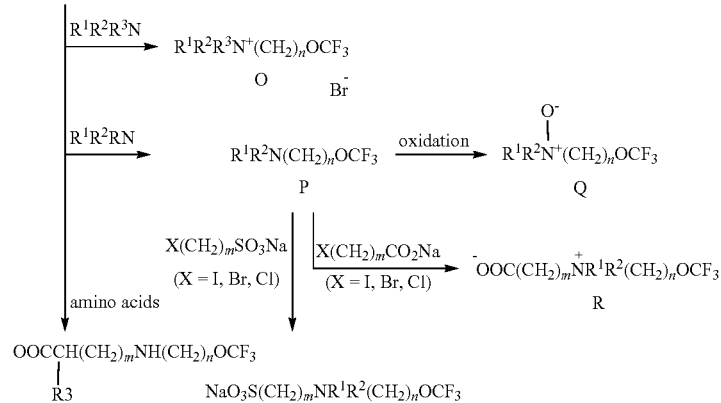

OOCCH(CH$_2$)$_m$NH(CH$_2$)$_n$OCF$_3$
|
R3

NaO$_3$S(CH$_2$)$_m$NR$^1$R$^2$(CH$_2$)$_n$OCF$_3$

The aliphatic SF$_5$ group can be added, for example, onto terminal double bonds by the free-radical addition reaction of SF$_5$Cl or SF$_5$Br. Optional sub-sequent dehydrohalogenation and hydrogenation allow variation of the end groups in accordance with the formulae IIIa, IIIb and IIIc. The first two of these reaction steps are described in the literature (R. Winter, P. G. Nixon, G. L. Gard, D. H. Radford, N. R. Holcomb, D. W. Grainger, *J. Fluorine Chem.* 2001, 107, 23-30), as are catalytic hydrogenations in the presence of an SF$_5$ function (P. Kirsch, M. Bremer, M. Heckmeier, K. Tarumi, *Angew. Chem.* 1999, 111, 2174-2178; *Angew. Chem. Int. Ed. Engl.* 1999, 38, 1989-1992). The corresponding disclosure of the said method in the cited references thus expressly also belongs to the disclosure content of the present application. The introduction of the hydrophilic, reactive or polymerisable component is possible via the corresponding ω-SF$_5$-alcohol by methods known to the person skilled in the art. Examples are revealed by the following scheme:

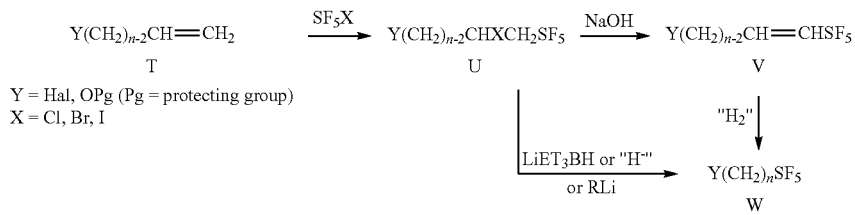

Derivatisation for Y = OPg (e.g. OBn):

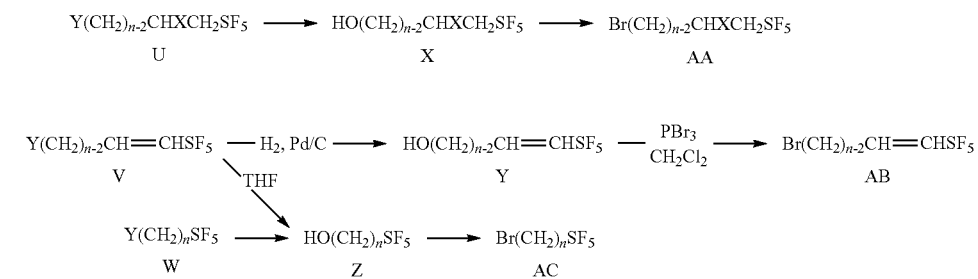

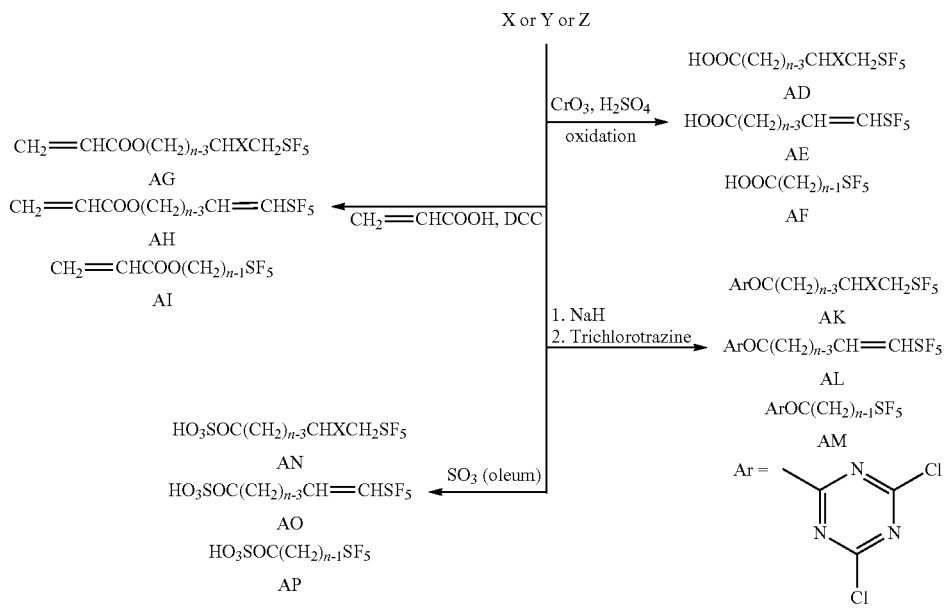

Derivatisation for Y = Hal (e.g. Br):

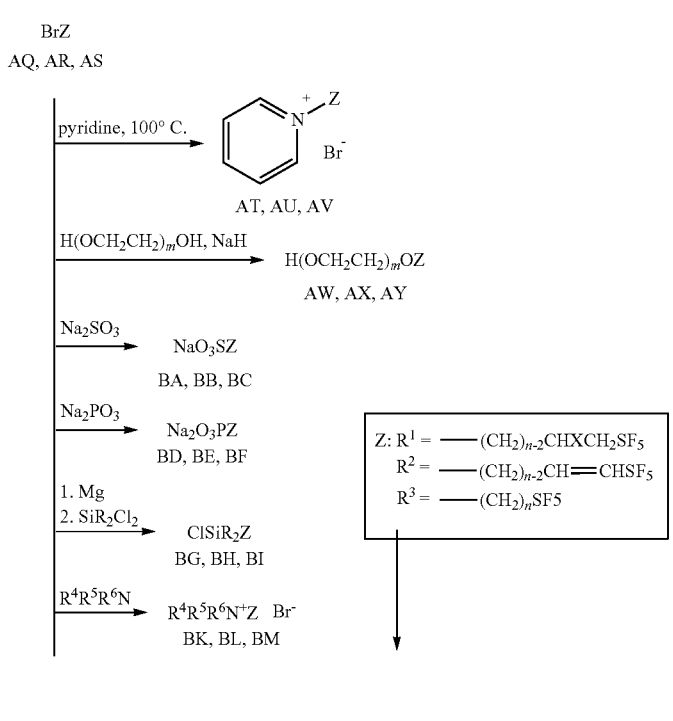

-continued

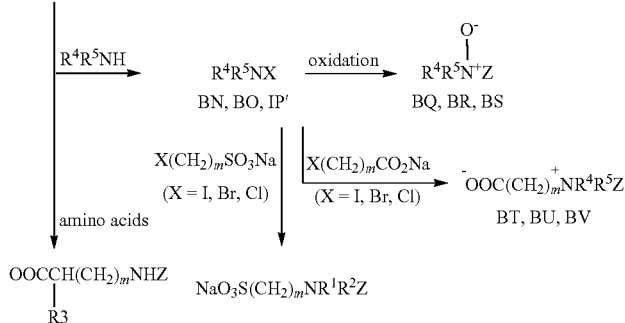

The choice of suitable solvents and reaction conditions presents the person skilled in the art with no difficulties at all (*Organikum: Organisic-Chemisches Grundpraktikum* [Practical Organic Chemistry: A Basic Course], 16th Edn., V E B Deutscher Verlag der Wissenschaften, Berlin, 1986).

The present invention therefore furthermore relates to a process for the preparation of a compound of the formula i, characterised in that firstly a compound of the formula IV Y-spacer-OH      IV is prepared and then, if X in the compound of the formula I is other than OH, converted into the compound of the formula I by modification of the OH group in a manner known per se, a process for the preparation of a compound of the formula IIa, characterised in that firstly a compound of the formula V $F_3CO—(CH_2)_n—OH$      V is prepared by conversion of a protected diol into the protected monotrifluoromethoxyalcohol followed by deprotection, and is then, if X in the compound of the formula Ia is other than OH, converted into the compound of the formula IIa by modification of the OH group in a manner known per se, and a process for the preparation of a compound of the formula IIIa, IIIb or IIIc, characterised in that firstly a compound of the formula IIIb in which X stands for OH is prepared and, if a compound of the formula IIIa or IIIc is to be prepared, reacted by elimination of hydrogen halide and, if a compound of the formula IIIa is to be prepared, subsequent hydrogenation, and subsequently, if X in the compound of the formula IIIa, IIIb or IIIc is other than OH, the product is converted into the compound of the formula IIIa, IIIb or IIIc by modification of the OH group in a manner known per se.

The following examples explain the present invention in greater detail without restricting the scope of protection. In particular, the features, properties and advantages, described in the examples, of the compounds on which the relevant examples are based are also applicable to other substances and compounds which are not mentioned in detail, but fall within the scope of protection, unless stated otherwise elsewhere. Otherwise, the invention can be carried out in the entire scope claimed and is not restricted to the examples mentioned here.

EXAMPLES

List of abbreviations used:

| | |
|---|---|
| Bn: | benzyl |
| DBH: | 1,3-dibromo-5,5-dimethylhydantoin |
| DMAP: | 4-(dimethylamino)pyridine |
| Me: | methyl |
| THF: | tetrahydrofuran |

Example 1

ω-Trifluoromethoxyalkanols

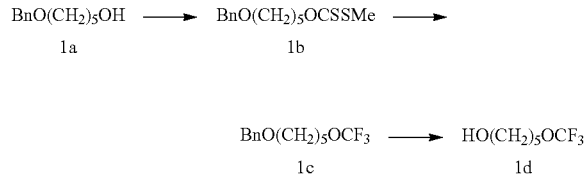

1b: 80 mmol of 1a in 200 ml of THF are added dropwise at 0° C. to a suspension of 95 mmol of NaH in 400 ml of THF. The mixture is heated at 40° C. for 3 h, cooled again to 0° C., and 160 mmol of $CS_2$ are added dropwise. After the mixture has been stirred at RT for a further 1 h, 95 mmol of MeI are added dropwise at 0° C. The mixture is stirred at RT for 18 h, subjected to conventional aqueous work-up and chromatographed over silica gel.

1c: 20 ml of 70% HF/pyridine are added slowly at −78° C. to a suspension of 30 mmol of DBH (1,3-dibromo-5,5-dimethylhydantoin) in 30 ml of $CH_2Cl_2$ in a Teflon flask. A solution of 10 mmol of 1b in 30 ml of $CH_2Cl_2$ is added dropwise to this mixture at −78° C. The mixture is stirred at −78° C. for 30 min, then allowed to come to 0° C. and hydrolysed using $NaHSO_3$ solution. The mixture is subjected to aqueous work-up and chromatographed over silica gel.

1d: 20 mmol of 1c in 400 ml of THF are hydrogenated in the presence of 2g of 5% Pd/C at RT and a pressure of 4 bar until the uptake of hydrogen is complete, The catalyst is filtered off via Celite, and the product is purified by fractional distillation.

Corresponding derivatives can be prepared by variation of the alkyl chain length of the starting materials.

Example 2

ω-Pentafluorosulfuranylalkanols

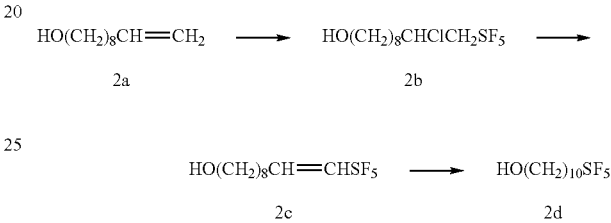

2a and 2b are prepared in accordance with the procedure in R. Winter, P. G. Nixon, G. L. Gard, D. H. Radford, N. R. Holcomb, D. W. Grainger, *J. Fluorine Chem.* 2001, 107, 23-30.

2c-20 mmol of 2b in 400 ml of THF are hydrogenated in the presence of 2 g of 5% Pd/C at RT and atmospheric pressure until the uptake of hydrogen is complete. The catalyst is filtered off via Celite, and the product is purified by fractional distillation.

Corresponding derivatives can be prepared by variation of the alkyl chain length of the starting materials.

Example 3

Surface-Active Substances having Terminal Trifluoro-Methoxy and Pentafluorosulfuranyl Groups

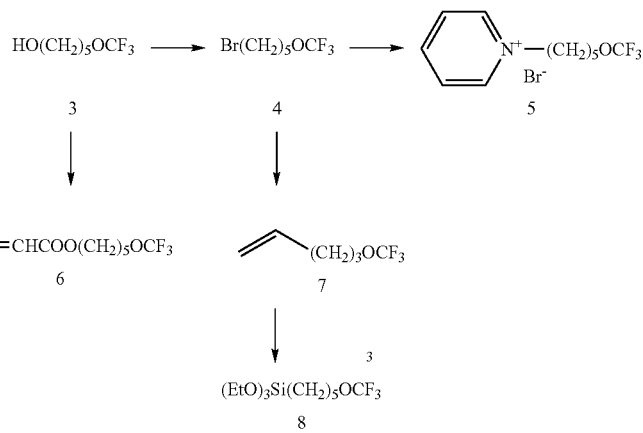

4: 120 mmol of PBr₃ are added to a solution of 100 mmol of 3 in 200 ml of toluene with ice-cooling, and the mixture is heated at reflux for 3 h. The mixture is allowed to cool and subjected to conventional aqueous work-up. The crude product is purified by distillation.

5: A mixture of 10 mmol of 4 and 30 ml of pyridine is heated at the boil for 2 h. The mixture is evaporated under reduced pressure, and the residue is precipitated using diethyl ether.

6: A solution of 100 mmol of 3, 100 mmol of acrylic acid, 105 mmol of di-cyclohexylcarbodiimide and 5 mmol of DMAP in 300 ml of THF is stirred at RT for 18 h. The mixture is poured into water and subjected to conventional aqueous work-up. The crude product is purified by chromatography on silica gel (pentane).

7: A mixture of 100 mmol of 4 and 150 mmol of dicyclohexylamine is heated at 180° C. for 18 h. The product is distilled off, towards the end under reduced pressure and at elevated temperature. The crude product is purified by fractional distillation.

8: 16 mg of H₂PtCl₆.6H₂O in 1 ml of iso-propanol are added to a solution of 10 mmol of 7 and 20 mmol of triethoxysilane in 80 ml of CH₂Cl₂, and the mixture is stirred at RT for 4 d. When the reaction is complete, the product is purified by distillation.

Corresponding derivatives can be prepared by variation of the alkyl chain length of the starting materials.

Example 4

Reaction of 5-pentafluorosulfuranylpentanol analogously to Example 3 gives the corresponding pentafluorosulfuranyl derivatives. Corresponding derivatives can be prepared by variation of the alkyl chain length of the starting materials.

Example 5

ω-Trifluoromethoxyalkanesulfonate

Example 5a

Synthesis of 10-Bromodecyl methyl dithiocarboxylate

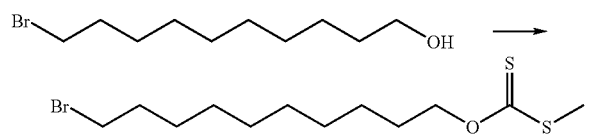

200 ml of tetrahydrofuran (THF)+10.15 g of NaH (253 mmol, 1.2 eq) are introduced into a nitrogen-flushed 1 l four-necked glass apparatus and cooled to −25° C. 50g of 6-bromo-1-decanol (211 mmol, 1 eq), mixed with 100 ml of THF, are added dropwise with cooling. The mixture is stirred at RT for a further 120 min and subsequently again cooled to −25° C. Carbon disulfide (32.1 g; 421.6 mmol; 2 eq) is added dropwise, and the mixture is subsequently stirred at 0° C. for a further 2.5 h. Methyl iodide (35.9 g, 253 mmol; 1.2 eq) is added dropwise at −20° C. with cooling. The reaction mixture is slowly warmed to RT and stirred for a further 24 h. After quenching using 10% NH₄Cl solution (200 ml), the phases are separated, and the organic phase is washed and evaporated to dryness.

Example 5b

Synthesis of 1-bromo-10-trifluoromethoxydecane

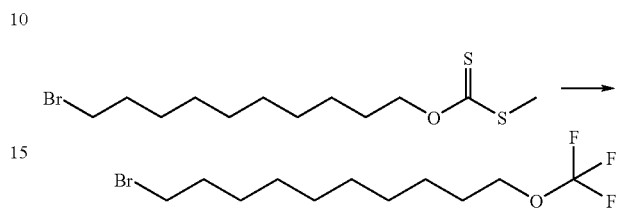

200 ml (7250 mmol, 61 eq) of HF/pyridine (65-70%) are added dropwise at −76° C. to a suspension of 1,3-dibromo-5,5-dimethylhydantoin (102g; 119 mmol; 3 eq) in 420 ml of dichloromoethane, and stirring is continued. The xanthogenate from Example 5a (37g; 118.9 mmol; 1 eq) is then added dropwise in 50 ml of dichloromethane. The reaction mixture is stirred at RT for 12 h. pH=10 is set using aqueous KOH solution. The reaction mixture is diluted with water and methyl t-butyl ether and subsequently filtered The organic phase is dried and purified by column chromatography using heptane.

Example 5c

Synthesis of 10-trifluoromethoxydecane-1-sulfonic acid

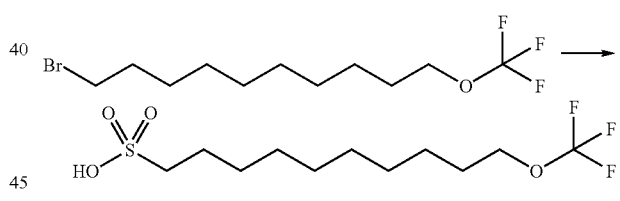

6.8 g of bromide from Example 5b (22.35 mmol) and 3.7 g (29 mmol; 1.3 eq) of sodium sulfite are dissolved in 40 ml of deionised water and 40 ml of ethanol in a 250 ml one-necked flask, and the mixture is heated at 100° C. for 20 h. The cooled reaction mixture is extracted with methyl t-butyl ether/heptane (1:1). The aqueous phase is acidified (pH=0) and extracted with methyl t-butyl ether. The combined organic phases are dried over sodium sulfate and evaporated.

Example 5d

Synthesis of Sodium 10-trifluoromethoxydecane-1-sulfonate

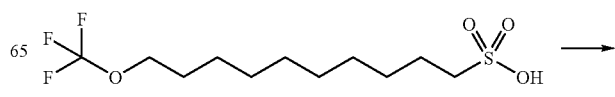

-continued

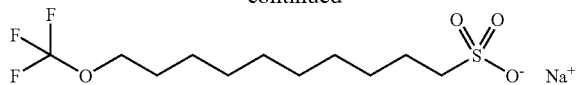

1.15 g (28.8 mmol; 1.3 eq) of NaOH are dissolved in 60 ml of ethanol and added at RT to the sulfonic acid from Example 5c (6.8 g; 22.2 mmol; 1 eq). After refluxing for 1 h, a colourless solid is obtained.

Sulfonates having various alkylene chain lengths can generally be obtained analogously to Example 5.

Example 6

ω-Pentafluorosulfuranyl-(ω-1)-chloroheptane-1-sulfonate

Example 6a

Synthesis of 1-bromo-6-chloro-7-(pentafluorosulfuranyl)heptane

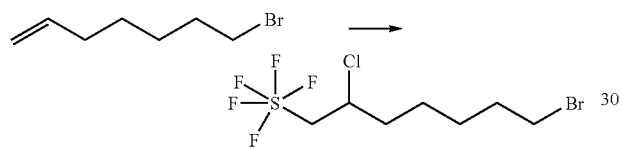

10g (56.5 mmol; 1 eq) of 7-bromoheptene are dissolved in 170 ml of dichloromethane and cooled to −40C. $SF_5Cl$ is condensed in a cold trap and passed into the apparatus as a gas. For activation, 2 ml of 1M $Et_3B$ solution are added. The batch is yellow on introduction of the gas and becomes colourless after addition of $Et_3B$. The addition is repeated until the batch no longer becomes colourless. The reaction mixture is subsequently stirred for a further two hours. The reaction mixture is hydrolysed and adjusted to pH 10. The organic phase is washed and dried.

Example 6b

Synthesis of 6-chloro-7-(pentafluorosulfuranyl)heptane-1-sulfonic acid

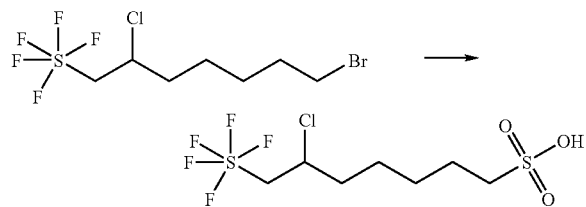

10g (29.4 mmol; 1 eq) of the product from Example Ga and 3.72 g (38.3 mmol; 1.3 eq) of sodium sulfite are dissolved in 50 ml of deionised water and 50 ml of ethanol in a 250 ml one-necked flask and heated at 100° C. for 15 h. After cooling, the reaction mixture is extracted with a 1:1 mixture of methyl t-butyl ether and heptane. The aqueous phase is acidified and extracted with methyl t-butyl ether. The combined organic phases are washed and evaporated to dryness.

Example 6c

Synthesis of Sodium 6-chloro-7-(pentafluorosulfuranyl)heptane-1-sulfonate

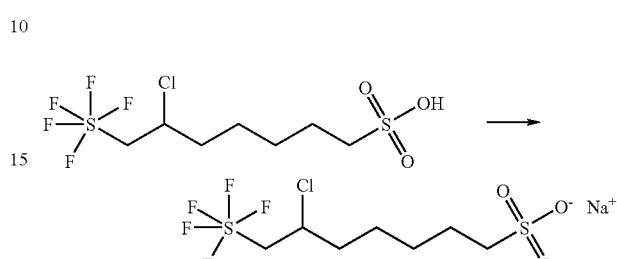

10g (29.35 mmol; 1 eq) of sulfonic acid from Example 6b are suspended in 130 ml of ethanol, and 1.4 9 (35.22 mmol; 1.2 eq) of sodium hydroxide are added. The reaction mixture is heated under reflux for 1 h. The solid is filtered off at RT.

Example 7

Synthesis of Sodium 7-(pentafluorosulfuranyl)hept-6-ene-1-sulfonate:

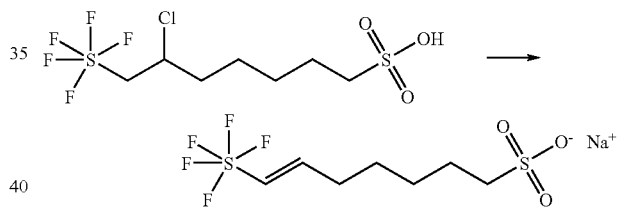

10g (29.35 mmol; 1 eq) of sulfonic acid from Example 6b are suspended in 400 ml of tetrahydrofuran in a 500 ml flask, and 11.74 g (293.5 mmol; 10 eq) of sodium hydroxide are subsequently added. The reaction mixture is heated under reflux for 10 h, cooled and acidified, and the sulfonic acid is separated off from the aqueous phase by repeated extraction with methyl t-butyl ether. The organic phase is subsequently washed and evaporated to dryness. The crude sulfonic acid is suspended in 100 ml of ethanol, 1.4 g (35.22 mmol; 1.2 eq) of sodium hydroxide are added, and the mixture is heated at 97° C. for 1 h. After the suspension has been cooled, crystals deposit, which are filtered off and dried.

Example 8

Determination of the Biochemical Degradability

The biochemical degradability of the compounds is determined by the Zahn-Wellens test in accordance with the publication by the European Commission: Classification, Packaging and Labelling of Dangerous Substances in the European Union, Part II—Test Methods, Annex V—Methods for the Determination of Physico-Chemical Properties, Toxicity and Ecotoxicity, Part B, Biochemical Degradability—Zahn-Wellens Test (C.9.), January 1997, pages 353-357.

| | |
|---|---|
| Batch volume: | 1.5 l |
| Activated sludge concentration: | 1 g of solids/l |
| Origin of the sludge: | Merck KGaA treatment plant, Darmstadt (not adapted) |
| Amount of test substances used: | about 100 to 200 mg/l as DOC |
| Aeration: | with purified air |
| Work-up of the samples: | filtration (medium-hard filter) |
| Determination of the DOC: | by the difference method using a Dimatec instrument |

Further details on the method can be obtained from the above-mentioned publication or also from the OECD guideline for the testing of chemicals, section 3, degradation and accumulation, method 302 B, pages 1-8, adopted: 17 Jul. 1992, the contents of which in this respect expressly belong to the disclosure content of the present application.

Besides the degradation of the compound, the degradation of the fluorine-containing groups is also observed per se in the test via a fluoride determination:

| | |
|---|---|
| Method: | ion chromatography |
| Instrument: | Dionex 120 |
| Detector type: | conductivity detector |
| Column: | AS9HC |
| Eluent: | sodium carbonate solution, 9 mmol/l |
| Flow rate: | 1 ml/min |
| Literature: | EN ISO 10304-2 |

Sodium 10-trifluoromethoxydecane-1-sulfonate from Example 5 is investigated. The measurement values are shown in the following table and depicted graphically in FIG. 1.

| Duration of the measurement (d) | mg/l of free fluoride | Degradation (DOC) in % |
|---|---|---|
| 0 | 1.1 | 0 |
| 0.125 | 1.6 | 0 |
| 1 | 2.0 | 0.5 |
| 2 | 2.6 | 0.7 |
| 5 | 1.1 | 4.5 |
| 8 | 9.6 | 55 |
| 9 | 11.5 | 59 |
| 12 | 20.3 | 66 |
| 15 | 24.5 | 68 |
| 19 | 28.1 | 71 |
| 22 | 30.9 | 72 |
| 26 | 35.7 | 74 |
| 28 | 43.1 | 76 |

It can be seen that the compound is biologically degraded under the experimental conditions with participation of the fluorinated $CF_3O$ group.

Example 9

Determination of the Surface Tension

| | |
|---|---|
| Instrument: | Krüss tensiometer (model K12) |
| Temperature of the measurement solutions: | 20° C. |
| Measurement module employed: | ring |
| Concentration of the measurement solutions: | about 0.5 to 3.0 g/l in deionised water |

Further details on the method can be obtained from the publication by the European Commission Classification, Packaging and Labelling of Dangerous Substances in the European Union, Part II—Test Methods, Annex V—Methods for the Determination of Physico-Chemical Properties, Toxicity and Ecotoxicity, Part A, Surface Tension (A.5), January 1997, pages 51-57, and from the OECD Guideline for the Testing of Chemicals, Section 1, Physical-Chemical Properties, Method 115, pages 1-7, adopted: 27, July 95, the contents of which in this respect expressly belong to the disclosure content of the present application.

Sodium 10-trifluoromethoxydecane-1-sulfonate from Example 5 is investigated in comparison with the classical hydrocarbon surfactant sodium decanesulfonate. The measurement values are shown in the following table and depicted graphically in FIG. 2.

| Sample | Concentration of the solution g/l | Concentration of the solution mol/l | Surface tension mN/m |
|---|---|---|---|
| Example 5 | 0.5015 | 1.527E−03 | 59.95 |
| | 1.0000 | 3.046E−03 | 52.55 |
| | 2.0005 | 6.093E−03 | 42.61 |
| Decane- sulfonic acid Na salt | 1.0020 | 4.101E−03 | 66.13 |
| | 2.0015 | 8.192E−03 | 57.70 |
| | 3.0010 | 1.228E−02 | 52.61 |

It can be seen that the surfactant according to the invention produces the same surface tension at significantly lower concentration compared with the hydrocarbon surfactant. In addition, the curve extrapolation suggests that the end value for the surfactant according to the invention will also be significantly lower than for the hydrocarbon surfactant.

LIST OF FIGURES

Figure 1:
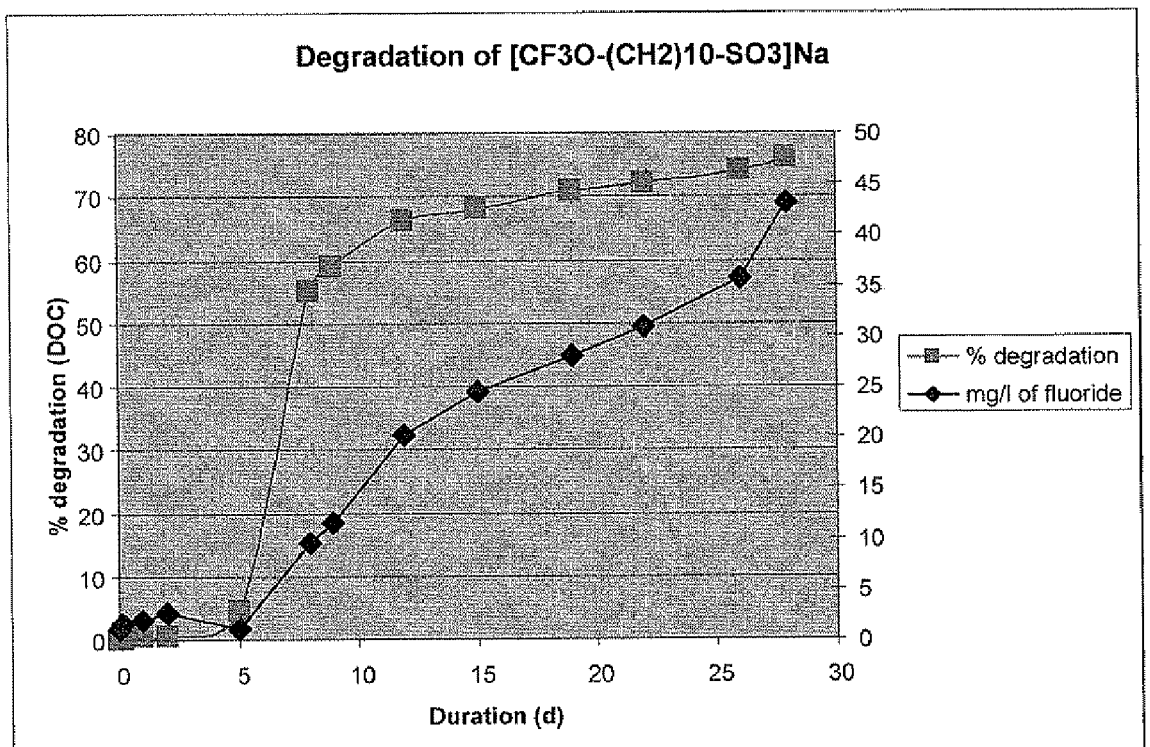
FIG. 1 shows the biochemical degradability of sodium 10-trifluoromethoxydecane-1-sulfonate in the Zahn-Wellens test (DOC values) and the fluoride liberation during the test, in accordance with Example 8.
Figure 2:
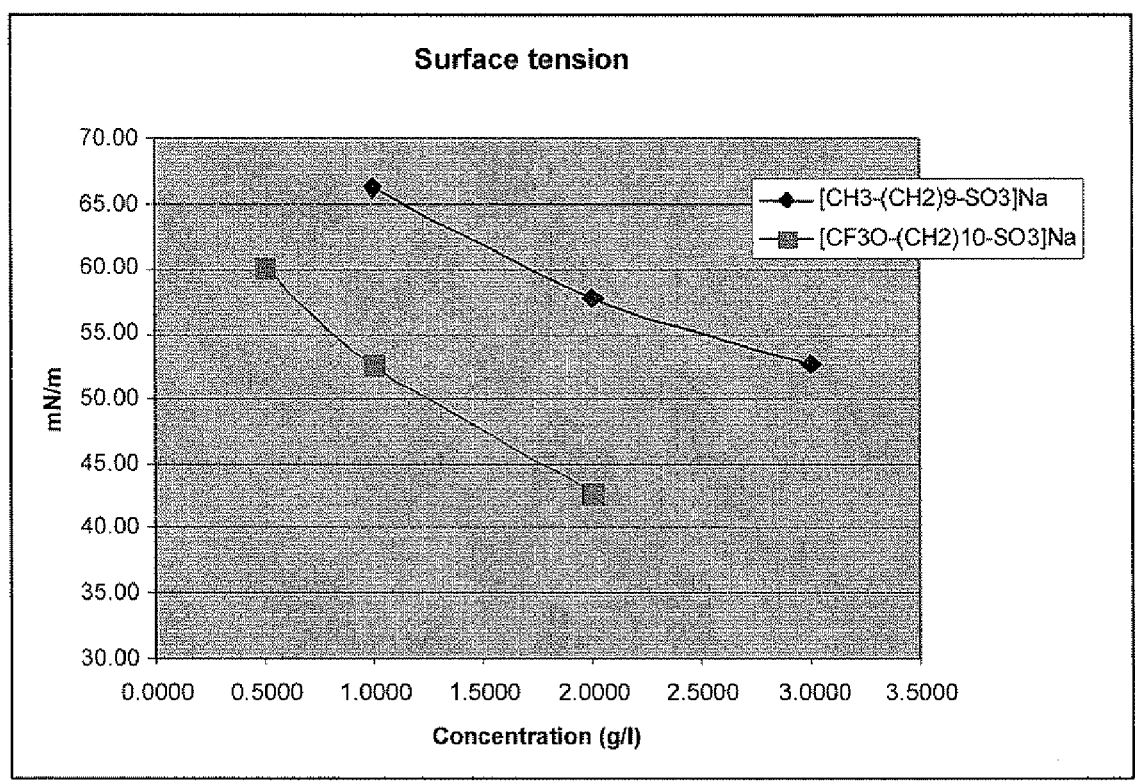
FIG. 2 shows the change in the surface tension of water as a function of the surfactant concentration for sodium 10-trifluoromethoxydecane-1-sulfonate and sodium decanesulfonate in accordance with Example 9.

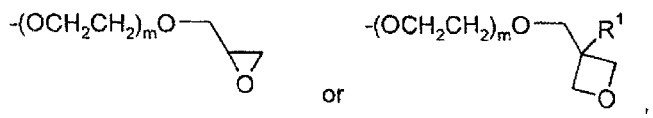

The invention claimed is:

1. A compound of formula IIa, IIb or IIc $$CF_3O\text{—}(CH_2)_n\text{—}X \qquad \text{IIa}$$

$$CF_3O\text{—}CH_2\text{—}CH(Hal)\text{-}(CH_2)_{(n-1)}\text{—}X \qquad \text{IIb}$$

$$CF_3O\text{—}CH\text{=}CH\text{—}(CH_2)_{(n-1)}\text{—}X \qquad \text{IIc}$$

in which
n is an integer from the range 4 to 28,
X is a cationic, nonionic, amphoteric or anionic polar group or a polymerizable group, and
(Hal) is F, Cl, Br or I,
or a corresponding salt of a compound of the formula IIa, IIb or IIc,
where X is not —COOH.

2. A compound of formula IIIa, IIIb or IIIc $$F_5S\text{—}(CH_2)_n\text{—}X \qquad \text{IIIa}$$

$$F_5S\text{—}CH_2\text{—}CH(Hal)\text{-}(CH_2)_{(n-1)}\text{—}X \qquad \text{IIIb}$$

$$F_5S\text{—}CH\text{=}CH\text{—}(CH_2)_{(n-1)}\text{—}X \qquad \text{IIIc}$$

in which n is an integer from the range 1 to 30;

(Hal) is F, Cl, Br or I; and

X is (a) an anionic polar group selected from —COOM, —SO$_3$M, —OSO$_3$M, —PO$_3$M$_2$, —OPO$_3$M$_2$, —(OCH$_2$CH$_2$)$_m$—O—(CH$_2$)$_o$—COOM, —(OCH$_2$CH$_2$)$_m$—O—(CH$_2$)$_o$—SO$_3$M, —(OCH$_2$CH$_2$)$_m$—O—(CH$_2$)$_o$OSO$_3$M, —(OCH$_2$CH$_2$)$_m$—O—(CH$_2$)$_o$—PO$_3$M$_2$, and —(OCH$_2$CH$_2$)$_m$—O—(CH$_2$)$_o$—OPO$_3$M$_2$, in which M is H, an alkali metal ion, or NH$_4^+$, m is an integer from the range 1 to 1000, and o is an integer selected from 1, 2, 3 or 4;

(b) a cationic polar group selected from —NR$^1$R$^2$R$^{3+}$Z$^-$, —PR$^1$R$^2$R$^{3+}$Z$^-$,

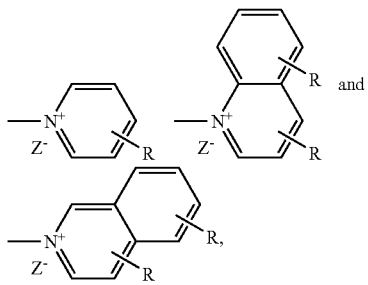

in which

R is H or C$_{1-4}$-alkyl in any desired position,

Z$^-$ is Cl$^-$, Br$^-$, I$^-$, CH$_3$SO$_3^-$, CF$_3$SO$_3^-$, CH$_3$PhSO$_3^-$, PhSO$_3^-$,

R$^1$, R$^2$ and R$^3$ are each, independently of one another, H, C$_{1-30}$-alkyl, Ar, or —CH$_2$Ar, and Ar is an unsubstituted or mono- or polysubstituted aromatic ring or fused ring system having 6 to 18 C atoms, in which, in addition, one or two CH groups are each optionally replaced by N;

(c) a polymerizable group selected from —(OCH$_2$CH$_2$)$_m$OCOCR═CH$_2$, —(OCH$_2$CH$_2$)$_m$—OCR═CH$_2$,

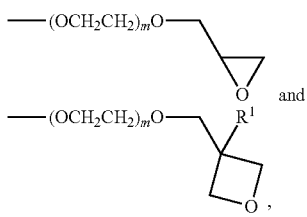

in which m is an integer from the range 0 to 1000, and R and R$^1$ are each H or C$_{1-4}$—; or (d) an amphoteric group selected from acetyldiamines, the N-alkylamino acids, betaines, amine oxides, and corresponding derivatives thereof;

or a corresponding salt of a compound of formula IIIa, IIIb or IIIc, with the proviso that when said compound if of formula IIIa or IIIc and X is an anionic polar group of (a), then n is 4-28.

3. A compound according to claim 1, wherein X is an anionic polar group selected from —COOM, —SO$_3$M, —OSO$_3$M, —PO$_3$M$_2$, —OPO$_3$M$_2$, —(OCH$_2$CH$_2$)$_m$—O—(CH$_2$)$_o$—COOM, —(OCH$_2$CH$_2$)$_m$—O—(CH$_2$)$_o$—SO$_3$M, —(OCH$_2$CH$_2$)$_m$—O—(CH$_2$)$_o$—OSO$_3$M, —(OCH$_2$CH$_2$)$_m$—O—(CH$_2$)$_o$—PO$_3$M$_2$, and —(OCH$_2$CH$_2$)$_m$—O—(CH$_2$)$_o$OPO$_3$M$_2$, M is H, an alkali metal ion, or NH$_4^+$, m is an integer from the range 1 to 1000, and o is an integer selected from 1, 2, 3 or 4, wherein X is not —COOH.

4. A compound according to claim 1, wherein

X is a cationic polar group selected from —NR$^1$R$^2$R$^{3+}$Z$^-$, —PR$^1$R$^2$R$^{3+}$Z$^-$,

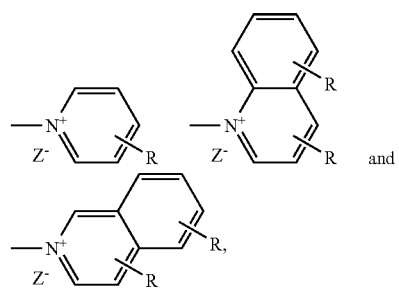

R is H or C$_{1-4}$-alkyl in any desired position,

Z$^-$ is Cl$^-$, Br$^-$, I$^-$, CH$_3$SO$_3^-$, CF$_3$SO$_3^-$, CH$_3$PhSO$_3^-$, or PhSO$_3^-$,

R$^1$, R$^2$ and R$^3$ are each, independently of one another, H, C$_{1-30}$-alkyl, Ar, or —CH$_2$Ar, and Ar is an unsubstituted or mono- or polysubstituted aromatic ring or fused ring system having 6 to 18 C atoms, in which, in addition, one or two CH groups are each optionally replaced by N.

5. A compound according to claim 1, wherein

X is a nonionic polar group selected from —Cl, —Br, —I, —(OCH$_2$CH$_2$)$_m$—OH, —O-(glycoside)$_o$, —(OCH$_2$CH$_2$)$_m$—OCH$_2$—CHOH—CH$_2$—OH, —(OCH$_2$CH$_2$)$_m$—OCH$_2$Ar(—NCO)$_p$, —(OCH$_2$CH$_2$)$_m$—OAr(—NCO)$_p$, —SiR$^1$R$^2$Z, —SiR$^1$Z$_2$, —SiZ$_3$, —COZ, —(OCH$_2$CH$_2$)$_m$—SO$_2$CH═CH$_2$, —SO$_2$Z, and

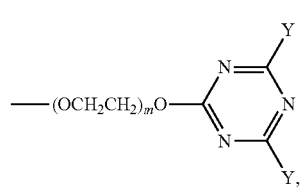

m is an integer from the range 0 to 1000, o is an integer from the range 1 to 10, p is 1 or 2, R$^1$ and R$^2$ are each, independently of one another, C$_{1-30}$-alkyl, Ar, or —CH$_2$Ar, Ar is an unsubstituted or mono- or polysubstituted aromatic ring or fused ring system having 6 to 18 C atoms, in which, in addition, one or two CH groups are each optionally replaced by N, glycoside is an etherified carbohydrate, all Z are each, independently of one another, —H, —Cl, —F, —NR$^1$R$^2$, —OR$^1$, or —N-imidazolyl, and Y is Cl or F.

6. A compound according to claim 1, wherein

X is a polymerizable group selected from —(OCH$_2$CH$_2$)$_m$OCOCR=CH$_2$, —(OCH$_2$CH$_2$)$_m$—OCR=CH$_2$,

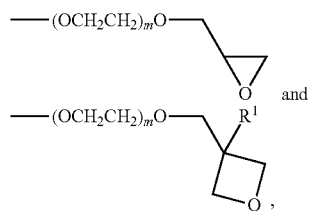 and m is an integer from the range 0 to 1000, and

R and R$^1$ are each H or C$_{1-4}$-alkyl.

7. A compound according to claim 1, wherein X is an amphoteric group selected from acetyldiamines, N-alkylamino acids, betaines, amine oxides, and corresponding derivatives thereof.

8. A composition comprising at least one surface-active compound according to claim 1, a suitable carrier, and optionally at least one further active ingredient.

9. A composition according to claim 8, wherein said composition is a paint or coating composition, fire-extinguishing composition, lubricant, washing or cleaning composition, de-icer or hydrophobicising composition for textile finishing or glass treatment.

10. A compound according to claim 3, wherein M is H, Li$^+$, Na$^+$ or K$^+$, or NH$_4^+$.

11. A compound according to claim 5, wherein glycoside is a mono-, di-, tri- or oligoglucoside.

12. A compound according to claim 1, wherein subscript n is a number from the range 8 to 24.

13. A compound according to claim 1, wherein said compound is of formula IIa.

14. A compound according to claim 1, wherein said compound is of formula IIb.

15. A compound according to claim 1, wherein said compound is of formula IIc.

16. A compound according to claim 2, wherein said compound is of formula IIIa.

17. A compound according to claim 2, wherein said compound is of formula IIIb.

18. A compound according to claim 2, wherein said compound is of formula IIIc.

19. A compound according to claim 2, wherein X is an anionic polar group selected from —COOM, —SO$_3$M, —OSO$_3$M, —PO$_3$M$_2$, —OPO$_3$M$_2$, —(OCH$_2$CH$_2$)$_m$—O—(CH$_2$)$_o$—COOM, —(OCH$_2$CH$_2$)$_m$—O—(CH$_2$)$_o$—SO$_3$M, —(OCH$_2$CH$_2$)$_m$—O—(CH$_2$)$_o$—OSO$_3$M, —(OCH$_2$CH$_2$)$_m$—O—(CH$_2$)$_o$—PO$_3$M$_2$, and —(OCH$_2$CH$_2$)$_m$—O—(CH$_2$)$_o$—OPO$_3$M$_2$, M is H, an alkali metal ion, or NH$_4^+$, m is an integer from the range 1 to 1000, and o is an integer selected from 1, 2, 3 or 4.

20. A compound according to claim 2, wherein

X is a cationic polar group selected from —NR$^1$R$^2$R$^{3+}$Z$^-$, —PR$^1$R$^2$R$^{3+}$Z$^-$,

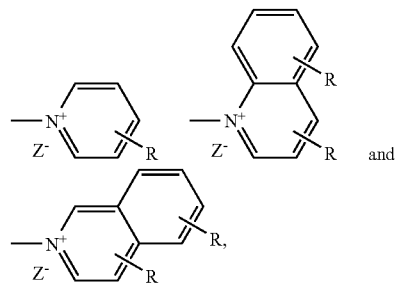

R is H or C$_{1-4}$-alkyl in any desired position,

Z$^-$ is Cl$^-$, Br$^-$, I$^-$, CH$_3$SO$_3^-$, CF$_3$SO$_3^-$, CH$_3$PhSO$_3^-$, PhSO$_3^-$,

R$^1$, R$^2$ and R$^3$ are each, independently of one another, H, C$_{1-30}$-alkyl, Ar, or —CH$_2$Ar, and Ar is an unsubstituted or mono- or polysubstituted aromatic ring or fused ring system having 6 to 18 C atoms, in which, in addition, one or two CH groups are each optionally replaced by N.

21. A compound of formula IIIa, IIIb or IIIc $$F_5S—(CH_2)_n—X \qquad \text{IIIa}$$

$$F_5S—CH_2—CH(Hal)\text{-}(CH_2)_{(n-1)}—X \qquad \text{IIIb}$$

$$F_5S—CH=CH—(CH_2)_{(n-1)}—X \qquad \text{IIIc}$$

in which (Hal) is F, Cl, Br or I; and

X is a nonionic polar group selected from —Cl, —O-(glycoside)$_o$, —(OCH$_2$CH$_2$)$_m$—OCH$_2$—CHOH—CH$_2$—OH, —(OCH$_2$CH$_2$)$_m$—OCH$_2$Ar(—NCO)$_p$, —(OCH$_2$CH$_2$)$_m$—OAr(—NCO)$_p$, —SiR$^1$R$^2$Z, —SiR$^1$Z$_2$, —SiZ$_3$, —COZ, —(OCH$_2$CH$_2$)$_m$—SO$_2$CH=CH$_2$, —SO$_2$Z, and

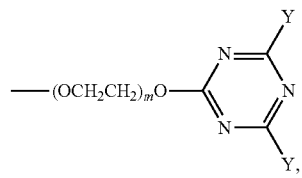

m is an integer from the range 0 to 1000, n is an integer from the range 8 to 24, o is an integer from the range 1 to 10, p is 1 or 2, R$^1$ and R$^2$ are each, independently of one another, C$_{1-30}$-alkyl, Ar, or —CH$_2$Ar, Ar is an unsubstituted or mono- or polysubstituted aromatic ring or fused ring system having 6 to 18 C atoms, in which, in addition, one or two CH groups are each optionally replaced by N, glycoside is an etherified carbohydrate, all Z are each, independently of one another, —H, —Cl, —F, —NR$^1$R$^2$, —OR$^1$, or —N-imidazolyl, and Y is Cl or F.

22. A compound according to claim 2, wherein

X is a polymerizable group selected from —(OCH$_2$CH$_2$)$_m$OCOCR=CH$_2$, —(OCH$_2$CH$_2$)$_m$—OCR=CH$_2$,

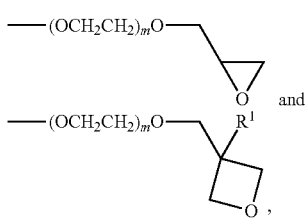

m is an integer from the range 0 to 1000, and
R and R¹ are each H or $C_{1-4}$-alkyl.

23. A compound according to claim 2, wherein X is an amphoteric group selected from acetyldiamines, N-alkylamino acids, betaines, amine oxides, and corresponding derivatives thereof.

24. A compound according to claim 2, wherein the subscript n is a number from the range 4 to 28.

25. A compound according to claim 19, wherein M is H, $Li^+$, $Na^+$ or $K^+$, or $NH_4^+$.

26. A compound according to claim 21, wherein glycoside is a mono-, di-, tri- or oligoglucoside.

27. A compound according to claim 24, wherein the subscript n is a number from the range 8 to 24.

28. A compound according to claim 1, wherein X is a group selected from

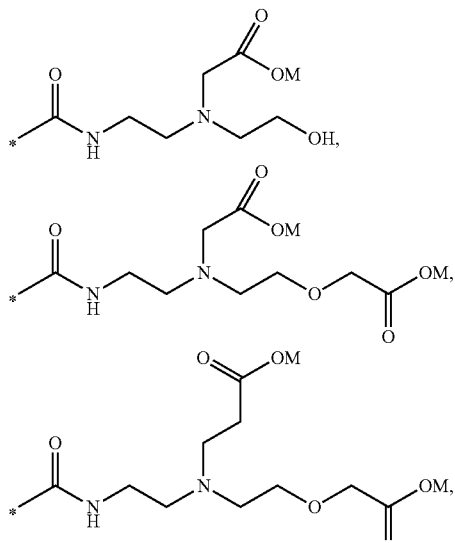

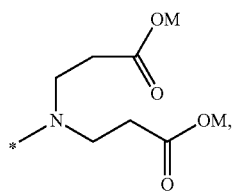

—[(C(=O)—NH—$(CH_2)_{(1-8)}]_{(0\ or\ 1)}$—$N^+R^1R^2$—$CH_2$—COO⁻, or —C(=O)—NH—$(CH_2)_{1-3}$—$N^+R^1R^2$—$CH_2$—CH(OH)—$CH_2$—O$_{(0\ or\ 1)}$—(S or P)$O_3^-$, and $R^1$ and $R^2$ are each, independently of one another, $C_{1-8}$-alkyl.

29. A compound according to claim 2, wherein X is a group selected from

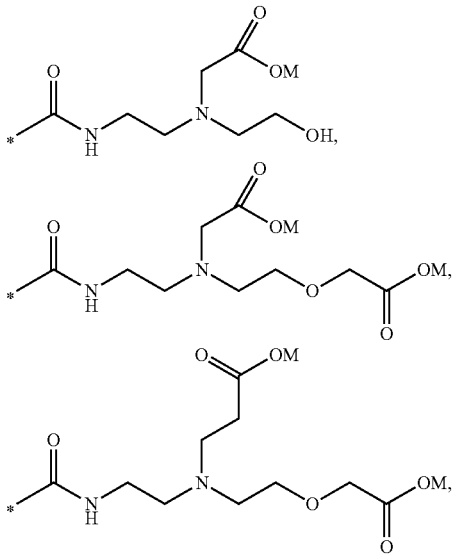

—[C(=O)—NH—$(CH_2)_{(1-8)}]_{(0\ or\ 1)}$—$N^+R^1R^2$—O⁻,
—NH—$CH_2$—COOM,
—NH—$CH_2$—$CH_2$—COOM,

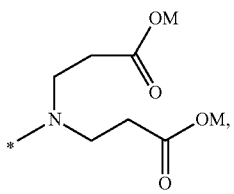

—[(C(=O)—NH—$(CH_2)_{(1-8)}]_{(0\ or\ 1)}$—$N^+R^1R^2$—$CH_2$—COO⁻, or
—C(=O)—NH—$(CH_2)_{1-3}$—$N^+R^1R^2$—$CH_2$—CH(OH)—$CH_2$—O$_{(0\ or\ 1)}$—(S or P)$O_3^-$, and
$R^1$ and $R^2$ are each, independently of one another, $C_{1-8}$-alkyl.

30. A composition comprising at least one surface-active compound according to claim 2, a suitable carrier, and optionally at least one further active ingredient.

31. A composition according to claim 30 wherein said composition is a paint or coating composition, fire-extinguishing composition, lubricant, washing or cleaning composition, de-icer or hydrophobicising composition for textile finishing or glass treatment.

32. A compound according to claim 1, wherein said compound is:
$CF_3$—O—$(CH_2)_4$—$SO_3H$; $CF_3$—O—$(CH_2)_4$—O—$SO_3H$; $CF_3$—O—$(CH_2)_5$—$SO_3H$; $CF_3$—O—$(CH_2)_5$—O—$SO_3H$; $CF_3$—O—$(CH_2)_6$—$SO_3H$; $CF_3$—O—$(CH_2)_6$—O—$SO_3H$; $CF_3$—O—$(CH_2)_7$—COOH; $CF_3$—O—$(CH_2)_7$—$SO_3H$; $CF_3$—O—$(CH_2)_7$—O—$SO_3H$ $CF_3$—O—$(CH_2)_8$—$SO_3H$; $CF_3$—O—$(CH_2)_8$—O—$SO_3H$; $CF_3$—O—$(CH_2)_9$—$SO_3H$; $CF_3$—O—$(CH_2)_9$—O—$SO_3H$; $CF_3$—O—$(CH_2)_{10}$—$SO_3H$; $CF_3$—O—$(CH_2)_{10}$—O—$SO_3H$; $CF_3$—O—$(CH_2)_{11}$—

SO₃H; CF₃—O—(CH₂)₁₁—O—SO₃H; CF₃—O—(CH₂)₁₂—SO₃H; CF₃—O—(CH₂)₁₂—O—SO₃H; CF₃—O—(CH₂)₁₃—SO₃H; CF₃—O—(CH₂)₁₃—O—SO₃H; CF₃—O—(CH₂)₁₄—SO₃H; CF₃—O—(CH₂)₁₄—O—SO₃H; CF₃—O—(CH₂)₁₅—SO₃H; CF₃—O—(CH₂)₁₅—O—SO₃H; CF₃—O—(CH₂)₁₆—SO₃H; CF₃—O—(CH₂)₁₆—O—SO₃H; CF₃—O—(CH₂)₁₇—SO₃H; CF₃—O—(CH₂)₁₇—O—SO₃H CF₃—O—(CH₂)₁₈—SO₃H; CF₃—O—(CH₂)₁₈—O—SO₃H; CF₃—O—(CH₂)₁₉—SO₃H; CF₃—O—(CH₂)₁₉—O—SO₃H; CF₃—O—(CH₂)₂₀—SO₃H; CF₃—O—(CH₂)₂₀—O—SO₃H; CF₃—O—(CH₂)₂₁—SO₃H; CF₃—O—(CH₂)₂₁—O—SO₃H; CF₃—O—(CH₂)₂₂—SO₃H; CF₃—O—(CH₂)₂₂—O—SO₃H; CF₃—O—(CH₂)₂₃—SO₃H; CF₃—O—(CH₂)₂₃—O—SO₃H; CF₃—O—(CH₂)₂₄—SO₃H; or CF₃—O—(CH₂)₂₄—O—SO₃H.

33. A compound according to claim 2, wherein said compound is:

SF₅—(CH₂)₄—COOH; SF₅—(CH₂)₄—SO₃H, SF₅—(CH₂)₄—O—SO₃H; SF₅—(CH₂)₅—COOH SF₅—(CH₂)₅—SO₃H; SF₅—(CH₂)₅—O—SO₃H; SF₅—(CH₂)₆—COOH; SF₅—(CH₂)₆—SO₃H; SF₅—(CH₂)₆—O—SO₃H; SF₅—(CH₂)₇—COOH; SF₅—(CH₂)₇—SO₃H; SF₅—(CH₂)₇—O—SO₃H; SF₅—(CH₂)₈—COOH; SF₅—(CH₂)₈—SO₃H; SF₅—(CH₂)₈—O—SO₃H; SF₅—(CH₂)₉—COOH; SF₅—(CH₂)₉—SO₃H; SF₅—(CH₂)₉—O—SO₃H; SF₅—(CH₂)₁₀—COOH; SF₅—(CH₂)₁₀—SO₃H; SF₅—(CH₂)₁₀—O—SO₃H; SF₅—(CH₂)₁₁—COOH; SF₅—(CH₂)₁₁—SO₃H; SF₅—(CH₂)₁₁—O—SO₃H; SF₅—(CH₂)₁₂—COOH; SF₅—(CH₂)₁₂—SO₃H; SF₅—(CH₂)₁₂—O—SO₃H; SF₅—(CH₂)₁₃—COOH; SF₅—(CH₂)₁₃—SO₃H; SF₅—(CH₂)₁₃—O—SO₃H; SF₅—(CH₂)₁₄—COOH; SF₅—(CH₂)₁₄—SO₃H; SF₅—(CH₂)₁₄—O—SO₃H; SF₅—(CH₂)₁₅—COOH; SF₅—(CH₂)₁₅—SO₃H; SF₅—(CH₂)₁₅—O—SO₃H; SF₅—(CH₂)₁₆—COOH; SF₅—(CH₂)₁₆—SO₃H; SF₅—(CH₂)₁₆—O—SO₃H; SF₅—(CH₂)₁₇—COOH; SF₅—(CH₂)₁₇—SO₃H; SF₅—(CH₂)₁₇—O—SO₃H; SF₅—(CH₂)₁₈—COOH; SF₅—(CH₂₁₈—SO₃H; SF₅—(CH₂)₁₈—O—SO₃H; SF₅—(CH₂)₁₉—COOH; SF₅—(CH₂)₁₉—SO₃H; SF₅—(CH₂)₁₉—O—SO₃H; SF₅—(CH₂)₂₀—COOH; SF₅—(CH₂)₂₀—SO₃H; SF₅—(CH₂)₂₀—O—SO₃H; SF₅—(CH₂)₂₁—COOH; SF₅—(CH₂)₂₁SO₃H; SF₅—(CH₂)₂₁—O—SO₃H; SF₅—(CH₂)₂₂—COOH; SF₅—(CH₂)₂₂—SO₃H; SF₅—(CH₂)₂₂—O—SO₃H; SF₅—(CH₂)₂₃—COOH; SF₅—(CH₂)₂₃—SO₃H; SF₅—(CH₂)₂₃—O—SO₃H; SF₅—(CH₂)₂₄—COOH; SF₅—(CH₂)₂₄—SO₃H; SF₅—(CH₂)₂₄—O—SO₃H; SF₅—CH=CH—(CH₂)₄—COOH; SF₅—CH=CH—(CH₂)₄—SO₃H; SF₅—CH=CH—(CH₂)₄—O—SO₃H; SF₅—CH=CH—(CH₂)₅—COOH; SF₅—CH=CH—(CH₂)₅—SO₃H; SF₅—CH=CH—(CH₂)₅—O—SO₃H; SF₅—CH=CH—(CH₂)₆—COOH; SF₅—CH=CH—(CH₂)₆—SO₃H; SF₅—CH=CH—(CH₂)₆—O—SO₃H; SF₅—CH=CH—(CH₂)₇—COOH; SF₅—CH=CH—(CH₂)₇—SO₃H; SF₅—CH=CH—(CH₂)₇—O—SO₃H; SF₅—CH=CH—(CH₂)₈—COOH; SF₅—CH=CH—(CH₂)₈—SO₃H; SF₅—CH=CH—(CH₂)₈—O—SO₃H; SF₅—CH=CH—(CH₂)₉—COOH; SF₅—CH=CH—(CH₂)₉—SO₃H; SF₅—CH=CH—(CH₂)₉—O—SO₃H; SF₅—CH=CH—(CH₂)₁₀—COOH; SF₅—CH=CH—(CH₂)₁₀—SO₃H; SF₅—CH=CH—(CH₂)₁₀—O—SO₃H; SF₅—CH=CH—(CH₂)₁₁—COOH; SF₅—CH=CH—(CH₂)₁₁—SO₃H; SF₅—CH=CH—(CH₂)₁₁—O—SO₃H; SF₅—CH=CH—(CH₂)₁₂—COOH; SF₅—CH=CH—(CH₂)₁₂—SO₃H; SF₅—CH=CH—(CH₂)₁₂—O—SO₃H; SF₅—CH=CH—(CH₂)₁₃—COOH; SF₅—CH=CH—(CH₂)₁₃—SO₃H; SF₅—CH=CH—(CH₂)₁₃—O—SO₃H; SF₅—CH=CH—(CH₂)₁₄—COOH; SF₅—CH=CH—(CH₂)₁₄—SO₃H; SF₅—CH=CH—(CH₂)₁₄—O—SO₃H; SF₅—CH=CH—(CH₂)₁₅—COOH; SF₅—CH=CH—(CH₂)₁₅—SO₃H; SF₅—CH=CH—(CH₂)₁₅—O—SO₃H; SF₅—CH=CH—(CH₂)₁₆—COOH; SF₅—CH=CH—(CH₂)₁₆—SO₃H; SF₅—CH=CH—(CH₂)₁₆—O—SO₃H; SF₅—CH=CH—(CH₂)₁₇—COOH; SF₅—CH=CH—(CH₂)₁₇—SO₃H; SF₅—CH=CH—(CH₂)₁₇—O—SO₃H; SF₅—CH=CH—(CH₂)₁₈—COOH; SF₅—CH=CH—(CH₂)₁₈—SO₃H; SF₅—CH=CH—(CH₂)₁₈—O—SO₃H; SF₅—CH=CH—(CH₂)₁₉—COOH; SF₅—CH=CH—(CH₂)₁₉—SO₃H; SF₅—CH=CH—(CH₂)₁₉—O—SO₃H; SF₅—CH=CH—(CH₂)₂₀—COOH; SF₅—CH=CH—(CH₂)₂₀—SO₃H; SF₅—CH=CH—(CH₂)₂₀—O—SO₃H; SF₅—CH=CH—(CH₂)₂₁—COOH; SF₅—CH=CH—(CH₂)₂₁—SO₃H; SF₅—CH=CH—(CH₂)₂₁—O—SO₃H; SF₅—CH=CH—(CH₂)₂₂—COOH; SF₅—CH=CH—(CH₂)₂₂—SO₃H; SF₅—CH=CH—(CH₂)₂₂—O—SO₃H; SF₅—CH=CH—(CH₂)₂₃—COOH; SF₅—CH=CH—(CH₂)₂₃—SO₃H; SF₅—CH=CH—(CH₂)₂₃—O—SO₃H; SF₅—CH=CH—(CH₂)₂₄—COOH; SF₅—CH=CH—(CH₂)₂₄—SO₃H; SF₅—CH=CH—(CH₂)₂₄—O—SO₃H; SF₅—CH₂CHBr—(CH₂)₄—COOH; SF₅—CH₂CHBr—(CH₂)₄—SO₃H; SF₅—CH₂CHBr—(CH₂)₄—O—SO₃H; SF₅—CH₂CHBr—(CH₂)₅—COOH; SF₅—CH₂CHBr—(CH₂)₅—SO₃H; SF₅—CH₂CHBr—(CH₂)₅—O—SO₃H; SF₅—CH₂CHBr—(CH₂)₆—COOH; SF₅—CH₂CHBr—(CH₂)₆—SO₃H; SF₅—CH₂CHBr—(CH₂)₆—O—SO₃H; SF₅—CH₂CHBr—(CH₂)₇—COOH; SF₅—CH₂CHBr—(CH₂)₇—SO₃H; SF₅—CH₂CHBr—(CH₂)₇—O—SO₃H; SF₅—CH₂CHBr—(CH₂)₈—COOH; SF₅—CH₂CHBr—(CH₂)₈—SO₃H; SF₅—CH₂CHBr—(CH₂)₈—O—SO₃H; SF₅—CH₂CHBr—(CH₂)₉—COOH; SF₅—CH₂CHBr—(CH₂)₉—SO₃H; SF₅—CH₂CHBr—(CH₂)₉—O—SO₃H; SF₅—CH₂CHBr—(CH₂)₁₀—COOH; SF₅—CH₂CHBr—(CH₂)₁₀—SO₃H; SF₅—CH₂CHBr—(CH₂)₁₀—O—SO₃H; SF₅—CH₂CHBr—(CH₂)₁₁—COOH; SF₅—CH₂CHBr—(CH₂)₁₁—SO₃H; SF₅—CH₂CHBr—(CH₂)₁₁—O—SO₃H; SF₅—CH₂CHBr—(CHA₂₁₂—COOH; SF₅—CH₂CHBr—(CH₂)₁₂—SO₃H; SF₅—CH₂CHBr—(CH₂)₁₂—O—SO₃H; SF₅—CH₂CHBr—(CH₂)₁₃—COOH; SF₅—CH₂CHBr—(CH₂)₁₃—SO₃H; SF₅—CH₂CHBr—(CH₂)₁₃—O—SO₃H; SF₅—CH₂CHBr—(CH₂)₁₄—COOH; SF₅—CH₂CHBr—(CH₂)₁₄—SO₃H; SF₅—CH₂CHBr—(CH₂)₁₄—O—SO₃H; SF₅—CH₂CHBr—(CH₂)₁₅—COOH; SF₅—CH₂CHBr—(CH₂)₁₅—SO₃H; SF₅—CH₂CHBr—(CH₂)₁₅—O—SO₃H; SF₅—CH₂CHBr—(CH₂)₁₆—COOH; SF₅—CH₂CHBr—(CH₂)₁₆—SO₃H; SF₅—CH₂CHBr—(CH₂)₁₆—O—SO₃H; SF₅—CH₂CHBr—(CH₂)₁₇—COOH; SF₅—CH₂CHBr—(CH₂)₁₇—SO₃H; SF₅—CH₂CHBr—(CH₂)₁₇—O—SO₃H; SF₅—CH₂CHBr—(CH₂)₁₈—COOH; SF₅—CH₂CHBr—(CH₂)₁₈—SO₃H; SF₅—CH₂CHBr—(CH₂)₁₈—O—SO₃H; SF₅—CH₂CHBr—(CH₂)₁₉—COOH; SF₅—CH₂CHBr—(CH₂)₁₉—SO₃H; SF₅—CH₂CHBr—(CH₂)₁₉—O—SO₃H; SF₅—CH₂CHBr—(CH₂)₂₀—COOH; SF₅—CH₂CHBr—(CH₂)₂₀—SO₃H; SF₅—CH₂CHBr—(CH₂)₂₀—O—SO₃H; SF₅—CH₂CHBr—(CH₂)₂₁—

COOH; $SF_5-CH_2CHBr-(CH_2)_{21}-SO_3H$; $SF_5-CH_2CHBr-(CH_2)_{21}-O-SO_3H$; $SF_5-CH_2CHBr-(CH_2)_{22}-COOH$; $SF_5-CH_2CHBr-(CH_2)_{22}-SO_3H$; $SF_5-CH_2CHBr-(CH_2)_{22}-O-SO_3H$; $SF_5-CH_2CHBr-(CH_2)_{23}-COOH$; $SF_5-CH_2CHBr-(CH_2)_{23}-SO_3H$; $SF_5-CH_2CHBr-(CH_2)_{23}-O-SO_3H$; $SF_5-CH_2CHBr-(CH_2)_{24}-COOH$; $SF_5-CH_2CHBr-(CH_2)_{24}-SO_3H$; or $SF_5-CH_2CHBr-(CH_2)_{24}-O-SO_3H$.

34. A compound according to claim 1, wherein said compound is:

$CF_3-O-(CH_2)_4-OH$; $CF_3-O-(CH_2)_5-OH$; $CF_3-O-(CH_2)_6-OH$; $CF_3-O-(CH_2)_7-OH$; $CF_3-O-(CH_2)_8-H$; $CF_3-O-(CH_2)_9-OH$; $CF_3-O-(CH_2)_{10}-OH$; $CF_3-O-(CH_2)_{11}-OH$; $CF_3-O-(CH_2)_{12}-OH$; $CF_3-O-(CH_2)_{13}-OH$; $CF_3-O-(CH_2)_{14}-OH$; $CF_3-O-(CH_2)_{15}-OH$; $CF_3-O-(CH_2)_{16}-OH$; $CF_3-O-(CH_2)_{17}-OH$; $CF_3-O-(CH_2)_{18}-OH$; $CF_3-O-(CH_2)_{19}-OH$; $CF_3-O-(CH_2)_{20}-OH$; $CF_3-O-(CH_2)_{21}-OH$; $CF_3-O-(CH_2)_{22}-OH$; $CF_3-O-(CH_2)_{23}-OH$; or $CF_3-O-(CH_2)_{24}-OH$.

35. A compound according to claim 1, wherein said compound is:

$CF_3-O-(CH_2)_4-(OCH_2CH_2)_m-OCOCH=CH_2$;
$CF_3-O-(CH_2)_4-(OCH_2CH_2)_m-OCH=CH_2$;
$CF_3-O-(CH_2)_4-(OCH_2CH_2)_m-OAr(NCO)_p$;
$CF_3-O-(CH_2)_5-(OCH_2CH_2)_m-OCOCH=CH_2$;
$CF_3-O-(CH_2)_5-(OCH_2CH_2)_m-OCH=CH_2$;
$CF_3-O-(CH_2)_5-(OCH_2CH_2)_m-OAr(NCO)_p$;
$CF_3-O-(CH_2)_6-(OCH_2CH_2)_m-OCOCH=CH_2$;
$CF_3-O-(CH_2)_6-(OCH_2CH_2)_m-OCH=CH_2$;
$CF_3-O-(CH_2)_6-(OCH_2CH_2)_m-OAr(NCO)_p$;
$CF_3-O-(CH_2)_7-(OCH_2CH_2)_m-OCOCH=CH_2$;
$CF_3-O-(CH_2)_7-(OCH_2CH_2)_m-OCH=CH_2$;
$CF_3-O-(CH_2)_7-(OCH_2CH_2)_m-OAr(NCO)_p$;
$CF_3-O-(CH_2)_8-(OCH_2CH_2)_m-OCOCH=CH_2$;
$CF_3-O-(CH_2)_8-(OCH_2CH_2)_m-OCH=CH_2$;
$CF_3-O-(CH_2)_8-(OCH_2CH_2)_m-OAr(NCO)_p$;
$CF_3-O-(CH_2)_9-(OCH_2CH_2)_m-OCOCH=CH_2$;
$CF_3-O-(CH_2)_9-(OCH_2CH_2)_m-OCH=CH_2$;
$CF_3-O-(CH_2)_9-(OCH_2CH_2)_m-OAr(NCO)_p$;
$CF_3-O-(CH_2)_{10}-(OCH_2CH_2)_m-OCOCH=CH_2$;
$CF_3-O-(CH_2)_{10}-(OCH_2CH_2)_m-OCH=CH_2$;
$CF_3-O-(CH_2)_{10}-(OCH_2CH_2)_m-OAr(NCO)_p$;
$CF_3-O-(CH_2)_{11}-(OCH_2CH_2)_m-OCOCH=CH_2$;
$CF_3-O-(CH_2)_{11}-(OCH_2CH_2)_m-OCH=CH_2$;
$CF_3-O-(CH_2)_{11}-(OCH_2CH_2)_m-OAr(NCO)_p$;
$CF_3-O-(CH_2)_{12}-(OCH_2CH_2)_m-OCOCH=CH_2$;
$CF_3-O-(CH_2)_{12}-(OCH_2CH_2)_m-OCH=CH_2$;
$CF_3-O-(CH_2)_{12}-(OCH_2CH_2)_m-OAr(NCO)_p$;
$CF_3-O-(CH_2)_{13}-(OCH_2CH_2)_m-OCOCH=CH_2$;
$CF_3-O-(CH_2)_{13}-(OCH_2CH_2)_m-OCH=CH_2$;
$CF_3-O-(CH_2)_{13}-(OCH_2CH_2)_m-OAr(NCO)_p$;
$CF_3-O-(CH_2)_{14}-(OCH_2CH_2)_m-OCOCH=CH_2$;
$CF_3-O-(CH_2)_{14}-(OCH_2CH_2)_m-OCH=CH_2$;
$CF_3-O-(CH_2)_{14}-(OCH_2CH_2)_m-OAr(NCO)_p$;
$CF_3-O-(CH_2)_{15}-(OCH_2CH_2)_m-OCOCH=CH_2$;
$CF_3-O-(CH_2)_{15}-(OCH_2CH_2)_m-OCH=CH_2$;
$CF_3-O-(CH_2)_{15}-(OCH_2CH_2)_m-OAr(NCO)_p$;
$CF_3-O-(CH_2)_{16}-(OCH_2CH_2)_m-OCOCH=CH_2$;
$CF_3-O-(CH_2)_{16}-(OCH_2CH_2)_m-OCH=CH_2$;
$CF_3-O-(CH_2)_{16}-(OCH_2CH_2)_m-OAr(NCO)_p$;
$CF_3-O-(CH_2)_{17}-(OCH_2CH_2)_m-OCOCH=CH_2$;
$CF_3-O-(CH_2)_{17}-(OCH_2CH_2)_m-OCH=CH_2$;
$CF_3-O-(CH_2)_{17}-(OCH_2CH_2)_m-OAr(NCO)_p$;
$CF_3-O-(CH_2)_{18}-(OCH_2CH_2)_m-OCOCH=CH_2$;
$CF_3-O-(CH_2)_{18}-(OCH_2CH_2)_m-OCH=CH_2$;
$CF_3-O-(CH_2)_{18}-(OCH_2CH_2)_m-OAr(NCO)_p$;
$CF_3-O-(CH_2)_{19}-(OCH_2CH_2)_m-OCOCH=CH_2$;
$CF_3-O-(CH_2)_{19}-(OCH_2CH_2)_m-OCH=CH_2$;
$CF_3-O-(CH_2)_{19}-(OCH_2CH_2)_m-OAr(NCO)_p$;
$CF_3-O-(CH_2)_{20}-(OCH_2CH_2)_m-OCOCH=CH_2$;
$CF_3-O-(CH_2)_{20}-(OCH_2CH_2)_m-OCH=CH_2$;
$CF_3-O-(CH_2)_{20}-(OCH_2CH_2)_m-OAr(NCO)_p$;
$CF_3-O-(CH_2)_{21}-(OCH_2CH_2)_m-OCOCH=CH_2$;
$CF_3-O-(CH_2)_{21}-(OCH_2CH_2)_m-OCH=CH_2$;
$CF_3-O-(CH_2)_{21}-(OCH_2CH_2)_m-OAr(NCO)_p$;
$CF_3-O-(CH_2)_{22}-(OCH_2CH_2)_m-OCOCH=CH_2$;
$CF_3-O-(CH_2)_{22}-(OCH_2CH_2)_m-OCH=CH_2$;
$CF_3-O-(CH_2)_{22}-(OCH_2CH_2)_m-OAr(NCO)_p$;
$CF_3-O-(CH_2)_{23}-(OCH_2CH_2)_m-OCOCH=CH_2$;
$CF_3-O-(CH_2)_{23}-(OCH_2CH_2)_m-OCH=CH_2$;
$CF_3-O-(CH_2)_{23}-(OCH_2CH_2)_m-OAr(NCO)_p$;
$CF_3-O-(CH_2)_{24}-(OCH_2CH_2)_m-OCOCH=CH_2$;
$CF_3-O-(CH_2)_{24}-(OCH_2CH_2)_m-OCH=CH_2$; or
$CF_3-O-(CH_2)_{24}-(OCH_2CH_2)_m-OAr(NCO)_p$;

wherein m is an integer from the range 0 to 1000, and p is 1 or 2.

36. A compound according to claim 2, wherein said compound is:

$SF_5-(CH_2)_4-(OCH_2CH_2)_m-OCOCH=CH_2$;
$SF_5-(CH_2)_4-(OCH_2CH_2)_m-OCH=CH_2$;
$SF_5-(CH_2)_4-(OCH_2CH_2)_m-OAr(NCO)_p$;
$SF_5-(CH_2)_5-(OCH_2CH_2)_m-OCOCH=CH_2$;
$SF_5-(CH_2)_5-(OCH_2CH_2)_m-OCH=CH_2$;
$SF_5-(CH_2)_5-(OCH_2CH_2)_m-OAr(NCO)_p$;
$SF_5-(CH_2)_6-(OCH_2CH_2)_m-OCOCH=CH_2$;
$SF_5-(CH_2)_6-(OCH_2CH_2)_m-OCH=CH_2$;
$SF_5-(CH_2)_6-(OCH_2CH_2)_m-OAr(NCO)_p$;
$SF_5-(CH_2)_7-(OCH_2CH_2)_m-OCOCH=CH_2$;
$SF_5-(CH_2)_7-(OCH_2CH_2)_m-OCH=CH_2$;
$SF_5-(CH_2)_7-(OCH_2CH_2)_m-OAr(NCO)_p$;
$SF_5-(CH_2)_8-(OCH_2CH_2)_m-OCOCH=CH_2$;
$SF_5-(CH_2)_8-(OCH_2CH_2)_m-OCH=CH_2$;
$SF_5-(CH_2)_8-(OCH_2CH_2)_m-OAr(NCO)_p$;
$SF_5-(CH_2)_9-(OCH_2CH_2)_m-OCOCH=CH_2$;
$SF_5-(CH_2)_9-(OCH_2CH_2)_m-OCH=CH_2$;
$SF_5-(CH_2)_9-(OCH_2CH_2)_m-OAr(NCO)_p$;
$SF_5-(CH_2)_{10}-(OCH_2CH_2)_m-OCOCH=CH_2$;
$SF_5-(CH_2)_{10}-(OCH_2CH_2)_m-OCH=CH_2$;
$SF_5-(CH_2)_{10}-(OCH_2CH_2)_m-OAr(NCO)_p$;
$SF_5-(CH_2)_{11}-(OCH_2CH_2)_m-OCOCH=CH_2$;
$SF_5-(CH_2)_{11}-(OCH_2CH_2)_m-OCH=CH_2$;
$SF_5-(CH_2)_{11}-(OCH_2CH_2)_m-OAr(NCO)_p$;
$SF_5-(CH_2)_{12}-(OCH_2CH_2)_m-OCOCH=CH_2$;
$SF_5-(CH_2)_{12}-(OCH_2CH_2)_m-OCH=CH_2$;
$SF_5-(CH_2)_{12}-(OCH_2CH_2)_m-OAr(NCO)_p$;
$SF_5-(CH_2)_{13}-(OCH_2CH_2)_m-OCOCH=CH_2$;
$SF_5-(CH_2)_{13}-(OCH_2CH_2)_m-OCH=CH_2$;
$SF_5-(CH_2)_{13}-(OCH_2CH_2)_m-OAr(NCO)_p$;
$SF_5-(CH_2)_{14}-(OCH_2CH_2)_m-OCOCH=CH_2$;
$SF_5-(CH_2)_{14}-(OCH_2CH_2)_m-OCH=CH_2$;
$SF_5-(CH_2)_{14}-(OCH_2CH_2)_m-OAr(NCO)_p$;
$SF_5-(CH_2)_{15}-(OCH_2CH_2)_m-OCOCH=CH_2$;
$SF_5-(CH_2)_{15}-(OCH_2CH_2)_m-OCH=CH_2$;
$SF_5-(CH_2)_{15}-(OCH_2CH_2)_m-OAr(NCO)_p$;
$SF_5-(CH_2)_{16}-(OCH_2CH_2)_m-OCOCH=CH_2$;
$SF_5-(CH_2)_{16}-(OCH_2CH_2)_m-OCH=CH_2$;
$SF_5-(CH_2)_{16}-(OCH_2CH_2)_m-OAr(NCO)_p$;
$SF_5-(CH_2)_{17}-(OCH_2CH_2)_m-OCOCH=CH_2$;
$SF_5-(CH_2)_{17}-(OCH_2CH_2)_m-OCH=CH_2$;
$SF_5-(CH_2)_{17}-(OCH_2CH_2)_m-OAr(NCO)_p$;
$SF_5-(CH_2)_{18}-(OCH_2CH_2)_m-OCOCH=CH_2$;
$SF_5-(CH_2)_{18}-$ $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $(OCH_2CH_2)_m$—OCOCH=$CH_2$; $(OCH_2CH_2)_m$—OCH=$CH_2$; $(OCH_2CH_2)_m$—OAr(NCO)$_p$; $SF_5$—CH=CH—$(CH_2)_4$—$(OCH_2CH_2)_m$—OCOCH=$CH_2$; $SF_5$—CH=CH—$(CH_2)_4$—$(OCH_2CH_2)_m$—OCH=$CH_2$; $SF_5$—CH=CH—$(CH_2)_4$—$(OCH_2CH_2)_m$—OAr(NCO)$_p$; $SF_5$—CH=CH—$(CH_2)_5$—$(OCH_2CH_2)_m$—OCOCH=$CH_2$; $SF_5$—CH=CH—$(CH_2)_5$—$(OCH_2CH_2)_m$—OCH=$CH_2$; $SF_5$—CH=CH—$(CH_2)_5$—$(OCH_2CH_2)_m$—OAr(NCO)$_p$; $SF_5$—CH=CH—$(CH_2)_6$—$(OCH_2CH_2)_m$—OCOCH=$CH_2$; $SF_5$—CH=CH—$(CH_2)_6$—$(OCH_2CH_2)_m$—OCH=$CH_2$; $SF_5$—CH=CH—$(CH_2)_6$—$(OCH_2CH_2)_m$—OAr(NCO)$_p$; $SF_5$—CH=CH—$(CH_2)_7$—$(OCH_2CH_2)_m$—OCOCH=$CH_2$; $SF_5$—CH=CH—$(CH_2)_7$—$(OCH_2CH_2)_m$—OCH=$CH_2$; $SF_5$—CH=CH—$(CH_2)_7$—$(OCH_2CH_2)_m$—OAr(NCO)$_p$; $SF_5$—CH=CH—$(CH_2)_8$—$(OCH_2CH_2)_m$—OCOCH=$CH_2$; $SF_5$—CH=CH—$(CH_2)_8$—$(OCH_2CH_2)_m$—OCH=$CH_2$; $SF_5$—CH=CH—$(CH_2)_8$—$(OCH_2CH_2)_m$—OAr(NCO)$_p$; $SF_5$—CH=CH—$(CH_2)_9$—$(OCH_2CH_2)_m$—OCOCH=$CH_2$; $SF_5$—CH=CH—$(CH_2)_9$—$(OCH_2CH_2)_m$—OCH=$CH_2$; $SF_5$—CH=CH—$(CH_2)_9$—$(OCH_2CH_2)_m$—OAr(NCO)$_p$; $SF_5$—CH=CH—$(CH_2)_{10}$—$(OCH_2CH_2)_m$—OCOCH=$CH_2$; $SF_5$—CH=CH—$(CH_2)_{10}$—$(OCH_2CH_2)_m$—OCH=$CH_2$; $SF_5$—CH=CH—$(CH_2)_{10}$—$(OCH_2CH_2)_m$—OAr(NCO)$_p$; $SF_5$—CH=CH—$(CH_2)_{11}$—$(OCH_2CH_2)_m$—OCOCH=$CH_2$; $SF_5$—CH=CH—$(CH_2)_{11}$—$(OCH_2CH_2)_m$—OCH=$CH_2$; $SF_5$—CH=CH—$(CH_2)_{11}$—$(OCH_2CH_2)_m$—OAr(NCO)$_p$; $SF_5$—CH=CH—$(CH_2)_{12}$—$(OCH_2CH_2)_m$—OCOCH=$CH_2$; $SF_5$—CH=CH—$(CH_2)_{12}$—$(OCH_2CH_2)_m$—OCH=$CH_2$; $SF_5$—CH=CH—$(CH_2)_{12}$—$(OCH_2CH_2)_m$—OAr(NCO)$_p$; $SF_5$—CH=CH—$(CH_2)_{13}$—$(OCH_2CH_2)_m$—OCOCH=$CH_2$; $SF_5$—CH=CH—$(CH_2)_{13}$—$(OCH_2CH_2)_m$—OCH=$CH_2$; $SF_5$—CH=CH—$(CH_2)_{13}$—$(OCH_2CH_2)_m$—OAr(NCO)$_p$; $SF_5$—CH=CH—$(CH_2)_{14}$—$(OCH_2CH_2)_m$—OCOCH=$CH_2$; $SF_5$—CH=CH—$(CH_2)_{14}$—$(OCH_2CH_2)_m$—OCH=$CH_2$; $SF_5$—CH=CH—$(CH_2)_{14}$—$(OCH_2CH_2)_m$—OAr(NCO)$_p$; $SF_5$—CH=CH—$(CH_2)_{15}$—$(OCH_2CH_2)_m$—OCOCH=$CH_2$; $SF_5$—CH=CH—$(CH_2)_{15}$—$(OCH_2CH_2)_m$—OCH=$CH_2$; $SF_5$—CH=CH—$(CH_2)_{15}$—$(OCH_2CH_2)_m$—OAr(NCO)$_p$; $SF_5$—CH=CH—$(CH_2)_{16}$—$(OCH_2CH_2)_m$—OCOCH=$CH_2$; $SF_5$—CH=CH—$(CH_2)_{16}$—$(OCH_2CH_2)_m$—OCH=$CH_2$; $SF_5$—CH=CH—$(CH_2)_{16}$—$(OCH_2CH_2)_m$—OAr(NCO)$_p$; $SF_5$—CH=CH—$(CH_2)_{14}$—$(OCH_2CH_2)_m$—OCOCH=$CH_2$; $SF_5$—$(CH_2)_{18}$— $SF_5$—$(CH_2)_{19}$— $SF_5$—$(CH_2)_{19}$— $SF_5$—$(CH_2)_{19}$— $SF_5$—$(CH_2)_{20}$— $SF_5$—$(CH_2)_{20}$— $SF_5$—$(CH_2)_{20}$— $SF_5$—$(CH_2)_{21}$— $SF_5$—$(CH_2)_{21}$— $SF_5$—$(CH_2)_{21}$— $SF_5$—$(CH_2)_{22}$— $SF_5$—$(CH_2)_{22}$— $SF_5$—$(CH_2)_{22}$— $SF_5$—$(CH_2)_{23}$— $SF_5$—$(CH_2)_{23}$— $SF_5$—$(CH_2)_{23}$— $SF_5$—$(CH_2)_{24}$— $SF_5$—$(CH_2)_{24}$— $SF_5$—$(CH_2)_{24}$—

$(OCH_2CH_2)_m$—OCH=$CH_2$; $SF_5$—CH=CH—$(CH_2)_{14}$—$(OCH_2CH_2)_m$—OAr(NCO)$_p$; $SF_5$—CH=CH—$(CH_2)_{15}$—$(OCH_2CH_2)_m$—OCOCH=$CH_2$; $SF_5$—CH=CH—$(CH_2)_{15}$—$(OCH_2CH_2)_m$—OCH=$CH_2$; $SF_5$—CH=CH—$(CH_2)_{15}$—$(OCH_2CH_2)_m$—OAr(NCO)$_p$; $SF_5$—CH=CH—$(CH_2)_{16}$—$(OCH_2CH_2)_m$—OCOCH=$CH_2$; $SF_5$—CH=CH—$(CH_2)_{16}$—$(OCH_2CH_2)_m$—OCH=$CH_2$; $SF_5$—CH=CH—$(CH_2)_{16}$—$(OCH_2CH_2)_m$—OAr(NCO)$_p$; $SF_5$—CH=CH—$(CH_2)_{17}$—$(OCH_2CH_2)_m$—OCOCH=$CH_2$; $SF_5$—CH=CH—$(CH_2)_{17}$—$(OCH_2CH_2)_m$—OCH=$CH_2$; $SF_5$—CH=CH—$(CH_2)_{20}$—$(OCH_2CH_2)_m$—OAr(NCO)$_p$; $SF_5$—CH=CH—$(CH_2)_{21}$—$(OCH_2CH_2)_m$—OCOCH=$CH_2$; $SF_5$—CH=CH—$(CH_2)_{18}$—$(OCH_2CH_2)_m$—OCH=$CH_2$; $SF_5$—CH=CH—$(CH_2)_{18}$—$(OCH_2CH_2)_m$—OAr(NCO)$_p$; $SF_5$—CH=CH—$(CH_2)_{19}$—$(OCH_2CH_2)_m$—OCOCH=$CH_2$; $SF_5$—CH=CH—$(CH_2)_{19}$—$(OCH_2CH_2)_m$—OCH=$CH_2$; $SF_5$—CH=CH—$(CH_2)_{19}$—$(OCH_2CH_2)_m$—OAr(NCO)$_p$; $SF_5$—CH=CH—$(CH_2)_{20}$—$(OCH_2CH_2)_m$—OCOCH=$CH_2$; $SF_5$—CH=CH—$(CH_2)_{20}$—$(OCH_2CH_2)_m$—OCH=$CH_2$; $SF_5$—CH=CH—$(CH_2)_{23}$—$(OCH_2CH_2)_m$—OAr(NCO)$_p$; $SF_5$—CH=CH—$(CH_2)_{24}$—$(OCH_2CH_2)_m$—OCOCH=$CH_2$; $SF_5$—CH=CH—$(CH_2)_{21}$—$(OCH_2CH_2)_m$—OCH=$CH_2$; $SF_5$—CH=CH—$(CH_2)_{21}$—$(OCH_2CH_2)_m$—OAr(NCO)$_p$; $SF_5$—CH=CH—$(CH_2)_{22}$—$(OCH_2CH_2)_m$—OCOCH=$CH_2$; $SF_5$—CH=CH—$(CH_2)_{22}$—$(OCH_2CH_2)_m$—OCH=$CH_2$; $SF_5$—CH=CH—$(CH_2)_{22}$—$(OCH_2CH_2)_m$—OAr(NCO)$_p$; $SF_5$—CH=CH—$(CH_2)_{23}$—$(OCH_2CH_2)_m$—OCOCH=$CH_2$; $SF_5$—CH=CH—$(CH_2)_{23}$—$(OCH_2CH_2)_m$—OCH=$CH_2$; $SF_5$—CH=CH—$(CH_2)_{23}$—$(OCH_2CH_2)_m$—OAr(NCO)$_p$; $SF_5$—CH=CH—$(CH_2)_{24}$—$(OCH_2CH_2)_m$—OCOCH=$CH_2$; $SF_5$—CH=CH—$(CH_2)_{24}$—$(OCH_2CH_2)_m$—OCH=$CH_2$; $SF_5$—CH=CH—$(CH_2)_{24}$—$(OCH_2CH_2)_m$—OAr(NCO)$_p$; $SF_5$—$CH_2$CHBr—$(CH_2)_4$—$(OCH_2CH_2)_m$—OCOCH=$CH_2$; $SF_5$—$CH_2$CHBr—$(CH_2)_4$—$(OCH_2CH_2)_m$—OCH=$CH_2$; $SF_5$—$CH_2$CHBr—$(CH_2)_4$—$(OCH_2CH_2)_m$—OAr(NCO)$_p$; $SF_5$—$CH_2$CHBr—$(CH_2)_5$—$(OCH_2CH_2)_m$—OCOCH=$CH_2$; $SF_5$—$CH_2$CHBr—$(CH_2)_5$—$(OCH_2CH_2)_m$—OCH=$CH_2$; $SF_5$—$CH_2$CHBr—$(CH_2)_5$—$(OCH_2CH_2)_m$—OAr(NCO)$_p$; $SF_5$—$CH_2$CHBr—$(CH_2)_6$—$(OCH_2CH_2)_m$—OCOCH=$CH_2$; $SF_5$—$CH_2$CHBr—$(CH_2)_6$—$(OCH_2CH_2)_m$—OCH=$CH_2$; $SF_5$—$CH_2$CHBr—$(CH_2)_6$—$(OCH_2CH_2)_m$—OAr(NCO)$_p$; $SF_5$—$CH_2$CHBr—$(CH_2)_7$—$(OCH_2CH_2)_m$—OCOCH=$CH_2$; $SF_5$—$CH_2$CHBr—$(CH_2)_7$—$(OCH_2CH_2)_m$—OCH=$CH_2$; $SF_5$—$CH_2$CHBr—$(CH_2)_7$—$(OCH_2CH_2)_m$—OAr(NCO)$_p$; $SF_5$—$CH_2$CHBr—$(CH_2)_8$—$(OCH_2CH_2)_m$—OCOCH=$CH_2$; $SF_5$—$CH_2$CHBr—$(CH_2)_8$—$(OCH_2CH_2)_m$—OCH=$CH_2$; $SF_5$—$CH_2$CHBr—$(CH_2)_8$—$(OCH_2CH_2)_m$—OAr(NCO)$_p$; $SF_5$—$CH_2$CHBr—$(CH_2)_9$—$(OCH_2CH_2)_m$—OCOCH=$CH_2$; $SF_5$—$CH_2$CHBr—$(CH_2)_9$—$(OCH_2CH_2)_m$—OCH=$CH_2$; $SF_5$—$CH_2$CHBr—$(CH_2)_9$—$(OCH_2CH_2)_m$—OAr(NCO)$_p$; $SF_5$—$CH_2$CHBr—$(CH_2)_{10}$—$(OCH_2CH_2)_m$—

OCOCH=CH$_2$; SF$_5$—CH$_2$CHBr—(CH$_2$)$_{10}$—(OCH$_2$CH$_2$)$_m$—OCH=CH$_2$; SF$_5$—CH$_2$CHBr—(CH$_2$)$_{10}$—(OCH$_2$CH$_2$)$_m$—OAr(NCO)$_p$; SF$_5$—CH$_2$CHBr—(CH$_2$)$_{11}$—(OCH$_2$CH$_2$)$_m$—OCOCH=CH$_2$; SF$_5$—CH$_2$CHBr—(CH$_2$)$_{11}$—(OCH$_2$CH$_2$)$_m$—OCH=CH$_2$; SF$_5$—CH$_2$CHBr—(CH$_2$)$_{11}$—(OCH$_2$CH$_2$)$_m$—OAr(NCO)$_p$; SF$_5$—CH$_2$CHBr—(CH$_2$)$_{12}$—(OCH$_2$CH$_2$)$_m$—COCH=CH$_2$; SF$_5$—CH$_2$CHBr—(CH$_2$)$_{12}$—(OCH$_2$CH$_2$)$_m$—OCH=CH$_2$; SF$_5$—CH$_2$CHBr—(CH$_2$)$_{13}$—(OCH$_2$CH$_2$)$_m$—OAr(NCO)$_p$; SF$_5$—CH$_2$CHBr—(CH$_2$)$_{13}$—(OCH$_2$CH$_2$)$_m$—OCOCH=CH$_2$; SF$_5$—CH$_2$CHBr—(CH$_2$)$_{13}$—(OCH$_2$CH$_2$)$_m$—OCH=CH$_2$; SF$_5$—CH$_2$CHBr—(CH$_2$)$_{13}$—(OCH$_2$CH$_2$)$_m$—OAr(NCO)$_p$; SF$_5$—CH$_2$CHBr—(CH$_2$)$_{14}$—(OCH$_2$CH$_2$)$_m$—OCOCH=CH$_2$; SF$_5$—CH$_2$CHBr—(CH$_2$)$_{14}$—(OCH$_2$CH$_2$)$_m$—OCH=CH$_2$; SF$_5$—CH$_2$CHBr—(CH$_2$)$_{14}$—(OCH$_2$CH$_2$)$_m$—OAr(NCO)$_p$; SF$_5$—CH$_2$CHBr—(CH$_2$)$_{15}$—(OCH$_2$CH$_2$)$_m$—OCOCH=CH$_2$; SF$_5$—CH$_2$CHBr—(CH$_2$)$_{15}$—(OCH$_2$CH$_2$)$_m$—OCH=CH$_2$; SF$_5$—CH$_2$CHBr—(CH$_2$)$_{15}$—(OCH$_2$CH$_2$)$_m$—OAr(NCO)$_p$; SF$_5$—CH$_2$CHBr—(CH$_2$)$_{16}$—(OCH$_2$CH$_2$)$_m$—OCOCH=CH$_2$; SF$_5$—CH$_2$CHBr—(CH$_2$)$_{16}$—(OCH$_2$CH$_2$)$_m$—OCH=CH$_2$; SF$_5$—CH$_2$CHBr—(CH$_2$)$_{16}$—(OCH$_2$CH$_2$)$_m$—OAr(NCO)$_p$; SF$_5$—CH$_2$CHBr—(CH$_2$)$_{17}$—(OCH$_2$CH$_2$)$_m$—OCOCH=CH$_2$; SF$_5$—CH$_2$CHBr—(CH$_2$)$_{17}$—(OCH$_2$CH$_2$)$_m$—OCH=CH$_2$; SF$_5$—CH$_2$CHBr—(CH$_2$)$_{17}$—(OCH$_2$CH$_2$)$_m$—OAr(NCO)$_p$; SF$_5$—CH$_2$CHBr—(CH$_2$)$_{18}$—(OCH$_2$CH$_2$)$_m$—OCOCH=CH$_2$; SF$_5$—CH$_2$CHBr—(CH$_2$)$_{18}$—(OCH$_2$CH$_2$)$_m$—OCH=CH$_2$; SF$_5$—CH$_2$CHBr—(CH$_2$)$_{18}$—(OCH$_2$CH$_2$)$_m$—OAr(NCO)$_p$; SF$_5$—CH$_2$CHBr—(CH$_2$)$_{19}$—(OCH$_2$CH$_2$)$_m$—OCOCH=CH$_2$; SF$_5$—CH$_2$CHBr—(CH$_2$)$_{19}$—(OCH$_2$CH$_2$)$_m$—OCH=CH$_2$; SF$_5$—CH$_2$CHBr—(CH$_2$)$_{19}$—(OCH$_2$CH$_2$)$_m$—OAr(NCO)$_p$; SF$_5$—CH$_2$CHBr—(CH$_2$)$_{20}$—(OCH$_2$CH$_2$)$_m$—OCOCH=CH$_2$; SF$_5$—CH$_2$CHBr—(CH$_2$)$_{20}$—(OCH$_2$CH$_2$)$_m$—OCH=CH$_2$; SF$_5$—CH$_2$CHBr—(CH$_2$)$_{20}$—(OCH$_2$CH$_2$)$_m$—OAr(NCO)$_p$; SF$_5$—CH$_2$CHBr—(CH$_2$)$_{21}$—(OCH$_2$CH$_2$)$_m$—OCOCH=CH$_2$; SF$_5$—CH$_2$CHBr—(CH$_2$)$_{21}$—(OCH$_2$CH$_2$)$_m$—OCH=CH$_2$; SF$_5$—CH$_2$CHBr—(CH$_2$)$_{21}$—(OCH$_2$CH$_2$)$_m$—OAr(NCO)$_p$; SF$_5$—CH$_2$CHBr—(CH$_2$)$_{22}$—(OCH$_2$CH$_2$)$_m$—OCOCH=CH$_2$; SF$_5$—CH$_2$CHBr—(CH$_2$)$_{22}$—(OCH$_2$CH$_2$)$_m$—OCH=CH$_2$; SF$_5$—CH$_2$CHBr—(CH$_2$)$_{22}$—(OCH$_2$CH$_2$)$_m$—OAr(NCO)$_p$; SF$_5$—CH$_2$CHBr—(CH$_2$)$_{23}$—(OCH$_2$CH$_2$)$_m$—OCOCH=CH$_2$; SF$_5$—CH$_2$CHBr—(CH$_2$)$_{23}$—(OCH$_2$CH$_2$)$_m$—OCH=CH$_2$; SF$_5$—CH$_2$CHBr—(CH$_2$)$_{23}$—(OCH$_2$CH$_2$)$_m$—OAr(NCO)$_p$; SF$_5$—CH$_2$CHBr—(CH$_2$)$_{24}$—(OCH$_2$CH$_2$)$_m$—OCOCH=CH$_2$; SF$_5$—CH$_2$CHBr—(CH$_2$)$_{24}$—(OCH$_2$CH$_2$)$_m$—OCH=CH$_2$; or SF$_5$—CH$_2$CHBr—(CH$_2$)$_{24}$—(OCH$_2$CH$_2$)$_m$—OAr(NCO)$_p$; p1 wherein m is an integer from the range 0 to 1000, and p is 1 or 2.

37. A compound according to claim 1, wherein said compound is:

CF$_3$—O—(CH$_2$)$_4$—N$^+$R$^1$R$^2$R$^3$Z$^-$; CF$_3$—O—(CH$_2$)$_4$—P$^+$R$^1$R$^2$R$^3$Z$^-$; CF$_3$—O—(CH$_2$)$_4$—O-glucosiede; CF$_3$—O—(CH$_2$)$_5$—N$^+$R$^1$R$^2$R$^3$Z$^-$; CF$_3$—O—(CH$_2$)$_5$—P$^+$R$^1$R$^2$R$^3$Z$^-$; CF$_3$—O—(CH$_2$)$_5$—O-glucoside; CF$_3$—O—(CH$_2$)$_6$—N$^+$R$^1$R$^2$R$^3$Z$^-$; CF$_3$—O—(CH$_2$)$_6$P$^+$R$^1$R$^2$R$^2$Z$^-$; CF$_3$—O—(CH$_2$)$_6$—O-glucosiede; CF$_3$—O—(CH$_2$)$_7$—N$^+$R$^1$R$^2$R$^3$Z$^-$; CF$_3$—O—(CH$_2$)$_7$—P$^+$R$^1$R$^2$R$^3$Z$^-$; CF$_3$—O—(CH$_2$)$_7$—O-glucosiede; CF$_3$—O—(CH$_2$)$_8$—N$^+$R$^1$R$^2$R$^3$Z$^-$; CF$_3$—O—(CH$_2$)$_8$—P$^+$R$^1$R$^2$R$^3$Z$^-$; CF$_3$—O—(CH$_2$)$_8$—O-glucosiede; CF$_3$—O—(CH$_2$)$_9$—N$^+$R$^1$R$^2$R$^3$Z$^-$; CF$_3$—O—(CH$_2$)$_9$—P$^+$R$^1$R$^2$R$^3$Z$^-$; CF$_3$—O—(CH$_2$)$_9$—O-glucosiede; CF$_3$—O—(CH$_2$)$_{10}$—N$^+$R$^1$R$^2$R$^3$Z$^-$; CF$_3$—O—(CH$_2$)$_{10}$—P$^+$R$^1$R$^2$R$^3$Z$^-$; CF$_3$—O—(CH$_2$)$_{10}$—O-glucosiede; CF$_3$—O—(CH$_2$)$_{11}$—N$^+$R$^1$R$^2$R$^3$Z$^-$; CF$_3$—O—(CH$_2$)$_{11}$—P$^+$R$^1$R$^2$R$^3$Z$^-$; CF$_3$—O—(CH$_2$)$_{11}$—O-glucosiede; CF$_3$—O—(CH$_2$)$_{12}$—N$^+$R$^1$R$^2$R$^3$Z$^-$; CF$_3$—O—(CH$_2$)$_{12}$—P$^+$R$^1$R$^2$R$^3$Z$^-$; CF$_3$—O—(CH$_2$)$_{12}$—O-glucosiede; CF$_3$—O—(CH$_2$)$_{13}$—N$^+$R$^1$R$^2$R$^3$Z$^-$; CF$_3$—O—(CH$_2$)$_{13}$—P$^+$R$^1$R$^2$R$^3$Z$^-$; CF$_3$—O—(CH$_2$)$_7$—O-glucosiede; CF$_3$—O—(CH$_2$)$_{14}$—N$^+$R$^1$R$^2$R$^3$Z$^-$; CF$_3$—O—(CH$_2$)$_{14}$—P$^+$R$^1$R$^2$R$^3$Z$^-$; CF$_3$—O—(CH$_2$)$_{14}$—O-glucosiede; CF$_3$—O—(CH$_2$)$_{15}$—N$^+$R$^1$R$^2$R$^3$Z$^-$; CF$_3$—O—(CH$_2$)$_{15}$—P$^+$R$^1$R$^2$R$^3$Z$^-$; CF$_3$—O—(CH$_2$)$_{15}$—O-glucosiede; CF$_3$—O—(CH$_2$)$_{16}$—N$^+$R$^1$R$^2$R$^3$Z$^-$; CF$_3$—O—(CH$_2$)$_{16}$—P$^+$R$^1$R$^2$R$^3$Z$^-$; CF$_3$—O—(CH$_2$)$_{16}$—O-glucosiede; CF$_3$—O—(CH$_2$)$_{17}$—N$^+$R$^1$R$^2$R$^3$Z$^-$; CF$_3$—O—(CH$_2$)$_{17}$—P$^+$R$^1$R$^2$R$^3$Z$^-$; CF$_3$—O—(CH$_2$)$_{17}$—O-glucosiede; CF$_3$—O—(CH$_2$)$_{18}$—N$^+$R$^1$R$^2$R$^3$Z$^-$; CF$_3$—O—(CH$_2$)$_{18}$—P$^+$R$^1$R$^2$R$^3$Z$^-$; CF$_3$—O—(CH$_2$)$_{18}$—O-glucosiede; CF$_3$—O—(CH$_2$)$_{19}$—N$^+$R$^1$R$^2$R$^3$Z$^-$; CF$_3$—O—(CH$_2$)$_{19}$—P$^+$R$^1$R$^2$R$^3$Z$^-$; CF$_3$—O—(CH$_2$)$_{19}$—O-glucosiede; CF$_3$—O—(CH$_2$)$_{20}$—N$^+$R$^1$R$^2$R$^3$Z$^-$; CF$_3$—O—(CH$_2$)$_{20}$—P$^+$R$^1$R$^2$R$^3$Z$^-$; CF$_3$—O—(CH$_2$)$_{20}$—O-glucosiede; CF$_3$—O—(CH$_2$)$_{21}$—N$^+$R$^1$R$^2$R$^3$Z$^-$; CF$_3$—O—(CH$_2$)$_{21}$—P$^+$R$^1$R$^2$R$^3$Z$^-$; CF$_3$—O—(CH$_2$)$_{21}$—O-glucosiede; CF$_3$—O—(CH$_2$)$_{22}$—N$^+$R$^1$R$^2$R$^3$Z$^-$; CF$_3$—O—(CH$_2$)$_{22}$—P$^+$R$^1$R$^2$R$^3$Z$^-$; CF$_3$—O—(CH$_2$)$_{22}$—O-glucosiede; CF$_3$—O—(CH$_2$)$_{23}$—N$^+$R$^1$R$^2$R$^3$Z$^-$; CF$_3$—O—(CH$_2$)$_{23}$—P$^+$R$^1$R$^2$R$^3$Z$^-$; CF$_3$—O—(CH$_2$)$_{23}$—O-glucosiede; CF$_3$—O—(CH$_2$)$_{24}$—N$^+$R$^1$R$^2$R$^3$Z$^-$; CF$_3$—O—(CH$_2$)$_{24}$—P$^+$R$^1$R$^2$R$^3$Z$^-$; or CF$_3$—O—(CH$_2$)$_{24}$—O-glucoside.

38. A compound according to claim 2, wherein said compound is:

SF$_5$—(CH$_2$)$_4$—N$^+$R$^1$R$^2$R$^3$Z$^-$; SF$_5$—(CH$_2$)$_4$—P$^+$R$^1$R$^2$R$^3$Z$^-$; SF$_5$—(CH$_2$)$_5$—N$^+$R$^1$R$^2$R$^3$Z$^-$; SF$_5$—(CH$_2$)$_5$—P$^+$R$^1$R$^2$R$^3$Z$^-$; SF$_5$—(CH$_2$)$_6$—N$^+$R$^1$R$^2$R$^3$Z$^-$; SF$_5$—(CH$_2$)$_6$—P$^+$R$^1$R$^2$R$^3$Z$^-$; SF$_5$—(CH$_2$)$_7$—N$^+$R$^1$R$^2$R$^3$Z$^-$; SF$_5$—(CH$_2$)$_7$—P$^+$R$^1$R$^2$R$^3$Z$^-$; SF$_5$—(CH$_2$)$_8$—N$^+$R$^1$R$^2$R$^3$Z$^-$; SF$_5$—(CH$_2$)$_8$—P$^+$R$^1$R$^2$R$^3$Z$^-$; SF$_5$—(CH$_2$)$_9$—N$^+$R$^1$R$^2$R$^3$Z$^-$; SF$_5$—(CH$_2$)$_9$—P$^+$R$^1$R$^2$R$^3$Z$^-$; SF$_5$—(CH$_2$)$_{10}$—N$^+$R$^1$R$^2$R$^3$Z$^-$; SF$_5$—(CH$_2$)—P$^+$R$^1$R$^2$R$^3$Z$^-$; SF$_5$—(CH$_2$)$_{11}$—N$^+$R$^1$R$^2$R$^3$Z$^-$; SF$_5$—(CH$_2$)$_{11}$—P$^+$R$^1$R$^2$R$^3$Z$^-$; SF$_5$—(CH$_2$)$_{12}$—N$^+$R$^1$R$^2$R$^3$Z$^-$; SF$_5$—(CH$_2$)$_{12}$—P$^+$R$^1$R$^2$R$^3$Z$^-$; SF$_5$—(CH$_2$)$_{13}$—N$^+$R$^1$R$^2$R$^3$Z$^-$; SF$_5$—(CH$_2$)$_{13}$—P$^+$R$^1$R$^2$R$^3$Z$^-$; SF$_5$—(CH$_2$)$_{14}$N$^+$R$^1$R$^2$R$^3$Z$^-$; SF$_5$—(CH$_2$)$_{14}$—P$^+$R$^1$R$^2$R$^3$Z$^-$; SF$_5$—(CH$_2$)$_{15}$—N$^+$R$^1$R$^2$R$^3$Z$^-$; SF$_5$—(CH$_2$)$_{15}$—P$^+$R$^1$R$^2$R$^3$Z$^-$; SF$_5$—(CH$_2$)$_{16}$—N$^+$R$^1$R$^2$R$^3$Z$^-$;SF$_5$—(CH$_2$)$_{16}$—P$^+$R$^1$R$^2$R$^3$Z$^-$; SF$_5$—(CH$_2$)$_{17}$—N$^+$R$^1$R$^2$R$^3$Z$^-$; SF$_5$—(CH$_2$)$_{17}$—P$^+$R$^1$R$^2$R$^3$Z$^-$; SF$_5$—(CH$_2$)$_{18}$—N$^+$R$^1$R$^2$R$^3$Z$^-$; SF$_5$—(CH$_2$)$_{18}$—P$^+$R$^1$R$^2$R$^3$Z$^-$; SF$_5$—(CH$_2$)$_{19}$—P$^+$R$^1$R$^2$R$^3$Z$^-$; SF$_5$—(CH$_2$)$_{20}$—N$^+$R$^1$R$^2$R$^3$Z$^-$; SF$_5$—(CH$_2$)$_{20}$—P$^+$R$^1$R$^2$R$^3$Z$^-$; SF$_5$—(CH$_2$)$_{21}$—N$^+$R$^1$R$^2$R$^3$Z$^-$; SF$_5$—(CH$_2$)$_{21}$—P$^+$R$^1$R$^2$R$^3$Z$^-$; SF$_5$—(CH$_2$)$_{22}$—N$^+$R$^1$R$^2$R$^3$Z$^-$; SF$_5$—(CH$_2$)$_{22}$—P$^+$R$^1$R$^2$R$^3$Z$^-$; SF—(CH$_2$)$_{23}$—N$^+$R$^1$R$^2$R$^3$Z$^-$; SF$_5$—(CH$_2$)$_{23}$—P$^+$R$^1$R$^2$R$^3$Z$^-$; SF$_5$—(CH$_2$)$_{24}$—N$^+$R$^1$R$^2$R$^3$Z$^-$; SF$_5$—(CH$_2$)$_{24}$—P$^+$R$^1$R$^2$R$^3$Z$^-$; SF$_5$—CH=CH—(CH$_2$)$_4$—N$^+$R$^1$R$^2$R$^3$Z$^-$; SF$_5$—CH=CH—

$(CH_2)_4—P^+R^1R^2R^3Z^-$; $SF_5—CH=CH—(CH_2)_5—N^+R^1R^2R^3Z^-$; $SF_5—CH=CH—(CH_2)_5—P^+R^1R^2R^3Z^-$; $SF_5—CH=CH—(CH_2)_6—N^+R^1R^2R^3Z^-$; $SF_5—CH=CH—(CH_2)_6—P^+R^1R^2R^3Z^-$; $SF_5—CH=CH—(CH_2)_7—N^+R^1R^2R^3Z^-$; $SF_5—CH=CH—(CH_2)_7—P^+R^1R^2R^3Z^-$; $SF_5—CH=CH—(CH_2)_8—N^+R^1R^2R^3Z^-$; $SF_5—CH=CH—(CH_2)_8—P^+R^1R^2R^3Z^-$; $SF_5—CH=CH—(CH_2)_9—N^+R^1R^2R^3Z^-$; $SF_5—CH=CH—(CH_2)_9—P^+R^1R^2R^3Z^-$; $SF_5—CH=CH—(CH_2)_{10}—N^+R^1R^2R^3Z^-$; $SF_5—CH=CH—(CH_2)_{10}—P^+R^1R^2R^3Z^-$; $SF_5—CH=CH—(CH_2)_{11}—N^+R^1R^2R^3Z^-$; $SF_5—CH=CH—(CH_2)_{11}—P^+R^1R^2R^3Z^-$; $SF_5—CH=CH—(CH_2)_{12}—N^+R^1R^2R^3Z^-$; $SF_5—CH=CH—(CH_2)_{12}—P^+R^1R^2R^3Z^-$; $SF_5—CH=CH—(CH_2)_{13}—N^+R^1R^2R^3Z^-$; $SF_5—CH=CH—(CH_2)_{13}—P^+R^1R^2R^3Z^-$; $SF_5—CH=CH—(CH_2)_{14}—N^+R^1R^2R^3Z^-$; $SF_5—CH=CH—(CH_2)_{14}—P^+R^1R^2R^3Z^-$; $SF_5—CH=CH—(CH_2)_{15}—N^+R^1R^2R^3Z^-$; $SF_5—CH=CH—(CH_2)_{15}—P^+R^1R^2R^3Z^-$; $SF_5—CH=CH—(CH_2)_{16}—N^+R^1R^2R^3Z^-$; $SF_5—CH=CH—(CH_2)_{16}—P^+R^1R^2R^3Z^-$; $SF_5—CH=CH—(CH_2)_{17}—N^+R^1R^2R^3Z^-$; $SF_5—CH=CH—(CH_2)_{17}—P^+R^1R^2R^3Z^-$; $SF_5—CH=CH—(CH_2)_{18}—N^+R^1R^2R^3Z^-$; $SF_5—CH=CH—(CH_2)_{18}—P^+R^1R^2R^3Z^-$; $SF_5—CH=CH—(CH_2)_{19}—N^+R^1R^2R^3Z^-$; $SF_5—CH=CH—(CH_2)_{19}—P^+R^1R^2R^3Z^-$; $SF_5—CH=CH—(CH_2)_{20}—N^+R^1R^2R^3Z^-$; $SF_5—CH=CH—(CH_2)_{20}—P^+R^1R^2R^3Z^-$; $SF_5—CH=CH—(CH_2)_{21}—N^+R^1R^2R^3Z^-$; $SF_5—CH=CH—(CH_2)_{21}—P^+R^1R^2R^3Z^-$; $SF_5—CH=CH—(CH_2)_{22}—N^+R^1R^2R^3Z^-$; $SF_5—CH=CH—(CH_2)_{22}—P^+R^1R^2R^3Z^-$; $SF_5—CH=CH—(CH_2)_{23}—N^+R^1R^2R^3Z^-$; $SF_5—CH=CH—(CH_2)_{23}—P^+R^1R^2R^3Z^-$; $SF_5—CH=CH—(CH_2)_{24}—N^+R^1R^2R^3Z^-$; $SF_5—CH=CH—(CH_2)_{24}—P^+R^1R^2R^3Z^-$; $SF_5—CH_2CHBr—(CH_2)_4—N^+R^1R^2R^3Z^-$; $SF_5—CH_2CHBr—(CH_2)_4—P^+R^1R^2R^3Z^-$; $SF_5—CH_2CHBr—(CH_2)_5—N^+R^1R^2R^3Z^-$; $SF_5—CH_2CHBr—(CH_2)_5—P^+R^1R^2R^3Z^-$; $SF_5—CH_2CHBr—(CH_2)_6—N^+R^1R^2R^3Z^-$; $SF_5—CH_2CHBr—(CH_2)_6—P^+R^1R^2R^3Z^-$; $SF_5—CH_2CHBr—(CH_2)_7—N^+R^1R^2R^3Z^-$; $SF_5—CH_2CHBr—(CH_2)_7—P^+R^1R^2R^3Z^-$; $SF_5—CH_2CHBr—(CH_2)_8—N^+R^1R^2R^3Z^-$; $SF_5—CH_2CHBr—(CH_2)_8—P^+R^1R^2R^3Z^-$; $SF_5—CH_2CHBr—(CH_2)_9—N^+R^1R^2R^3Z^-$; $SF_5—CH_2CHBr—(CH_2)_9—P^+R^1R^2R^3Z^-$; $SF_5—CH_2CHBr—(CH_2)_{10}—N^+R^1R^2R^3Z^-$; $SF_5—CH_2CHBr—(CH_2)_{10}—P^+R^1R^2R^3Z^-$; $SF_5—CH_2CHBr—(CH_2)_{11}—N^+R^1R^2R^3Z^-$; $SF_5—CH_2CHBr—(CH_2)_{11}—P^+R^1R^2R^3Z^-$; $SF_5—CH_2CHBr—(CH_2)_{12}—N^+R^1R^2R^3Z^-$; $SF_5—CH_2CHBr—(CH_2)_{12}—P^+R^1R^2R^3Z^-$; $SF_5—CH_2CHBr—(CH_2)_{13}—N^+R^1R^2R^3Z^-$; $SF_5—CH_2CHBr—(CH_2)_{13}—P^+R^1R^2R^3Z^-$; $SF_5—CH_2CHBr—(CH_2)_{14}—N^+R^1R^2R^3Z^-$; $SF_5—CH_2CHBr—(CH_2)_{14}—P^+R^1R^2R^3Z^-$; $SF_5—CH_2CHBr—(CH_2)_{15}—N^+R^1R^2R^3Z^-$; $SF_5—CH_2CHBr—(CH_2)_{15}—P^+R^1R^2R^3Z^-$; $SF_5—CH_2CHBr—(CH_2)_{16}—N^+R^1R^2R^3Z$ $SF_5—CH_2CHBr—(CH_2)_{17}—N^+R^1R^2R^3Z^-$; $SF_5—CH_2CHBr—(CH_2)_{17}—P^+R^1R^2R^3Z^-$; $SF_5—CH_2CHBr—(CH_2)_{18}—N^+R^1R^2R^3Z^-$; $SF_5—CH_2CHBr—(CH_2)_{18}—P^+R^1R^2R^3Z^-$; $SF_5—CH_2CHBr—(CH_2)_{19}—N^+R^1R^2R^3Z^-$; $SF_5—CH_2CHBr—(CH_2)_{19}—P^+R^1R^2R^3Z^-$; $SF_5—CH_2CHBr—(CH_2)_{20}—N^+R^1R^2R^3Z^-$; $SF_5—CH_2CHBr—(CH_2)_{20}—P^+R^1R^2R^3Z^-$; $SF_5—CH_2CHBr—(CH_2)_{21}—N^+R^1R^2R^3Z^-$; $SF_5—CH_2CHBr—(CH_2)_{21}—P^+R^1R^2R^3Z^-$; $SF_5—CH_2CHBr—(CH_2)_{22}—N^+R^1R^2R^3Z^-$; $SF_5—CH_2CHBr—(CH_2)_{22}—P^+R^1R^2R^3Z^-$; $SF_5—CH_2CHBr—(CH_2)_{23}—N^+R^1R^2R^3Z^-$; $SF_5CH_2CHBr—(CH_2)_{23}—P^+R^1R^2R^3Z^-$; $SF_5—CH_2CHBr—(CH_2)_{24}—N^+R^1R^2R^3Z^-$; or $SF_5—CH_2CHBr—(CH_2)_{24}—P^+R^1R^2R^3Z^-$.

39. A compound according to claim 21, wherein said compound is:

$SF_5—(CH_2)_8$—O-glucoside; $SF_5—(CH_2)_9$—O-glucoside; $SF_5—(CH_2)_{10}$—O-glucoside; $SF_5—(CH_2)_{11}$—O-glucoside; $SF_5—(CH_2)_{12}$—O-glucoside; $SF_5—(CH_2)_{13}$—O-glucoside; $SF_5—(CH_2)_{14}$—O-glucoside; $SF_5—(CH_2)_{15}$—O-glucoside; $SF_5—(CH_2)_{16}$—O-glucoside; $SF_5—(CH_2)_{17}$—O-glucoside; $SF_5—(CH_2)_{18}$—O-glucoside; $SF_5—(CH_2)_{19}$—O-glucoside; $SF_5—(CH_2)_{20}$—O-glucoside; $SF_5—(CH_2)_{21}$—O-glucoside; $SF_5—(CH_2)_{22}$—O-glucoside; $SF_5—(CH_2)_{23}$—O-glucoside; $SF_5—(CH_2)_{24}$—O-glucoside; $SF_5—CH=CH—(CH_2)_8$—O-glucoside; $SF_5—CH=CH—(CH_2)_9$—O-glucoside; $SF_5—CH=CH—(CH_2)_{10}$—O-glucoside; $SF_5—CH=CH—(CH_2)_{11}$—O-glucoside; $SF_5—CH=CH—(CH_2)_{12}$—O-glucoside; $SF_5—CH=CH—(CH_2)_{13}$—O-glucoside; $SF_5—CH=CH—(CH_2)_{14}$—O-glucoside; $SF_5—CH=CH—(CH_2)_{15}$—O-glucoside; $SF_5—CH=CH—(CH_2)_{16}$—O-glucoside; $SF_5—CH=CH—(CH_2)_{17}$—O-glucoside; $SF_5—CH=CH—(CH_2)_{18}$—O-glucoside; $SF_5—CH=CH—(CH_2)_{19}$—O-glucoside; $SF_5—CH=CH—(CH_2)_{20}$—O-glucoside; $SF_5—CH=CH—(CH_2)_{21}$—O-glucoside; $SF_5—CH=CH—(CH_2)_{22}$—O-glucoside; $SF_5—CH=CH—(CH_2)_{23}$—O-glucoside; $SF_5—CH=CH—(CH_2)_{24}$—O-glucoside; $SF_5—CH_2CHBr—(CH_2)_8$—O—glucoside; $SF_5—CH_2CHBr—(CH_2)_9$—O-glucoside; $SF_5—CH_2CHBr—(CH_2)_{10}$—O-glucoside; $SF_5—CH_2CHBr—(CH_2)_{11}$—O-glucoside; $SF_5—CH_2CHBr—(CH_2)_{12}$—O-glucoside; $SF_5—CH_2CHBr—(CH_2)_{13}$—O-glucoside; $SF_5—CH_2CHBr—(CH_2)_{14}$—O-glucoside; $SF_5—CH_2CHBr—(CH_2)_{15}$—O-glucoside; $SF_5—CH_2CHBr—(CH_2)_{16}$—O-glucoside; $SF_5—CH_2CHBr—(CH_2)_{17}$—O-glucoside; $SF_5—CH_2CHBr—(CH_2)_{18}$—O-glucoside; $SF_5—CH_2CHBr—(CH_2)_{19}$—O-glucoside; $SF_5—CH_2CHBr—(CH_2)_{20}$—O-glucoside; $SF_5—CH_2CHBr—(CH_2)_{21}$—O-glucoside; $SF_5—CH_2CHBr—(CH_2)_{22}$—O-glucoside; $SF_5—CH_2CHBr—(CH_2)_{23}$—O-glucoside; or $SF_5—CH_2CHBr—(CH_2)_{24}$—O-glucoside.

40. A compound of formula IIa, IIb or IIc $$CF_3O—(CH_2)_n—X \qquad \text{IIa}$$

$$CF_3O—CH_2—CH(Hal)-(CH_2)_{(n-1)}—X \qquad \text{IIb}$$

$$CF_3O—CH=CH—(CH_2)_{(n-1)}—X \qquad \text{IIc}$$

in which n is an integer from the range 1 to 30, (Hal) is F, Cl, Br or I,

X is (a) —COOM, —SO$_3$M, —OSO$_3$M, —PO$_3$M$_2$, —OPO$_3$M$_2$, —(OCH$_2$CH$_2$)$_m$—O—(CH$_2$)$_o$—COOM, —(OCH$_2$CH$_2$)$_m$—O—(CH$_2$)$_o$—SO$_3$M, —(OCH$_2$CH$_2$)$_m$—O—(CH$_2$)$_o$—OSO$_3$M, —(OCH$_2$CH$_2$)$_m$—O—(CH$_2$)$_o$—PO$_3$M$_2$, or —(OCH$_2$CH$_2$)$_m$—O—(CH$_2$)$_o$—OPO$_3$M$_2$,

M is H, an alkali metal ion, or $NH_4^+$,
m is an integer from the range 1 to 1000, and
o is an integer selected from 1, 2, 3 or 4,
wherein X is not —COOH;
(b) $—NR^1R^2R^{3+}Z^-$, $—PR^1R^2R^{3+}Z^-$,

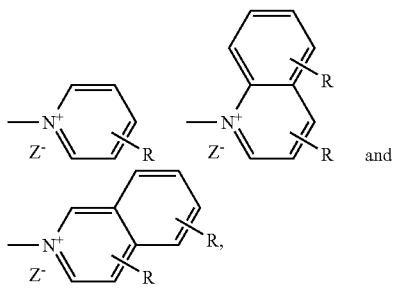

and

R is H or $C_{1-4}$-alkyl in any desired position,
$Z^-$ is $Cl^-$, $Br^-$, $I^-$, $CH_3SO_3^-$, $CF_3SO_3^-$, $CH_3PhSO_3^-$, or $PhSO_3^-$,
$R^1$, $R^2$ and $R^3$ are each, independently of one another, H, $C_{1-30}$-alkyl, Ar, or —$CH_2Ar$, and
Ar is an unsubstituted or mono- or polysubstituted aromatic ring or fused ring system having 6 to 18 C atoms, in which, in addition, one or two CH groups are each optionally replaced by N;
(c) —Cl, —Br, —I, —$(OCH_2CH_2)_m$—OH, —O-(glycoside)$_o$, —$(OCH_2CH_2)_m$—$OCH_2$—CHOH—$CH_2$—OH, —$(OCH_2CH_2)_m$—$OCH_2Ar(—NCO)_p$, —$(OCH_2CH_2)_m$—$OAr(—NCO)_p$, —$SiR^1R^2Z$, —$SiR^1Z_2$, —$SiZ_3$, —COZ, —$(OCH_2CH_2)_m$—$SO_2CH=CH_2$, —$SO_2Z$, or

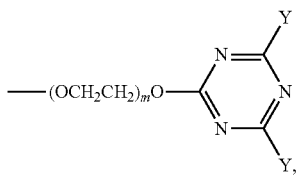

m is an integer from the range 0 to 1000,
o is an integer from the range 1 to 10,
p is 1 or 2,
$R^1$ and $R^2$ are each, independently of one another, $C_{1-30}$-alkyl, Ar, or —$CH_2Ar$,
Ar is an unsubstituted or mono- or polysubstituted aromatic ring or fused ring system having 6 to 18 C atoms, in which, in addition, one or two CH groups are each optionally replaced by N,
glycoside is an etherified carbohydrate,
all Z are each, independently of one another, —H, —Cl, —F, —$NR^1R^2$, —$OR^1$, or —N-imidazolyl, and
Y is Cl or F; or
(d) —$(OCH_2CH_2)_m OCOCR=CH_2$, —$(OCH_2CH_2)_m$—$OCR=CH_2$,

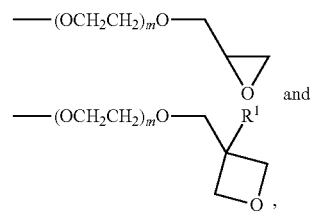

m is an integer from the range 0 to 1000, and
R and $R^1$ are each H or $C_{1-4}$-alkyl;
or a corresponding salt of a compound of the formula IIa, IIb or IIc.

41. A compound of formula IIb or IIc $CF_3O—CH_2—CH(Hal)-(CH_2)_{(n-1)}—X$      IIb $CF_3O—CH=CH—(CH_2)_{(n-1)}—X$      IIc in which
n is an integer from the range 1 to 30,
X is a cationic, nonionic, amphoteric or anionic polar group or a polymerizable group, and
(Hal) is F, Cl, Br or I,
or a corresponding salt of a compound of the formula IIb or IIc.

42. A process for the preparation of a compound according to claim 13, said process comprising:
preparing a compound of formula V $F_3CO—(CH_2)_n—OH$      V by conversion of a protected diol into the protected monotrifluoromethoxyalcohol followed by deprotection,
and then converting the compound of formula V into said compound of formula IIa by modification of the OH group.

43. A process for the preparation of a compound according to claim 2, said process comprising:
preparing a compound of the formula $F_5S—CH_2—CH(Hal)-(CH_2)_{(n-1)}—X$ in which X is OH, and,
if a compound of formula IIIa or IIIc is to be prepared, reacted by elimination of hydrogen halide and,
if a compound of formula IIIa is to be prepared, subsequent hydrogenation, and
subsequently the product is converted into the compound of formula IIIa, IIIb or IIIc by modification of the OH group.

* * * * *

UNITED STATES PATENT AND TRADEMARK OFFICE
CERTIFICATE OF CORRECTION

PATENT NO. : 8,008,358 B2
APPLICATION NO. : 11/813314
DATED : August 30, 2011
INVENTOR(S) : Kirsch et al.

It is certified that error appears in the above-identified patent and that said Letters Patent is hereby corrected as shown below:

Column 42, Line 47 reads: "$SO_3H$; $SF_5$-$CH_2CHBr$-$(CHA_{212})$-$COOH$; $SF_5$" should read
-- $SO_3H$; $SF$-$CH_2CHRr$-$(CH_2)_{12}$-$COOH$; $SF_5$ --.

Column 43, Line 14 reads: "$(CH_2)_8$-$H$; $CF_3$-$O$-$(CH_2)_9$-$OH$; $CF_3$-$O$-" should read
-- $(CH_2)_8$-$OH$; $CF_3$-$O$-$(CH_2)_9$-$OH$; $CF_3$-$O$- --.

Column 44, Line 23 through Column 47, Line 59 – Delete All and replace with:

36. A compound according to claim 2, wherein said compound is:
$SF_5$-$(CH_2)_4$-$(OCH_2CH_2)_m$-$OCOCH=CH_2$; $SF_5$-$(CH_2)_4$-$(OCH_2CH_2)_m$-$OCH=CH_2$; $SF_5$-$(CH_2)_4$-$(OCH_2CH_2)_m$-$OAr(NCO)_p$; $SF_5$-$(CH_2)_5$-$(OCH_2CH_2)_m$-$OCOCH=CH_2$; $SF_5$-$(CH_2)_5$-$(OCH_2CH_2)_m$-$OCH=CH_2$; $SF_5$-$(CH_2)_5$-$(OCH_2CH_2)_m$-$OAr(NCO)_p$; $SF_5$-$(CH_2)_6$-$(OCH_2CH_2)_m$-$OCOCH=CH_2$; $SF_5$-$(CH_2)_6$-$(OCH_2CH_2)_m$-$OCH=CH_2$; $SF_5$-$(CH_2)_6$-$(OCH_2CH_2)_m$-$OAr(NCO)_p$; $SF_5$-$(CH_2)_7$-$(OCH_2CH_2)_m$-$OCOCH=CH_2$; $SF_5$-$(CH_2)_7$-$(OCH_2CH_2)_m$-$OCH=CH_2$; $SF_5$-$(CH_2)_7$-$(OCH_2CH_2)_m$-$OAr(NCO)_p$; $SF_5$-$(CH_2)_8$-$(OCH_2CH_2)_m$-$OCOCH=CH_2$; $SF_5$-$(CH_2)_8$-$(OCH_2CH_2)_m$-$OCH=CH_2$; $SF_5$-$(CH_2)_8$-$(OCH_2CH_2)_m$-$OAr(NCO)_p$; $SF_5$-$(CH_2)_9$-$(OCH_2CH_2)_m$-$OCOCH=CH_2$; $SF_5$-$(CH_2)_9$-$(OCH_2CH_2)_m$-$OCH=CH_2$; $SF_5$-$(CH_2)_9$-$(OCH_2CH_2)_m$-$OAr(NCO)_p$; $SF_5$-$(CH_2)_{10}$-$(OCH_2CH_2)_m$-$OCOCH=CH_2$; $SF_5$-$(CH_2)_{10}$-$(OCH_2CH_2)_m$-$OCH=CH_2$; $SF_5$-$(CH_2)_{10}$-$(OCH_2CH_2)_m$-$OAr(NCO)_p$; $SF_5$-$(CH_2)_{11}$-$(OCH_2CH_2)_m$-$OCOCH=CH_2$; $SF_5$-$(CH_2)_{11}$-$(OCH_2CH_2)_m$-$OCH=CH_2$; $SF_5$-$(CH_2)_{11}$-$(OCH_2CH_2)_m$-$OAr(NCO)_p$; $SF_5$-$(CH_2)_{12}$-$(OCH_2CH_2)_m$-$OCOCH=CH_2$; $SF_5$-$(CH_2)_{12}$-$(OCH_2CH_2)_m$-$OCH=CH_2$; $SF_5$-$(CH_2)_{12}$-$(OCH_2CH_2)_m$-$OAr(NCO)_p$; $SF_5$-$(CH_2)_{13}$-$(OCH_2CH_2)_m$-$OCOCH=CH_2$; $SF_5$-$(CH_2)_{13}$-$(OCH_2CH_2)_m$-$OCH=CH_2$; $SF_5$-$(CH_2)_{13}$-$(OCH_2CH_2)_m$-$OAr(NCO)_p$; $SF_5$-$(CH_2)_{14}$-$(OCH_2CH_2)_m$-$OCOCH=CH_2$; $SF_5$-$(CH_2)_{14}$-$(OCH_2CH_2)_m$-$OCH=CH_2$; $SF_5$-$(CH_2)_{14}$-$(OCH_2CH_2)_m$-$OAr(NCO)_p$; $SF_5$-$(CH_2)_{15}$-$(OCH_2CH_2)_m$-$OCOCH=CH_2$; $SF_5$-$(CH_2)_{15}$-$(OCH_2CH_2)_m$-$OCH=CH_2$; $SF_5$-$(CH_2)_{15}$-$(OCH_2CH_2)_m$-$OAr(NCO)_p$; $SF_5$-$(CH_2)_{16}$-$(OCH_2CH_2)_m$-$OCOCH=CH_2$;

Signed and Sealed this
Seventh Day of August, 2012

David J. Kappos
*Director of the United States Patent and Trademark Office*

$SF_5$-$(CH_2)_{16}$-$(OCH_2CH_2)_m$-OCH=$CH_2$; $SF_5$-$(CH_2)_{16}$-$(OCH_2CH_2)_m$-OAr(NCO)$_p$; $SF_5$-$(CH_2)_{17}$-$(OCH_2CH_2)_m$-OCOCH=$CH_2$; $SF_5$-$(CH_2)_{17}$-$(OCH_2CH_2)_m$-OCH=$CH_2$; $SF_5$-$(CH_2)_{17}$-$(OCH_2CH_2)_m$-OAr(NCO)$_p$; $SF_5$-$(CH_2)_{18}$-$(OCH_2CH_2)_m$-OCOCH=$CH_2$; $SF_5$-$(CH_2)_{18}$-$(OCH_2CH_2)_m$-OCH=$CH_2$; $SF_5$-$(CH_2)_{18}$-$(OCH_2CH_2)_m$-OAr(NCO)$_p$; $SF_5$-$(CH_2)_{19}$-$(OCH_2CH_2)_m$-OCOCH=$CH_2$; $SF_5$-$(CH_2)_{19}$-$(OCH_2CH_2)_m$-OCH=$CH_2$; $SF_5$-$(CH_2)_{19}$-$(OCH_2CH_2)_m$-OAr(NCO)$_p$; $SF_5$-$(CH_2)_{20}$-$(OCH_2CH_2)_m$-OCOCH=$CH_2$; $SF_5$-$(CH_2)_{20}$-$(OCH_2CH_2)_m$-OCH=$CH_2$; $SF_5$-$(CH_2)_{20}$-$(OCH_2CH_2)_m$-OAr(NCO)$_p$; $SF_5$-$(CH_2)_{21}$-$(OCH_2CH_2)_m$-OCOCH=$CH_2$; $SF_5$-$(CH_2)_{21}$-$(OCH_2CH_2)_m$-OCH=$CH_2$; $SF_5$-$(CH_2)_{21}$-$(OCH_2CH_2)_m$-OAr(NCO)$_p$; $SF_5$-$(CH_2)_{22}$-$(OCH_2CH_2)_m$-OCOCH=$CH_2$; $SF_5$-$(CH_2)_{22}$-$(OCH_2CH_2)_m$-OCH=$CH_2$; $SF_5$-$(CH_2)_{22}$-$(OCH_2CH_2)_m$-OAr(NCO)$_p$; $SF_5$-$(CH_2)_{23}$-$(OCH_2CH_2)_m$-OCOCH=$CH_2$; $SF_5$-$(CH_2)_{23}$-$(OCH_2CH_2)_m$-OCH=$CH_2$; $SF_5$-$(CH_2)_{23}$-$(OCH_2CH_2)_m$-OAr(NCO)$_p$; $SF_5$-$(CH_2)_{24}$-$(OCH_2CH_2)_m$-OCOCH=$CH_2$; $SF_5$-$(CH_2)_{24}$-$(OCH_2CH_2)_m$-OCH=$CH_2$; $SF_5$-$(CH_2)_{24}$-$(OCH_2CH_2)_m$-OAr(NCO)$_p$; $SF_5$-CH=CH-$(CH_2)_4$-$(OCH_2CH_2)_m$-OCOCH=$CH_2$; $SF_5$-CH=CH-$(CH_2)_4$-$(OCH_2CH_2)_m$-OCH=$CH_2$; $SF_5$-CH=CH-$(CH_2)_4$-$(OCH_2CH_2)_m$-OAr(NCO)$_p$; $SF_5$-CH=CH-$(CH_2)_5$-$(OCH_2CH_2)_m$-OCOCH=$CH_2$; $SF_5$-CH=CH-$(CH_2)_5$-$(OCH_2CH_2)_m$-OCH=$CH_2$; $SF_5$-CH=CH-$(CH_2)_5$-$(OCH_2CH_2)_m$-OAr(NCO)$_p$; $SF_5$-CH=CH-$(CH_2)_6$-$(OCH_2CH_2)_m$-OCOCH=$CH_2$; $SF_5$-CH=CH-$(CH_2)_6$-$(OCH_2CH_2)_m$-OCH=$CH_2$; $SF_5$-CH=CH-$(CH_2)_6$-$(OCH_2CH_2)_m$-OAr(NCO)$_p$; $SF_5$-CH=CH-$(CH_2)_7$-$(OCH_2CH_2)_m$-OCOCH=$CH_2$; $SF_5$-CH=CH-$(CH_2)_7$-$(OCH_2CH_2)_m$-OCH=$CH_2$; $SF_5$-CH=CH-$(CH_2)_7$-$(OCH_2CH_2)_m$-OAr(NCO)$_p$; $SF_5$-CH=CH-$(CH_2)_8$-$(OCH_2CH_2)_m$-OCOCH=$CH_2$; $SF_5$-CH=CH-$(CH_2)_8$-$(OCH_2CH_2)_m$-OCH=$CH_2$; $SF_5$-CH=CH-$(CH_2)_8$-$(OCH_2CH_2)_m$-OAr(NCO)$_p$; $SF_5$-CH=CH-$(CH_2)_9$-$(OCH_2CH_2)_m$-OCOCH=$CH_2$; $SF_5$-CH=CH-$(CH_2)_9$-$(OCH_2CH_2)_m$-OCH=$CH_2$; $SF_5$-CH=CH-$(CH_2)_9$-$(OCH_2CH_2)_m$-OAr(NCO)$_p$; $SF_5$-CH=CH-$(CH_2)_{10}$-$(OCH_2CH_2)_m$-OCOCH=$CH_2$; $SF_5$-CH=CH-$(CH_2)_{10}$-$(OCH_2CH_2)_m$-OCH=$CH_2$; $SF_5$-CH=CH-$(CH_2)_{10}$-$(OCH_2CH_2)_m$-OAr(NCO)$_p$; $SF_5$-CH=CH-$(CH_2)_{11}$-$(OCH_2CH_2)_m$-OCOCH=$CH_2$; $SF_5$-CH=CH-$(CH_2)_{11}$-$(OCH_2CH_2)_m$-OCH=$CH_2$; $SF_5$-CH=CH-$(CH_2)_{11}$-$(OCH_2CH_2)_m$-OAr(NCO)$_p$; $SF_5$-CH=CH-$(CH_2)_{12}$-$(OCH_2CH_2)_m$-OCOCH=$CH_2$; $SF_5$-CH=CH-$(CH_2)_{12}$-$(OCH_2CH_2)_m$-OCH=$CH_2$; $SF_5$-CH=CH-$(CH_2)_{12}$-$(OCH_2CH_2)_m$-OAr(NCO)$_p$; $SF_5$-CH=CH-$(CH_2)_{13}$-$(OCH_2CH_2)_m$-OCOCH=$CH_2$; $SF_5$-CH=CH-$(CH_2)_{13}$-$(OCH_2CH_2)_m$-OCH=$CH_2$; $SF_5$-CH=CH-$(CH_2)_{13}$-$(OCH_2CH_2)_m$-OAr(NCO)$_p$; $SF_5$-CH=CH-$(CH_2)_{14}$-$(OCH_2CH_2)_m$-OCOCH=$CH_2$; $SF_5$-CH=CH-$(CH_2)_{14}$-$(OCH_2CH_2)_m$-OCH=$CH_2$; $SF_5$-CH=CH-$(CH_2)_{14}$-$(OCH_2CH_2)_m$-OAr(NCO)$_p$; $SF_5$-CH=CH-$(CH_2)_{15}$-$(OCH_2CH_2)_m$-OCOCH=$CH_2$; $SF_5$-CH=CH-$(CH_2)_{15}$-$(OCH_2CH_2)_m$-OCH=$CH_2$; $SF_5$-CH=CH-$(CH_2)_{15}$-$(OCH_2CH_2)_m$-OAr(NCO)$_p$; $SF_5$-CH=CH-$(CH_2)_{16}$-$(OCH_2CH_2)_m$-OCOCH=$CH_2$; $SF_5$-CH=CH-$(CH_2)_{16}$-$(OCH_2CH_2)_m$-OCH=$CH_2$; $SF_5$-CH=CH-$(CH_2)_{16}$-$(OCH_2CH_2)_m$-OAr(NCO)$_p$; $SF_5$-CH=CH-$(CH_2)_{17}$-$(OCH_2CH_2)_m$-OCOCH=$CH_2$; $SF_5$-CH=CH-$(CH_2)_{17}$-$(OCH_2CH_2)_m$-OCH=$CH_2$; $SF_5$-CH=CH-$(CH_2)_{17}$-$(OCH_2CH_2)_m$-OAr(NCO)$_p$; $SF_5$-CH=CH-$(CH_2)_{18}$-$(OCH_2CH_2)_m$-OCOCH=$CH_2$; $SF_5$-CH=CH-$(CH_2)_{18}$-$(OCH_2CH_2)_m$-OCH=$CH_2$; $SF_5$-CH=CH-$(CH_2)_{18}$-$(OCH_2CH_2)_m$-OAr(NCO)$_p$; $SF_5$-CH=CH-$(CH_2)_{19}$-$(OCH_2CH_2)_m$-OCOCH=$CH_2$; $SF_5$-CH=CH-$(CH_2)_{19}$-$(OCH_2CH_2)_m$-OCH=$CH_2$; $SF_5$-CH=CH-$(CH_2)_{19}$-$(OCH_2CH_2)_m$-OAr(NCO)$_p$; $SF_5$-CH=CH-$(CH_2)_{20}$-$(OCH_2CH_2)_m$-OCOCH=$CH_2$; $SF_5$-CH=CH-$(CH_2)_{20}$-$(OCH_2CH_2)_m$-OCH=$CH_2$; $SF_5$-CH=CH-$(CH_2)_{20}$-$(OCH_2CH_2)_m$-OAr(NCO)$_p$; $SF_5$-CH=CH-$(CH_2)_{21}$-$(OCH_2CH_2)_m$-OCOCH=$CH_2$; $SF_5$-CH=CH-$(CH_2)_{21}$-$(OCH_2CH_2)_m$-OCH=$CH_2$; $SF_5$-CH=CH-$(CH_2)_{21}$-$(OCH_2CH_2)_m$-OAr(NCO)$_p$; $SF_5$-CH=CH-$(CH_2)_{22}$-$(OCH_2CH_2)_m$-OCOCH=$CH_2$; $SF_5$-CH=CH-$(CH_2)_{22}$-$(OCH_2CH_2)_m$-OCH=$CH_2$; $SF_5$-CH=CH-$(CH_2)_{22}$-$(OCH_2CH_2)_m$-OAr(NCO)$_p$; $SF_5$-CH=CH-$(CH_2)_{23}$-$(OCH_2CH_2)_m$-OCOCH=$CH_2$; $SF_5$-CH=CH-$(CH_2)_{23}$-$(OCH_2CH_2)_m$-OCH=$CH_2$; $SF_5$-CH=CH-$(CH_2)_{23}$-$(OCH_2CH_2)_m$-OAr(NCO)$_p$; $SF_5$-CH=CH-$(CH_2)_{24}$-$(OCH_2CH_2)_m$-OCOCH=$CH_2$; $SF_5$-CH=CH-$(CH_2)_{24}$-$(OCH_2CH_2)_m$-OCH=$CH_2$; $SF_5$-CH=CH-$(CH_2)_{24}$-$(OCH_2CH_2)_m$-OAr(NCO)$_p$; $SF_5$-$CH_2$CHBr-$(CH_2)_4$-$(OCH_2CH_2)_m$-OCOCH=$CH_2$; $SF_5$-$CH_2$CHBr-$(CH_2)_4$-

$(OCH_2CH_2)_m$-OCH=CH$_2$; SF$_5$-CH$_2$CHBr-(CH$_2$)$_4$-$(OCH_2CH_2)_m$-OAr(NCO)$_p$; SF$_5$-CH$_2$CHBr-(CH$_2$)$_5$-$(OCH_2CH_2)_m$-OCOCH=CH$_2$; SF$_5$-CH$_2$CHBr-(CH$_2$)$_5$-$(OCH_2CH_2)_m$-OCH=CH$_2$; SF$_5$-CH$_2$CHBr-(CH$_2$)$_5$-$(OCH_2CH_2)_m$-OAr(NCO)$_p$; SF$_5$-CH$_2$CHBr-(CH$_2$)$_6$-$(OCH_2CH_2)_m$-OCOCH=CH$_2$; SF$_5$-CH$_2$CHBr-(CH$_2$)$_6$-$(OCH_2CH_2)_m$-OCH=CH$_2$; SF$_5$-CH$_2$CHBr-(CH$_2$)$_6$-$(OCH_2CH_2)_m$-OAr(NCO)$_p$; SF$_5$-CH$_2$CHBr-(CH$_2$)$_7$-$(OCH_2CH_2)_m$-OCOCH=CH$_2$; SF$_5$-CH$_2$CHBr-(CH$_2$)$_7$-$(OCH_2CH_2)_m$-OCH=CH$_2$; SF$_5$-CH$_2$CHBr-(CH$_2$)$_7$-$(OCH_2CH_2)_m$-OAr(NCO)$_p$; SF$_5$-CH$_2$CHBr-(CH$_2$)$_8$-$(OCH_2CH_2)_m$-OCOCH=CH$_2$; SF$_5$-CH$_2$CHBr-(CH$_2$)$_8$-$(OCH_2CH_2)_m$-OCH=CH$_2$; SF$_5$-CH$_2$CHBr-(CH$_2$)$_8$-$(OCH_2CH_2)_m$-OAr(NCO)$_p$; SF$_5$-CH$_2$CHBr-(CH$_2$)$_9$-$(OCH_2CH_2)_m$-OCOCH=CH$_2$; SF$_5$-CH$_2$CHBr-(CH$_2$)$_9$-$(OCH_2CH_2)_m$-OCH=CH$_2$; SF$_5$-CH$_2$CHBr-(CH$_2$)$_9$-$(OCH_2CH_2)_m$-OAr(NCO)$_p$; SF$_5$-CH$_2$CHBr-(CH$_2$)$_{10}$-$(OCH_2CH_2)_m$-OCOCH=CH$_2$; SF$_5$-CH$_2$CHBr-(CH$_2$)$_{10}$-$(OCH_2CH_2)_m$-OCH=CH$_2$; SF$_5$-CH$_2$CHBr-(CH$_2$)$_{10}$-$(OCH_2CH_2)_m$-OAr(NCO)$_p$; SF$_5$-CH$_2$CHBr-(CH$_2$)$_{11}$-$(OCH_2CH_2)_m$-OCOCH=CH$_2$; SF$_5$-CH$_2$CHBr-(CH$_2$)$_{11}$-$(OCH_2CH_2)_m$-OCH=CH$_2$; SF$_5$-CH$_2$CHBr-(CH$_2$)$_{11}$-$(OCH_2CH_2)_m$-OAr(NCO)$_p$; SF$_5$-CH$_2$CHBr-(CH$_2$)$_{12}$-$(OCH_2CH_2)_m$-OCOCH=CH$_2$; SF$_5$-CH$_2$CHBr-(CH$_2$)$_{12}$-$(OCH_2CH_2)_m$-OCH=CH$_2$; SF$_5$-CH$_2$CHBr-(CH$_2$)$_{12}$-$(OCH_2CH_2)_m$-OAr(NCO)$_p$; SF$_5$-CH$_2$CHBr-(CH$_2$)$_{13}$-$(OCH_2CH_2)_m$-OCOCH=CH$_2$; SF$_5$-CH$_2$CHBr-(CH$_2$)$_{13}$-$(OCH_2CH_2)_m$-OCH=CH$_2$; SF$_5$-CH$_2$CHBr-(CH$_2$)$_{13}$-$(OCH_2CH_2)_m$-OAr(NCO)$_p$; SF$_5$-CH$_2$CHBr-(CH$_2$)$_{14}$-$(OCH_2CH_2)_m$-OCOCH=CH$_2$; SF$_5$-CH$_2$CHBr-(CH$_2$)$_{14}$-$(OCH_2CH_2)_m$-OCH=CH$_2$; SF$_5$-CH$_2$CHBr-(CH$_2$)$_{14}$-$(OCH_2CH_2)_m$-OAr(NCO)$_p$; SF$_5$-CH$_2$CHBr-(CH$_2$)$_{15}$-$(OCH_2CH_2)_m$-OCOCH=CH$_2$; SF$_5$-CH$_2$CHBr-(CH$_2$)$_{15}$-$(OCH_2CH_2)_m$-OAr(NCO)$_p$; SF$_5$-CH$_2$CHBr-(CH$_2$)$_{16}$-$(OCH_2CH_2)_m$-OCOCH=CH$_2$; SF$_5$-CH$_2$CHBr-(CH$_2$)$_{16}$-$(OCH_2CH_2)_m$-OCH=CH$_2$; SF$_5$-CH$_2$CHBr-(CH$_2$)$_{16}$-$(OCH_2CH_2)_m$-OAr(NCO)$_p$; SF$_5$-CH$_2$CHBr-(CH$_2$)$_{17}$-$(OCH_2CH_2)_m$-OCOCH=CH$_2$; SF$_5$-CH$_2$CHBr-(CH$_2$)$_{17}$-$(OCH_2CH_2)_m$-OAr(NCO)$_p$; SF$_5$-CH$_2$CHBr-(CH$_2$)$_{18}$-$(OCH_2CH_2)_m$-OCOCH=CH$_2$; SF$_5$-CH$_2$CHBr-(CH$_2$)$_{18}$-$(OCH_2CH_2)_m$-OCH=CH$_2$; SF$_5$-CH$_2$CHBr-(CH$_2$)$_{19}$-$(OCH_2CH_2)_m$-OCOCH=CH$_2$; SF$_5$-CH$_2$CHBr-(CH$_2$)$_{19}$-$(OCH_2CH_2)_m$-OAr(NCO)$_p$; SF$_5$-CH$_2$CHBr-(CH$_2$)$_{20}$-$(OCH_2CH_2)_m$-OCOCH=CH$_2$; SF$_5$-CH$_2$CHBr-(CH$_2$)$_{20}$-$(OCH_2CH_2)_m$-OAr(NCO)$_p$; SF$_5$-CH$_2$CHBr-(CH$_2$)$_{21}$-$(OCH_2CH_2)_m$-OCOCH=CH$_2$; SF$_5$-CH$_2$CHBr-(CH$_2$)$_{21}$-$(OCH_2CH_2)_m$-OCH=CH$_2$; SF$_5$-CH$_2$CHBr-(CH$_2$)$_{21}$-$(OCH_2CH_2)_m$-OAr(NCO)$_p$; SF$_5$-CH$_2$CHBr-(CH$_2$)$_{22}$-$(OCH_2CH_2)_m$-OCOCH=CH$_2$; SF$_5$-CH$_2$CHBr-(CH$_2$)$_{22}$-$(OCH_2CH_2)_m$-OCH=CH$_2$; SF$_5$-CH$_2$CHBr-(CH$_2$)$_{23}$-$(OCH_2CH_2)_m$-OAr(NCO)$_p$; SF$_5$-CH$_2$CHBr-(CH$_2$)$_{23}$-$(OCH_2CH_2)_m$-OCOCH=CH$_2$; SF$_5$-CH$_2$CHBr-(CH$_2$)$_{23}$-$(OCH_2CH_2)_m$-OCH=CH$_2$; SF$_5$-CH$_2$CHBr-(CH$_2$)$_{23}$-$(OCH_2CH_2)_m$-OAr(NCO)$_p$; SF$_5$-CH$_2$CHBr-(CH$_2$)$_{24}$-$(OCH_2CH_2)_m$-OCOCH=CH$_2$; SF$_5$-CH$_2$CHBr-(CH$_2$)$_{24}$-$(OCH_2CH_2)_m$-OCH=CH$_2$; or SF$_5$-CH$_2$CHBr-(CH$_2$)$_{24}$-$(OCH_2CH_2)_m$-OAr(NCO)$_p$;

wherein m is an integer from the range 0 to 1000, and p is 1 or 2.

Column 47, Line 60 through Column 46, Line 37 – Delete All and replace with:

37. A compound according to claim 1, wherein said compound is
CF$_3$-O-(CH$_2$)$_4$-N$^+$R$^1$R$^2$R$^3$Z$^-$; CF$_3$-O-(CH$_2$)$_4$-P$^+$R$^1$R$^2$R$^3$Z$^-$; CF$_3$-O-(CH$_2$)$_4$-O-glucoside; CF$_3$-O-(CH$_2$)$_5$-N$^+$R$^1$R$^2$R$^3$Z$^-$; CF$_3$-O-(CH$_2$)$_5$-P$^+$R$^1$R$^2$R$^3$Z$^-$; CF$_3$-O-(CH$_2$)$_5$-O-glucoside; CF$_3$-O-(CH$_2$)$_6$-N$^+$R$^1$R$^2$R$^3$Z$^-$; CF$_3$-O-(CH$_2$)$_6$-P$^+$R$^1$R$^2$R$^3$Z$^-$; CF$_3$-O-(CH$_2$)$_6$-O-glucoside; CF$_3$-O-(CH$_2$)$_7$-N$^+$R$^1$R$^2$R$^3$Z$^-$; CF$_3$-O-(CH$_2$)$_7$-P$^+$R$^1$R$^2$R$^3$Z$^-$; CF$_3$-O-(CH$_2$)$_7$-O-glucoside; CF$_3$-O-(CH$_2$)$_8$-N$^+$R$^1$R$^2$R$^3$Z$^-$; CF$_3$-O-(CH$_2$)$_8$-P$^+$R$^1$R$^2$R$^3$Z$^-$; CF$_3$-O-(CH$_2$)$_8$-O-glucoside; CF$_3$-O-(CH$_2$)$_9$-N$^+$R$^1$R$^2$R$^3$Z$^-$; CF$_3$-O-(CH$_2$)$_9$-P$^+$R$^1$R$^2$R$^3$Z$^-$; CF$_3$-O-(CH$_2$)$_9$-O-glucoside; CF$_3$-O-(CH$_2$)$_{10}$-N$^+$R$^1$R$^2$R$^3$Z$^-$; CF$_3$-O-(CH$_2$)$_{10}$-P$^+$R$^1$R$^2$R$^3$Z$^-$; CF$_3$-O-(CH$_2$)$_{10}$-O-glucoside; CF$_3$-O-(CH$_2$)$_{11}$-N$^+$R$^1$R$^2$R$^3$Z$^-$;

$CF_3\text{-}O\text{-}(CH_2)_{11}\text{-}P^+R^1R^2R^3Z^-$; $CF_3\text{-}O\text{-}(CH_2)_{11}\text{-}O\text{-glucoside}$; $CF_3\text{-}O\text{-}(CH_2)_{12}\text{-}N^+R^1R^2R^3Z^-$; $CF_3\text{-}O\text{-}(CH_2)_{12}\text{-}P^+R^1R^2R^3Z^-$; $CF_3\text{-}O\text{-}(CH_2)_{12}\text{-}O\text{-glucoside}$; $CF_3\text{-}O\text{-}(CH_2)_{13}\text{-}N^+R^1R^2R^3Z^-$; $CF_3\text{-}O\text{-}(CH_2)_{13}\text{-}P^+R^1R^2R^3Z^-$; $CF_3\text{-}O\text{-}(CH_2)_{13}\text{-}O\text{-glucoside}$; $CF_3\text{-}O\text{-}(CH_2)_{14}\text{-}N^+R^1R^2R^3Z^-$; $CF_3\text{-}O\text{-}(CH_2)_{14}\text{-}P^+R^1R^2R^3Z^-$; $CF_3\text{-}O\text{-}(CH_2)_{14}\text{-}O\text{-glucoside}$; $CF_3\text{-}O\text{-}(CH_2)_{15}\text{-}N^+R^1R^2R^3Z^-$; $CF_3\text{-}O\text{-}(CH_2)_{15}\text{-}P^+R^1R^2R^3Z^-$; $CF_3\text{-}O\text{-}(CH_2)_{15}\text{-}O\text{-glucoside}$; $CF_3\text{-}O\text{-}(CH_2)_{16}\text{-}N^+R^1R^2R^3Z^-$; $CF_3\text{-}O\text{-}(CH_2)_{16}\text{-}P^+R^1R^2R^3Z^-$; $CF_3\text{-}O\text{-}(CH_2)_{16}\text{-}O\text{-glucoside}$; $CF_3\text{-}O\text{-}(CH_2)_{17}\text{-}N^+R^1R^2R^3Z^-$; $CF_3\text{-}O\text{-}(CH_2)_{17}\text{-}P^+R^1R^2R^3Z^-$; $CF_3\text{-}O\text{-}(CH_2)_{17}\text{-}O\text{-glucoside}$; $CF_3\text{-}O\text{-}(CH_2)_{18}\text{-}N^+R^1R^2R^3Z^-$; $CF_3\text{-}O\text{-}(CH_2)_{18}\text{-}P^+R^1R^2R^3Z^-$; $CF_3\text{-}O\text{-}(CH_2)_{18}\text{-}O\text{-glucoside}$; $CF_3\text{-}O\text{-}(CH_2)_{19}\text{-}N^+R^1R^2R^3Z^-$; $CF_3\text{-}O\text{-}(CH_2)_{19}\text{-}P^+R^1R^2R^3Z^-$; $CF_3\text{-}O\text{-}(CH_2)_{19}\text{-}O\text{-glucoside}$; $CF_3\text{-}O\text{-}(CH_2)_{20}\text{-}N^+R^1R^2R^3Z^-$; $CF_3\text{-}O\text{-}(CH_2)_{20}\text{-}P^+R^1R^2R^3Z^-$; $CF_3\text{-}O\text{-}(CH_2)_{20}\text{-}O\text{-glucoside}$; $CF_3\text{-}O\text{-}(CH_2)_{21}\text{-}N^+R^1R^2R^3Z^-$; $CF_3\text{-}O\text{-}(CH_2)_{21}\text{-}P^+R^1R^2R^3Z^-$; $CF_3\text{-}O\text{-}(CH_2)_{21}\text{-}O\text{-glucoside}$; $CF_3\text{-}O\text{-}(CH_2)_{22}\text{-}N^+R^1R^2R^3Z^-$; $CF_3\text{-}O\text{-}(CH_2)_{22}\text{-}P^+R^1R^2R^3Z^-$; $CF_3\text{-}O\text{-}(CH_2)_{22}\text{-}O\text{-glucoside}$; $CF_3\text{-}O\text{-}(CH_2)_{23}\text{-}N^+R^1R^2R^3Z^-$; $CF_3\text{-}O\text{-}(CH_2)_{23}\text{-}P^+R^1R^2R^3Z^-$; $CF_3\text{-}O\text{-}(CH_2)_{23}\text{-}O\text{-glucoside}$; $CF_3\text{-}O\text{-}(CH_2)_{24}\text{-}N^+R^1R^2R^3Z^-$; $CF_3\text{-}O\text{-}(CH_2)_{24}\text{-}P^+R^1R^2R^3Z^-$; or $CF_3\text{-}O\text{-}(CH_2)_{24}\text{-}O\text{-glucoside}$.

Column 48, Line 48 reads: "$(CH_2)\text{-}P+R^1R^2R^3Z$; $SF_5\text{-}(CH_2)_{11}\text{-}N^+R^1R^2R^3Z^-$;" should read -- $(CH_2)_{10}\text{-} N^+R^1R^2R^3Z^-$; --.

Column 48, Line 59 reads: "$(CH_2)_{18}\text{-}P^+R^1R^2R^3Z$; $SF_5\text{-}(CH_2)_{19}\text{-}P^+$" should read -- $(CH_2)_{18}\text{-}P^+R^1R^2R^3Z^-$; $SF_5(CH_2)_{19}\text{-}N^+R^1R^2R^3Z^-$; $SF_5\text{-}(CH_2)_{19}\text{-}P^+$ --.

Column 52, Lines 9 through 15 reads:

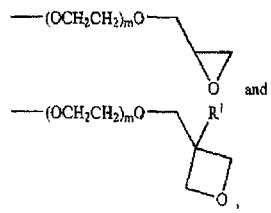

and

Should read –